US006051409A

United States Patent [19]
Hansen et al.

[11] Patent Number: 6,051,409
[45] Date of Patent: Apr. 18, 2000

[54] METHOD FOR ACHIEVING INTEGRATION OF EXOGENOUS DNA DELIVERED BY NON-BIOLOGICAL MEANS TO PLANT CELLS

[75] Inventors: Geneviéve Hansen, Durham; Mary-Dell Chilton, Raleigh, both of N.C.

[73] Assignee: Novartis Finance Corporation, New York, N.Y.

[21] Appl. No.: 08/717,676

[22] Filed: Sep. 23, 1996

Related U.S. Application Data

[60] Provisional application No. 60/004,220, Sep. 25, 1995, and provisional application No. 60/020,253, Jun. 19, 1996.

[51] Int. Cl.[7] .............................. A01H 5/00; C12N 5/14; C12N 15/33; C12N 15/82
[52] U.S. Cl. .................................... 435/172.3; 435/320.1; 435/419; 536/23.72; 800/205; 800/DIG. 17; 800/DIG. 26; 800/DIG. 27; 800/DIG. 43; 800/DIG. 56; 800/DIG. 57; 800/DIG. 58; 800/DIG. 63
[58] Field of Search .............................. 435/172.3, 320.1, 435/419; 800/205, DIG. 17, DIG. 26, DIG. 27, DIG. 43, DIG. 56, DIG. 57, DIG. 58, DIG. 63

[56] References Cited

U.S. PATENT DOCUMENTS

| | | | |
|---|---|---|---|
| 5,036,006 | 7/1991 | Sanford et al. | 435/170.1 |
| 5,231,019 | 7/1993 | Paszkowski et al. | 435/172.3 |
| 5,302,523 | 4/1994 | Coffee et al. | 435/172.1 |

FOREIGN PATENT DOCUMENTS

| | | |
|---|---|---|
| 4309203C1 | 3/1993 | Denmark . |
| 4344929A1 | 12/1993 | Denmark . |
| 0486234A2 | 11/1991 | European Pat. Off. . |
| WO 91/02071 | 2/1991 | WIPO . |
| WO 92/20809 | 11/1992 | WIPO . |
| WO 95/05471 | 2/1995 | WIPO . |

OTHER PUBLICATIONS

Citovsky, et al., "Nuclear Localization of Agrobacterium VirE2 Protein in Plant Cells", *Science*, 256:1802–1805 (1992).

Escudero, et al., "Intracellular Agrobacterium can transfer DNA to the cell nucleus of the host plant", *Proc. Natl. Acad. Sci.*, 92:230–234 (1995).

Tinland, et al. "The *Agrobacterium tumefaciens* virulence D2 protein is responsible for precise integratio of T–DNA into the plant genome", *The EMBO Journal*, 14(14):3585–3595 (1995).

Zupan, et al., "Transfer of T–DNA from *Agrobacterium* to the Plant Cell", *Plant Physiol.*, 107:1041–1047 (1995).

Chilton, Mary–Dell, "*Agrobacterium* gene transfer: Progress on a poor man's vector for maize", *Proc. Natl. Acad. Sci. USA*, 90:3119–3120 (1993).

Citovsky, et a., "Nuclear import of *Agrobacterium* VirD2 and VirE2 proteins in maize and tobacco", *Proc. Natl. Acad. Sci. USA*, 91:3210–3214 (1994).

De Vos, et al., "Expression of *Agrobacterium* Nopaline–Specific VirD1, VirD2, and VirC1 Proteins ant Their Requirements for T–strand Production *E. coli*", *Molecular Plant–Microbe Interactions*, 2(2):43–52 (1989).

Gallie, et al., "Visualizing mRNA Expression in Plant Protoplasts: Factors Influencing Efficient mRNA Uptake and Translation", *The Plant Cell*, 1:301–311 (1989).

Gallie, Daniel R., "Introduction of mRNA to plant protoplasts using polyethylene glycol", *Plant Cell Reports*, 13:119–122 (1993).

Ghai, et al., "The *virD* operon of *Agrobacterium tumefaciens* Ti plasmid encodes a DNA–relaxing enzyme", *Proc. Natl. Acad. Sci. USA*, 86:3109–3113 (1989).

Gheysen, et al., "Illegitimate recombination in plants: a model for T–DNA integration", *Genes & Development*, 5:287–297 (1991).

Herman, et al., "Plant chromosome/marker gene fusion assay for study of normal and trncated T–DNA integration events", *Mol. Gen. Genet.*, 224:248–256 (1990).

Jasper, et al., "*Agrobacterium* T–strand production in vitro: Sequence–specific cleavage and 5' protection of single–stranded DNA templates by purified VirD2 protein", *Proc. Natl. Acad. Sci. USA*, 91:694–698 (1994).

Klein, et al., "Stable genetic transformation of intact *Nicotiana* cells by the particle bombardment process", *Proc. Natl. Acad. Sci. USA*, 85:8502–8505 (1988).

Koncz, et al., "9. Homology Recognition During T–DNA Integration into the Plant Genome", *J. Paszkowski (ed.), Homologous Recombination and Gene Silencing in Plants*, 167–189 (1994).

Koziel, et al., "Field Performance of Elite Transgenic Maize Plants Expressing an Insecticidal Protein Derived from *Bacillus thuringiensis*", *Bio/Technology*, 11: 194–200 (1993).

Matzke, et al., "How and Why Do Plants Inactive Homologous (Trans)genes?[1]", *Plant Physiol.*, 107:679–685 (1995).

(List continued on next page.)

*Primary Examiner*—David T. Fox
*Assistant Examiner*—Amy J. Nelson
*Attorney, Agent, or Firm*—Thomas Hoxie, Esq.

[57] ABSTRACT

The present invention provides an improved method for achieving stable integration of an exogenous DNA fragment in intact form into the genome of a eukaryotic cell, particularly a plant cell. The method comprises providing the exogenous DNA together with one or more proteins which promote integration of the exogenous DNA to the eukaryotic cell targeted for transformation, wherein the proteins are provided in the form of a chimeric gene or translatable RNA capable of expression in the eukaryotic cell. The method is particularly applied to plant cells to achieve stable integration of an exogenous DNA fragment bounded by T-DNA borders in intact form using integration-promoting proteins derived from Agrobacterium. Transgenic cultures, tissues and whole organisms, particularly transgenic plants, can be generated from cells transformed according to the method of the invention.

18 Claims, 31 Drawing Sheets

OTHER PUBLICATIONS

Mayerhofer, et al., "T–DNA integration: a mode of illegitimate recombination in plants", *The EMBO Journal*, 10(3):697–704 (1991).

Negrutiu, et al., "Hybrid genes in the analysis of transformation conditions", *Plant Molecular Biology*, 8:363–373 (1987).

Ohba, et al., "DNA rearrangement associated with the integration of T–DNA in tobacco: an example for multiple duplications of DNA around the integration target", *The Plant Journal*, 7(1):157–164 (1995).

Okada, et al., "Introduction of Functional RNA into Plant Protoplasts by Electroporation", *Plant Cell Physiol.*, 27(4):619–626 (1986).

Pansegrau, et al., "Site–specific cleavage and joining of single–stranded DNA by VirD2 protein of *Agrobacterium tumefaciens* Ti plasmids: Analogy to bacterial conjugation", *Proc. Natl. Acad. Sci. USA*, 90:11538–11542 (1993).

Rasmussen, et al., "Biolistic transformation of tobacco and maize suspension cells using bacterial cells as microprojectiles", *Plant Cell Reports*, 13:212–217 (1994).

Regensburg–Tuïnk, et al., "Transgenic *N. glauca* plants expressing bacterial virulence gene *virF* are converted into hosts for nopaline strains of *A. tumefaciens*", *Nature*, 363:69–71 (1993).

Rossi, et al., "The VirD2 protein of *Agrobacterium tumefaciens* carries nuclear localizatino signals important for transfer of T–DNA to plants", *Mol. Gen. Genet.*, 239: 345–353 (1993).

Saul, et al., "Direct DNA transfer to protoplasts with and without electroporation", *Plant Molecular Biology Manual*, AI:1–16 (1988).

Stachel, et al., "Generation of single–stranded T–DNA molecules during the initial stages of T–DNA transfer from *Agrobacterium tumefaciens* to plant cells", *Nature*, 322:706–712 (1986).

Tinland, et al., "The *Agrobacterium tumefaciens* Virulence D2 Protein is Responsible for Precise Integration of T–DNA into the Plant Genome", *Friedrich Miescher–Institut*, 1–39.

van Haaren, et al., "Mutational analysis of the conserved domains of a T–region border repeat of *Agrobacterium tumefaciens*", *Plant Molecular Biology*, 13:523–531 (1989).

Vogel, et al., "Mutational Analysis of *Agrobacterium tumefaciens* virD2: Tyrosine 29 Is Essential for Endonuclease Activity", *Journal of Bacteriology*, 174(1):303–308 (1992).

Walker, et al., "GUS mRNA Delivery and Expression in Plant Cells via Particle Bombardment", *Annual Meeting Abstracts*, Abstract #218.

```
PRETTY of: *.junction
              1                                                    50
 1.Junction  GGATCCGGCA AAGAAAATAT TATATTATTA ACATTAGCTT CCTCCAACAA
2a.Junction  GGATCCGGCA TTATGTTTAA TATATCCACA GTAAAATCAC AGCAATTACA
2b.Junction  GGATCCGGCC CAGTAAAGAT TGTTTCATAG ATATCAATCA AGAAAAGAGT
 3.Junction  GGATCCGGCA AACAAAGCAC CAAATCATAA TTATTATTAG TTCTCATAAC
 5.Junction  GGATCCGGCA TGAGTAGAAA TGCATtCAAA ATCTTGAaTC ATCATTACAT
Rb.Junction  GGATCCggca ggatatatac cgctgtaatt cTGCA..... ..........
```

FIG.3

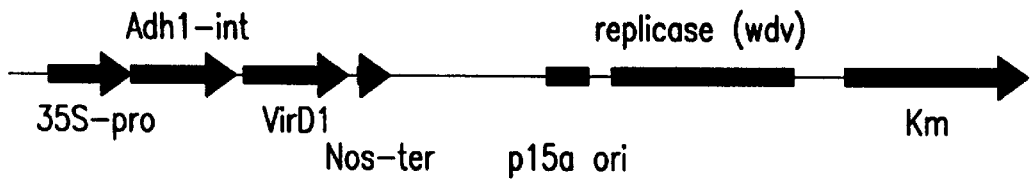
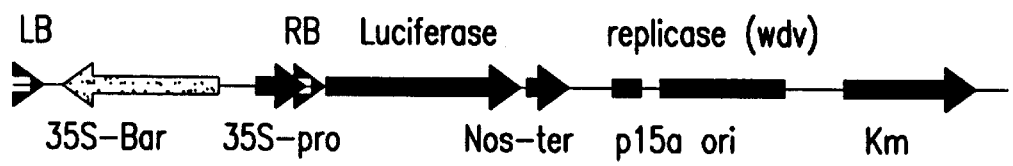
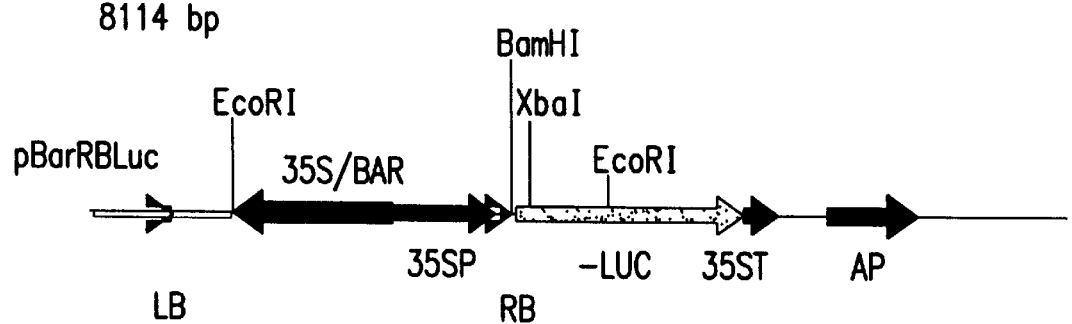
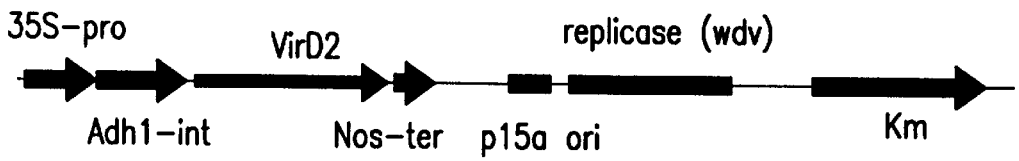
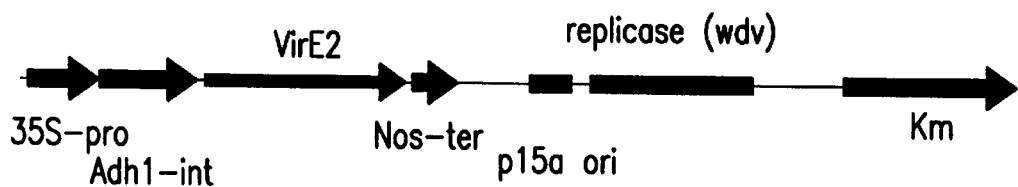
FIG.5

```
                            SEQUENCE LISTING (1) GENERAL INFORMATION:

(iii) NUMBER OF SEQUENCES: 31

(2) INFORMATION FOR SEQ ID NO:1:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "right T-DNA border"

(xi) SEQUENCE DESCRIPTION: SEQ ID NO:1:

GNNTGNCAGG ATATATNNNN NNGTNAN                                              27

(2) INFORMATION FOR SEQ ID NO:2:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "left T-DNA border"

(xi) SEQUENCE DESCRIPTION: SEQ ID NO:2:

GGTGGCAGGA TATATNNNNN TGTAAA                                               26

(2) INFORMATION FOR SEQ ID NO:3:

(i) SEQUENCE CHARACTERISTICS:
            (A) LENGTH: 8 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "core sequence near right
                T-DNA border"

(xi) SEQUENCE DESCRIPTION: SEQ ID NO:3:

TGTTTGTT                                                                    8
```

(2) INFORMATION FOR SEQ ID NO:4:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "core sequence near right
            T-DNA border"

(xi) SEQUENCE DESCRIPTION: SEQ ID NO:4:

ATTAGTTC                                                                  8

(2) INFORMATION FOR SEQ ID NO:5:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic linker used in
            construction of pCIB1711"

(xi) SEQUENCE DESCRIPTION: SEQ ID NO:5:

TCGACATG                                                                  8

(2) INFORMATION FOR SEQ ID NO:6:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide used in
            construction of pCIB1711"

(xi) SEQUENCE DESCRIPTION: SEQ ID NO:6:

GATCCCTGCA GA                                                             12

(2) INFORMATION FOR SEQ ID NO:7:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide used in
            construction of pCIB1711"

(xi) SEQUENCE DESCRIPTION: SEQ ID NO:7:

AGCTTCTGCA GG                                                             12

(2) INFORMATION FOR SEQ ID NO:8:

(i) SEQUENCE CHARACTERISTICS:
        (A) LENGTH: 150 base pairs
        (B) TYPE: nucleic acid
        (C) STRANDEDNESS: single
        (D) TOPOLOGY: linear (ii) MOLECULE TYPE: other nucleic acid (A) DESCRIPTION: /desc = "oligomer used in
    construction of pCIB1711"

(xi) SEQUENCE DESCRIPTION: SEQ ID NO:8:

ATCTCCACTG ACGTAAGGGA TGACGCACAA TCCCACTATC CTTCGCAAGA CCCTTCCTCT      60

ATATAAGGAA GTTCATTTCA TTTGGAGAGG GATCCCTGCA GGACACGCTG AAATCACCAG     120

TCTCTCTCTA CAAATCTATC TCTCTCTATG                                     150

(2) INFORMATION FOR SEQ ID NO:9:

(i) SEQUENCE CHARACTERISTICS:
        (A) LENGTH: 154 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligomer used in
            construction of pCIB1711"

(xi) SEQUENCE DESCRIPTION: SEQ ID NO:9:

GATCCATAGA GAGAGATAGA TTTGTAGAGA GAGACTGGTG ATTTCAGCGT GTCCTGCAGG      60

GATCCCTCTC CAAATGAAAT GAACTTCCTT ATATAGAGGA AGGGTCTTGC GAAGGATAGT    120

GGGATTGTGC GTCATCCCTT ACGTCAGTGG AGAT                                154

(2) INFORMATION FOR SEQ ID NO:10:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "duplex used in construction
            of pCIB1711"

(xi) SEQUENCE DESCRIPTION: SEQ ID NO:10:

ATCCGGCAGG ATATATACCG TTGTAATTCT GCA                                  33

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer located in the
            CaMV35S promoter at a distance of 106-bp from the right border
            sequence"

(xi) SEQUENCE DESCRIPTION: SEQ ID NO:11:

CCACTATCCT TCGCAAGACC                                                 20

(2) INFORMATION FOR SEQ ID NO:12:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide used in
            construction of pRec (Fig. 4D)"

```
    (ix) FEATURE:
          (A) NAME/KEY: misc_signal
          (B) LOCATION: 10..12
          (D) OTHER INFORMATION: /note= "start codon of recombinase"

(xi) SEQUENCE DESCRIPTION: SEQ ID NO:12:

TCGAGTTGCA TGCAG                                                        15

(2) INFORMATION FOR SEQ ID NO:13:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "linder containing an SphI
              site used in constructing pRec (Fig. 4D)"

(xi) SEQUENCE DESCRIPTION: SEQ ID NO:13:

GATCGCAGCA TGCCTAG                                                      17

(2) INFORMATION FOR SEQ ID NO:14:

(i) SEQUENCE CHARACTERISTICS:
          (A) LENGTH: 45 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "oligonucleotide used in
              constructing p1RSLuc (Fig. 4E)"

(ix) FEATURE:
          (A) NAME/KEY: misc_feature
          (B) LOCATION: 5..10
          (D) OTHER INFORMATION: /note= "HindIII site"

(ix) FEATURE:
          (A) NAME/KEY: misc_feature
          (B) LOCATION: 11..41
          (D) OTHER INFORMATION: /note= "RS site"

(xi) SEQUENCE DESCRIPTION: SEQ ID NO:14:

GATCAAGCTT TTGATGAAAG AATACGTTAT TCTTTCATCA AGATC                       45

(2) INFORMATION FOR SEQ ID NO:15:

(i) SEQUENCE CHARACTERISTICS:
          (A) LENGTH: 46 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "oligonucleotide used in
              construction of p2RSLuc (Fig. 4F)"

(ix) FEATURE:
          (A) NAME/KEY: misc_feature
          (B) LOCATION: 6..11
          (D) OTHER INFORMATION: /note= "PstI site"

(ix) FEATURE:
          (A) NAME/KEY: misc_feature
          (B) LOCATION: 12..42
          (D) OTHER INFORMATION: /note= "RS site"

(xi) SEQUENCE DESCRIPTION: SEQ ID NO:15:
```

AGCTACTGCA GTTGATGAAA GAATACGTTA TTCTTTCATC AACTAG                46

(2) INFORMATION FOR SEQ ID NO:16:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide used in
            constructing p2RSLuc (Fig. 4F)"

(ix) FEATURE:
        (A) NAME/KEY: misc_feature
        (B) LOCATION: 5..10
        (D) OTHER INFORMATION: /note= "HindIII site"

(ix) FEATURE:
        (A) NAME/KEY: misc_feature
        (B) LOCATION: 11..41
        (D) OTHER INFORMATION: /note= "RS site"

(ix) FEATURE:
        (A) NAME/KEY: misc_feature
        (B) LOCATION: 1..45
        (D) OTHER INFORMATION: /note= "same as seq id no:14"

(xi) SEQUENCE DESCRIPTION: SEQ ID NO:16:

GATCAAGCTT TTGATGAAAG AATACGTTAT TCTTTCATCA AGATC                45

(2) INFORMATION FOR SEQ ID NO:17:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide used in
            Example 5"

(xi) SEQUENCE DESCRIPTION: SEQ ID NO:17:

AATTCATGGA TCTTTCTGGC AATGAGAAAT CCAGG                            35

(2) INFORMATION FOR SEQ ID NO:18:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide used in
            construction of p35SD1D2"

(xi) SEQUENCE DESCRIPTION: SEQ ID NO:18:

GTGCCTTGCC TTCTACTCCC CCAACTCCCT CTCCTAGCAC GCCTCCGACA CCTAGCCCCG   60
AT                                                                 62

(2) INFORMATION FOR SEQ ID NO:19:

(i) SEQUENCE CHARACTERISTICS:
        (A) LENGTH: 56 base pairs
        (B) TYPE: nucleic acid
        (C) STRANDEDNESS: single
        (D) TOPOLOGY: linear 6,051,409

77

78

-continued (ii) MOLECULE TYPE: other nucleic acid
        (A) DESCRIPTION: /desc = "oligonucleotide used in
            construction of p35SD1D2"

(xi) SEQUENCE DESCRIPTION: SEQ ID NO:19:

CGGGGCTAGG TGTCGGAGGC GTGCTAGGAG AGGGAGTTGG GGGAGTAGAA GGCAAG          56

(2) INFORMATION FOR SEQ ID NO:20:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide used in
            constructing p35SD2D1"

(xi) SEQUENCE DESCRIPTION: SEQ ID NO:20:

AATTCTCAAA ACACACCAGA GTCACGTCGA GTGAGACTGC CATCAACCAG CAT             53

(2) INFORMATION FOR SEQ ID NO:21:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide used in
            constructing p35SD2D1"

(xi) SEQUENCE DESCRIPTION: SEQ ID NO:21:

TATCCTTCTA CTCCCCCAAC TCCCTCTCCT AGCACGCCTC CGACACCTAG C               51

(2) INFORMATION FOR SEQ ID NO:22:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide used in
            constructing p35SD2D1"

(xi) SEQUENCE DESCRIPTION: SEQ ID NO:22:

AATTGGCTAG GTGTCGGAGG CGTGCTAGGA GAGGGAGTTG GGGGAGTAGA AGGA            54

(2) INFORMATION FOR SEQ ID NO:23:

(i) SEQUENCE CHARACTERISTICS:
        (A) LENGTH: 53 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "oligomer used in
            constructing pT7-A50 (Example 8)"

(ix) FEATURE:
        (A) NAME/KEY: misc_signal
        (B) LOCATION: 5..49
        (D) OTHER INFORMATION: /note= "complementary strand only between these bases"

(xi) SEQUENCE DESCRIPTION: SEQ ID NO:23:

```
GTACGCTTAA GCGATCGTAG CTATCTAGAC CATGGTTTCG AAGAGCTCAT CGA          53
```

(2) INFORMATION FOR SEQ ID NO:24:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "duplex oligonucleotide used
            in Example 9"

(xi) SEQUENCE DESCRIPTION: SEQ ID NO:24:

```
ATCCGGCAGG ATATATACCG TTGTAATTCT GCA                                33
```

(2) INFORMATION FOR SEQ ID NO:25:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide pair used
            in Example 9"

(xi) SEQUENCE DESCRIPTION: SEQ ID NO:25:

```
AATTCATGGA TCTTTCTGGC AATGAGAAAT CCAGG                              35
```

(2) INFORMATION FOR SEQ ID NO:26:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "lane "1.Junction" of Figure
            3"

(xi) SEQUENCE DESCRIPTION: SEQ ID NO:26:

```
GGATCCGGCA AGAAAATAT TATATTATTA ACATTAGCTT CCTCCAACAA               50
```

(2) INFORMATION FOR SEQ ID NO:27:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Lane "2a.Junction" in
            Figure 3"

(xi) SEQUENCE DESCRIPTION: SEQ ID NO:27:

```
GGATCCGGCA TTATGTTTAA TATATCCACA GTAAAATCAC AGCAATTACA              50
```

(2) INFORMATION FOR SEQ ID NO:28:

(i) SEQUENCE CHARACTERISTICS:
        (A) LENGTH: 50 base pairs
        (B) TYPE: nucleic acid
        (C) STRANDEDNESS: single
        (D) TOPOLOGY: linear -continued

```
    (ii) MOLECULE TYPE: other nucleic acid
        (A) DESCRIPTION: /desc = "Lane "2b.Junction" in
            Figure 3"

(xi) SEQUENCE DESCRIPTION: SEQ ID NO:28:

GGATCCGGCC CAGTAAAGAT TGTTTCATAG ATATCAATCA AGAAAAGAGT          50

(2) INFORMATION FOR SEQ ID NO:29:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Lane "3.Junction" in Figure
            3"

(xi) SEQUENCE DESCRIPTION: SEQ ID NO:29:

GGATCCGGCA AACAAAGCAC CAAATCATAA TTATTATTAG TTCTCATAAC          50

(2) INFORMATION FOR SEQ ID NO:30:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Lane "5.Junction" in Figure
            3"

(xi) SEQUENCE DESCRIPTION: SEQ ID NO:30:

GGATCCGGCA TGAGTAGAAA TGCATTCAAA ATCTTGAATC ATCATTACAT          50

(2) INFORMATION FOR SEQ ID NO:31:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Lane "Rb.Junction" in
            Figure 3"

(xi) SEQUENCE DESCRIPTION: SEQ ID NO:31:

GGATCCGGCA GGATATATAC CGCTGTAATT CTGCA                          35
```

METHOD FOR ACHIEVING INTEGRATION OF EXOGENOUS DNA DELIVERED BY NON-BIOLOGICAL MEANS TO PLANT CELLS

CROSS-REFERENCE TO RELATED APPLICATIONS

This application claims the benefit of U.S. Provisional Application No. 60/004,220, filed Sep. 25, 1995, and U.S. Provisional Application No. 60/020,253, filed Jun. 19, 1996.

FIELD OF THE INVENTION

The invention relates generally to the transformation of eukaryotic cells, particularly plant cells, with exogenous DNA and the generation of transgenic organisms, tissues or cultures from such cells.

BACKGROUND OF THE INVENTION

Several methods have been developed for introducing exogenous DNA molecules into eukaryotic cells in order to take advantage of the widespread benefits arising from the application of recombinant DNA technology to the production of transgenic organisms. These methods include physical, non-biological systems such as electroporation, microinjection, calcium phosphate or polyethylene glycol (PEG) mediated DNA uptake or cell fusion, and microprojectile bombardment (aka "biolistics") and modified biological systems such as Agrobacterium-mediated T-DNA transfer to plant cells (for a general and somewhat dated overview, see chapters 2 and 3 of "Plant Genetic Transformation and Gene Expression, A Laboratory Manual", ed. by Draper, J. et al., pub. by Blackwell Scientific Publications (1988); see also Potrykus, et al., "Direct Gene Transfer: State of the Art and Future Potential", *Plant Mol. Biol. Rep.* 3: 117–128 (1985)).

The methods which have been developed have allowed the stable transformation of a wide variety of organisms with exogenous DNA. In particular, the development of physical techniques such as microprojectile bombardment has overcome apparent host-range limitations imposed by biological systems. However, a common deficiency of these physical methods is that they do not provide any means for ordered integration of the delivered DNA into the cell genome. Consequently these methods must depend upon uncontrolled integration of the delivered DNA by poorly understood mechanisms, causing exogenous DNA to be integrated as multiple copies of random fragments usually at a single site in the cell genome.

Improving the predictability of stable transformation events arising from the physical introduction of exogenous DNA into the cell would significantly improve the utility and overall efficiency of these processes for producing genetically stable transformed organisms exhibiting stable expression of transgenes. One approach which has been taken to accomplish this goal has been to combine proteins which promote transformation and/or integration in biological systems with non-biological delivery techniques. In order to achieve the desired effect, it has been considered necessary to associate the proteins themselves with the exogenous DNA molecules in advance of delivery to the transformation target cell, thus mimicking as closely as possible the biological system from which the proteins are derived (see, e.g. international application no. PCT/EP94/02566 to Hohn et al. published Feb. 23, 1995 as WO 95/05471; international application no. PCT/US95/07543 to Conary, J. et al. published Dec. 21, 1995 as WO 95/34647).

SUMMARY OF THE INVENTION

The present invention provides an improved method for stably transforming eukaryotic cells with exogenous DNA. This improved method generally comprises providing to the eukaryotic cell targeted for transformation at least one chimeric gene or mRNA capable of producing one or more proteins that promote integration in combination with the exogenous DNA desired to be integrated.

In particular, the present invention provides an improved method for stably transforming plant cells with exogenous DNA, which combines positive attributes of *Agrobacterium tumefaciens* mediated T-DNA transfer and integration with non-biological delivery methods. This improved method comprises providing a plant cell with the exogenous DNA fragment desired to be integrated into the plant cell genome, bounded by T-DNA borders, along with at least one chimeric gene or RNA capable of expressing, in the plant cell, an Agrobacterium-derived protein that promotes the integration of the exogenous DNA. The Agrobacterium-derived protein provided according to the invention particularly includes VirD1, VirD2, and VirE2. Preferably, VirD2 and VirD1, either alone or in combination with VirC and/or VirE2, or a subcombination thereof, is used. Expression of the Agrobacterium-derived protein(s) in the plant cell causes the integration of the exogenous DNA as an intact fragment with predictable endpoints.

According to the invention, the exogenous DNA fragment bounded by T-DNA border sequences may be delivered to the plant cell or other eukaryotic cell by non-biological means such as, but not restricted to, electroporation, microinjection, induced uptake, microprojectile bombardment, or other means as are known in the art.

According to the invention, the Agrobacterium-derived protein(s) may also be delivered to the plant cell or other eukaryotic cell by non-biological means in the form of DNA (chimeric gene expressible in the cell) or RNA (RNA translatable in the cell).

The exogenous DNA fragment and the Agrobacterium-derived protein(s) in the form of DNA or RNA are temporally delivered so that the Agrobacterium-derived protein(s) are present in the plant cell or other eukaryotic cell after the exogenous DNA has been delivered and before the exogenous DNA has been integrated. This may preferably be achieved by simultaneous delivery of these components in a single step. Alternatively, the cell targeted for transformation may be derived from an organism or cell culture that has previously been stably transformed with a chimeric gene(s) capable of expressing the Agrobacterium-derived protein(s).

In another aspect of the invention, eukaryotic cells stably transformed with a discrete DNA fragment are regenerated to produce fertile transgenic organisms that stably express a desired transgene and pass it on to progeny in which stable expression of the transgene is inherited as a Mendelian trait.

BRIEF DESCRIPTION OF THE DRAWINGS

FIG. 3: Sequence analysis of target DNA integration sites after transformation of tobacco with pNeoRBLuc, p35SD1, and p35SD2 plasmids is provided. Numbers refer to the target clones designation numbers. The right border sequence carried by pNeoRBLuc is written in lower case letters (lane Rb.junction). The target sequences of fragment 1, 2a, 3 and 5, respectively show 100% homology with PSII of tobacco (X62426; nt 908), 100% with NtpII10 of tobacco (X70088; nt 573), 100% with ribulose 1,5-bisphosphate carboxylase of tobacco (X02353; nt 2174), and 80% homology with a chlorophyll binding protein of petunia (M21317; nt 1013). The lanes in FIG. 3 are set forth as SEQ ID NOS:26–31.

FIG. 5: Schematic representation of plasmids pwAdhD1, pwAdhD2, pwBarRBLuc, and pBARRBLuc used in Example 5.

DEFINITIONS

Figure 1:
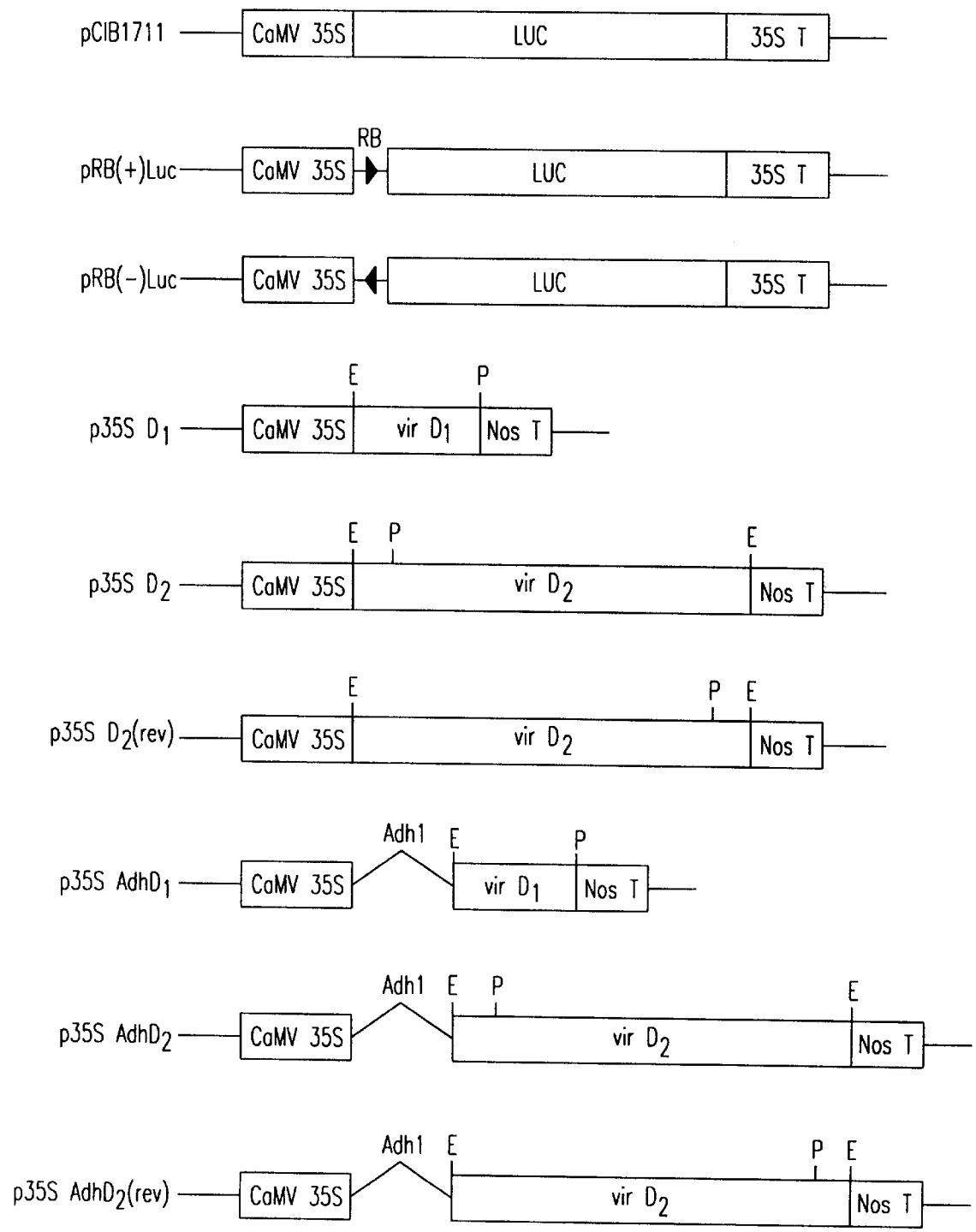
FIG. 1: Plasmid structures used in the experiments described in Example 1 are shown. Components of these plasmids are described in the Materials and Methods section of Example 1. RB corresponds to the 25-bp right border sequence. Restriction sites are indicated as follows: E=EcoRI; P=PstI.

Integration: As used herein "integration" is used to refer generally to the process by which an exogenous DNA molecule delivered into a eukaryotic cell is stably incorporated into the genomic DNA of the eukaryotic cell.

Microprojectile Bombardment:

As used herein "microprojectile bombardment" (aka "biolistics") is used to refer to the general method of delivering nucleic acids, including DNA and RNA, to a living cell by coating the nucleic acids on a microprojectile and propelling the coated microprojectile into the living cell (see, e.g. Examples 1–4, U.S. Pat. No. 5,036,006 issued Jul. 30, 1991 to Sanford, J. et al.; international application no. PCT/US90/04462 published Feb. 21, 1991 as WO 91/02071 (describing application of this approach to transformation of plants and cells thereof); see also U.S. Pat. No. 5,302,523 issued Apr. 12, 1994 to Coffee; Koziel et al., *Biotechnology* 11: 194–200 (1993)(describing the transformation of Elite inbred lines of maize by particle bombardment); Vasil et al., *Biotechnology* 11: 1553–1558 (1993); Weeks et al., *Plant Physiol.* 102: 1077–1084 (1993); Tanaka, T. et al., "Successful expression in pollen of various plant species of in vitro synthesized mRNA introduced by particle bombardment", *Plant Mol. Biol.* 28: 337–341 (1995); Vasil et al., *Biotechnology* 10: 667–674 (1992); Walker, L. et al., "GUS Messenger RNA Delivery and Expression in Plant Cells via Particle Bombardment", In Vitro Cell Dev. Biol. 26: 70A-#218 (1990); Iida, A. et al., *Appl. Microbiol. Biotechnol.* 33: 560–563 (1990); Gordon-Kamm et al., *Plant Cell* 2: 603–618 (1990); Fromm et al, *Biotechnology* 8: 833–839 (1990); Morikawa, H. et al., *Appl. Microbiol. Biotechnol.* 31: 320–322 (1989)).

Aerosol Beam Injection: As used herein "aerosol beam injection" is used to refer to the method of physically delivering nucleic acids to a living cell in the form of an aerosol beam (see, e.g. U.S. Pat. No. 5,240,842 issued Aug. 31, 1993 to Mets, L).

Electroporation: As used herein "electroporation" is used to refer to the method of delivering biological molecules, particularly nucleic acids such as DNA and RNA, to living cells by subjecting the cells to an electrical impulse in the presence of the biological molecules (see, e.g. U.S. Pat. No. 5,231,019 issued Jul. 27, 1993 to Paszkowski, J. et al.; chapter 3.3 of "Plant Genetic Transformation and Gene Expression, A Laboratory Manual", ed. by Draper, J. et al., pub. by Blackwell Scientific Publications (1988); Saul, M. W. et al., "Direct DNA Transfer to Protoplasts With and Without Electroporation", *Plant Molecular Biology Manual* A1: 1–16 (1988); Okada, K. et al., "Introduction of Functional RNA into Plant Protoplasts by Electroporation", *Plant Cell Physiol.* 27(4): 619–626 (1986); Shillito, R. D., et al., "High Efficiency Direct Gene Transfer to Plants", *Biotechnology* 3: 1099–1103 (1985); EP 0 292 435 (to Ciba-Geigy), EP 0 392 225 (to Ciba-Geigy) and WO 93/07278 (to Ciba-Geigy).

Microinjection: As used herein "microinjection" is used to refer to the method of directly injecting a biological substance, particularly DNA or RNA, into a living cell (see, e.g. chapter 3.4 of "Plant Genetic Transformation and Gene Expression, A Laboratory Manual, supra; Graessmann, M. et al., "Microinjection of Tissue Culture Cells", *Methods in Enzymology* 101: 482–492 (1983).

Induced Uptake: As used herein "induced uptake" is used to refer generally to methods which induce uptake of biological substances, particularly nucleic acids, by living cells (see, e.g. background section of U.S. Pat. No. 5,036,006 issued Jul. 30, 1991 to Sanford, J. et al.). Such methods include, in particular, polyethylene glycol (PEG) mediated uptake (see, e.g. chapter 3.2 of "Plant Genetic Transformation and Gene Expression, A Laboratory Manual", ed. by Draper, J. et al., pub. by Blackwell Scientific Publications (1988); Saul, M. W. et al., "Direct DNA Transfer to Protoplasts With and Without Electroporation", supra; Negrutiu et al., *Plant Mol. Biol* 8: 363–373 (1987) and heat shock treatment (see U.S. Pat. No. 5,231,019 issued Jul. 27, 1993 to Paszkowski, J. et al. assigned to Ciba-Geigy).

VirD.: As used herein "VirD" is used to refer to the genes or proteins derived from the the virulence (Vir) D operon of the Ti- and Ri plasmid which provide functions required for T-DNA transfer (for a review see Zambryski P. C., "Chronicles from the Agrobacterium-plant cell DNA transfer story" *Ann. Rev. Plant Physiol. Plant Mol. Biol.* 43: 465–490 (1992)). Particular genes and corresponding proteins from this region are designated by number according to where they occur on the VirD operon. For example, the first gene in the virulence D operon is designated "VirD1", the second is designated "VirD2", etc.

The virulence region DNA is not normally transferred to the plant cell nor integrated into the plant genome during Agrobacterium-mediated T-DNA transfer. Instead, the Vir gene products naturally act in trans to mobilize the T-DNA element from the bacterial Ti or Ri plasmid to the plant genome. The T-region and the Vir region can be separated on different plasmids without loss of functions (De Framond, A. J. et al., *Bio/Technology* 1:262–269 (1983); Hoekema et al, *Nature* 303: 179–180 (1983).

Two polypeptides encoded by the 5' half of the VirD locus play a key role in the initiation of DNA processing for T-DNA transfer from Agrobacterium to the plant cells: VirD1 and VirD2. VirD1 and VirD2 proteins are encoded by the first gene and the second gene of the VirD operon respectively (Stachel S. E. & Nester E. W. "The genetic and transcriptional organization of the vir region of the A6 Ti plasmid of *Agrobacterium tumefaciens. EMBO J.* 5:1445–1454 (1986). Genetic studies have demonstrated that the T-strand formation is mediated by products of the VirD operon (Yanofsky et al., *Cell* 47:471–477 (1986); Stachel et al., *EMBO J.* 6:857–863 (1987)). In particular the first and second genes of the VirD operon have been shown to encode the only polypeptides required for T-DNA border cleavage (De Vos & Zambryski, *Mol. Plant Microbe Inter.* 2:43–52 (1989); Filichkin & Gelvin, Mol. Microbiol 8:915–926 (1993); Jayaswal et al., *J. Bacteriol.* 169, :5035–5045 (1987); Porter et al., *Nucleic Acids Res.* 15:7503–7515 (1987); Stachel et al., *EMBO J.* 6:857–863 (1987)). This activity results in single-stranded cleavage (nicking) within the T-DNA border sequences (Stachel S. E. et al., "Generation of single-stranded T-DNA molecules during the initial stage of T-DNA transfer from *Agrobacterium tumefaciens* to plant cells" *Nature* (London) 322: 706–712 (198).; Yanofsky et al., *Cell* 47: 471–477 (1986); Wang et al., *Science* 235: 587–591 (1987); Albright et al.,*J. Bacteriol.* 169: 1046–1055 (1987)). VirD1/VirD2 cleave the T-DNA border sequence between the third and the fourth bases. Once these nicked molecules have been generated, the production of free linear, ssDNA copies of the bottom strand of the T-DNA (T-strand) is observed (Stachel et al., *Nature* (London) 322: 706–712 (1986).; Stachel et al., *EMBO J.* 6: 857–863 (1987)). VirD2 remains covalently attached to the 5' end of the T-DNA (for review, see Zupan J. R. & Zambryski, P. "Transfer of T-DNA from Agrobacterium to the plant cell". *Plant Physiol.* 107: 1041–1047 (1995)).

Studies of a VirD2 mutant that has lost the C-terminal 50% of VirD2 have demonstrated that only the N-terminal 50% of VirD2 is required for its role in nicking the T-DNA borders. However, this mutant is unable to elicit tumors on infected plants. The C-terminus thus appears to have a role in transfer of T-DNA in plant cells (reviewed in Zambryski P. C., "Chronicles from the Agrobacterium-plant cell DNA transfer story" *Ann. Rev. Plant Physiol. Plant Mol. Biol.* 43: 465–490 (1992)). This domain contains a bipartite nuclear localization signal (NLS) (Howard et al., *Cell* 68: 109–118 (1992)). The biological relevance of the NLS sequences was confirmed by the observation that Agrobacterium is severely reduced in tumorigenicity when the 2 basic structures of the bipartite NLS are deleted from VirD2 (Shurviton, *Proc. Natl. Acad. Sci.* (USA) 89, 11837–11841 (1992)).

VirD2 alone in vitro exerts a site-specific DNA cleaving-joining reaction on single-stranded DNA, indicating that this protein bears the catalytic activity required for DNA scission (Pansegrau et al., *Proc. Natl. Acad. Sci.* 90:11538–11542 (1993)). The combination of VirD1 and VirD2 of pTiC58 have been reported to be sufficient to catalyze the T-border specific cleavage in vitro by Scheiffle et al., *J. Biol. Chemistry* 270: 1269–1276 (1995) (but see Jasper et al., *Proc. Natl. Acad. Sci.* 91: 694–698 (1994).

A topoisomerase activity of type I was described for VirD1-containing extracts (Ghai & Das, *Proc. Natl. Acad. Sci.* 86: 319–3113 (1989). This activity was attributed to VirD1 and proposed to be required for relaxing the DNA in order to prepare it for cleavage by VirD2. However, more highly purified VirD1 protein did not show topoisomerase activity (Scheiffle et al., *J. Biol. Chemistry* 270:1269–1276 (1995)).

Amino acid sequence analysis of VirD2 has revealed that the N terminus is 85% conserved among strains of Agrobacterium carrying either octopine, nopaline ,or rhizogenes type plasmids (Hirayama et al., *Mol. Gen. Genet.* 213:229–237 (1988); Wang et al., *J. Bacteriol.* 172:4432–4440 (1990); Yanofsky et al., *Cell* 47:471–477 (1986)). The C-terminus is only 25% conserved, but the highest similarity is in the last 30 amino acids with the NLS signals (reviewed by Zambryski, 1992).

VirE: As used herein "VirE" is used to refer to the genes or corresponding proteins derived from the virulence (Vir) E operon of the Ti- and Ri plasmid which provide functions required for T-DNA transfer. The term "VirE2" is used herein to refer to the single-stranded DNA (ssDNA)-binding protein which has been identified as the product of the VirE2 gene on the VirE operon (Gielt, C. et al., *Proc. Natl. Acad. Sci.* 84: 9006–9010 (1987); Citovsky et al., *Science* 240: 501–504 (1988). VirE2 is believed to coat the T-strand along its length. The interaction of this protein with single-stranded DNA is non-specific. The nopaline VirE2 protein (Hirooka et al.,*J. Bacteriol.* 169: 1529–1536 (1987)) and the octopine VirE2 protein (Winans et al., *Nucleic Acids Res.* 15: 825–837 (1987)) contain nuclear localization signals. The VirE2 protein is believed to be a major part of the T-complex and it could assist in nuclear transport (for review, Zupan & Zambryski, *Plant Physiol.* 107: 1041–1047 (1995)). Transgenic plants expressing the VirE2 gene are able to complement VirE mutants of Agrobacterium, providing evidence that the VirE2 protein plays an important role in the plant cell (for review, see Zupan & Zambryski, *Plant Physiol.* 107: 1041–1047 (1995)).

VirC: As used herein "VirC" is used to refer to the VirC locus of the Ti- and Ri- plasmid which encodes two polypeptides, VirC1 and VirC2 (Yanofsky M. F. & Nester E. W. "Molecular characterization of a host-range-determining locus from *Agrobacterium tumefaciens*", *J. Bacteriol.* 168: 237–243 (1986)). This locus has been shown to enhance T-DNA border nicking in Agrobacterium (Toro N. et al., "Role of the overdrive sequence in T-DNA border cleavage in Agrobacterium",. *Proc. Natl. Acad. Sci* (USA) 85 (22): 8558–8562 (1988)). VirC1 has also been shown to enhance T-strand production in a heterologous *E.coli* system only when the products of VirD1 and VirD2 genes are limiting (De Vos G. & Zambryski P. "Expression of Agrobacterium nopaline specific VirD1, VirD2 and VirC1 and their requirement for T-strand production in *E. coli*". *Molec. Plant Microbe Inter.* 2: 42–52 (1989)). Although VirC1 has been shown to interact with octopine overdrive sequences by DNA affinity chromatography, the exact function of VirC 1 is unknown. It may associate with VirD1 and VirD2 or with the border repeat and/or at the overdrive sequence to promote nicking and T-strand production (Toro N. et al., "The *Agrobacterium tumefaciens* vir C1 gene product binds to overdrive, a T-DNA transfer enhancer" *J. Bacteriol.* 171: 6845–6849 (1989)).

T-DNA Borders: As used herein "T-DNA borders" is intended to refer to ca. 25-bp imperfect direct repeat DNA sequences which, by virtue of their presence at both ends of a DNA fragment, cause the fragment to be recognized as a T-DNA and acted upon by Agrobacterium proteins. The T-DNA borders occurring at either end of the T-DNA are designated by convention as "left" and "right". The consensus sequence for the right border is 5'GXXTGXCAG-GATATATXXXXXXGTXAX3' (SEQ ID NO:1) and the consensus sequence for the left border is 5'GGTGGCAG-GATATATXXXXXTGTAAA3' (SEQ ID NO:2) (Jouanin et al., *Plant Mol. Biol.* 12:75–85 (1989)). Any DNA between these borders is transferred from Agrobacterium to the plant cell (for review Zambryski P. C., "Chronicles from the Agrobacterium-plant cell DNA transfer story", *Ann. Rev. Plant Physiol.* 43: 465–490 (1992)).

Studies of the T-DNA content of different transformed plant lines has revealed that the integration of T-DNA into the plant genome often takes place at (for the right border) or near (for the left border) these border repeats (Slightom et al., *EMBO J.* 4: 3069–3077 (1985); Gheysen et al., *Genes & Dev.* 5:,287–297 (1991); Mayerhofer et al., *EMBO J.* 10: 697–704 (1991); Ohta et al., *Plant J.* 7: 157–164 (1995); Koncz et al., *Proc. Natl. Acad. Sci.* 86: 8467–8471(1989)).

Despite the structural similarities between left and right borders, studies of border functions have shown that T-DNA borders are differentially utilized. Deletion or inversion of the right border sequence results in an almost complete loss of T-DNA transfer, whereas deletion of the left border repeat has almost no effect (Shaw C. H. et al. "The right hand copy of the nopaline Ti plasmid 25 bp repeat is required for tumor formation" *Nucleic Acids Res.* 12: 6031–6041 (1984); Jen G. C. & Chilton M-D, "The right border region of pTiT37 T-DNA is intrinsically more active than the left border in promoting T-DNA transformation" *Proc. Natl. Acad. Sci* (USA) 83: 3895–3899 (1986)). Genetic analyses show that T-DNA transfer is polar, with polarity determined by the orientation of the border repeats (Wang et al., *Cell* 38: 455–462 (1984); Peralta and Ream, *Proc. Natl. Acad. Sci.* 82: 5112–5116 (1985)). This is probably due to the fact that the T-strand is produced in a right-to-left- direction (Albright et al., "Processing of the T-DNA of *Agrobacterium tumefaciens* generates border nicks and linear, single-stranded T-DNA" *J. Bacteriol.* 16, 1046–1055(1987)).

The sequence context of the T-DNA borders greatly influences their activity. Sequences surrounding the right border enhance, and sequences surrounding the left border attenuate polar DNA transfer (Wang K. et al., "Sequence context of the T-DNA border repeat element determines its relative activity during T-DNA transfer to plant cells" *Mol. Gen. Genet.* 210: 338–346 (1987)). A cis-active sequence of 24 bp, called "overdrive", is present next to the right border of the octopine plasmid (Peralta et al., *EMBO J.* 5:1137–1142 (1986); Shurviton & Ream, *J. Bacteriol.* 173: 5558–5563(1991). Overdrive stimulates T-DNA transfer even when located several thousand base pairs away from the border (Van Haaren M. J. J. et al., "Overdrive is a T-region transfer enhancer which stimulates T-strand production in *A. tumefaciens*" *Nucleic Acids Res.* 15: 8983–8997 (1987)). However, it cannot mediate T-DNA transfer by itself (Peralta, E. G. et al., "overdrive", a T-DNA transmission enhancer on the Agrobacterium tumefaciens tumor-inducing plasmid" *EMBO J.* 5: 1137–1142 (1986); Van Haaren M. J. J. et al., "Functional analysis of the *Agrobacterium tumefaciens* octopine Ti-plasmid left and right T-region border fragment". *Plant Mol. Biol.* 8: 95–104 (1987)). The overdrive sequence was originally localized in a region to the right of the octopine Ti plasmid TL-DNA right border repeat. Similar sequences are present next to the right border repeat of the octopine pTi TR-region and of the agropine pRi TL- and TR-regions (Slightom et al., "Nucleotide sequence analysis of TL-DNA *Agrobacterium rhizogenes* type plasmid. Identification of open reading frames". *J. Biol. Chem.* 261: 108–121 (1986); Jouanin et al., "Analysis of TR-DNA/plant junctions in the genome of a *Convolvulus arvensis* clone transformed with *Agrobacterium rhizogenes* strain A4". *Plant Mol. Biol.* 12: 75–85 (1989)). Comparison of sequences in the vicinity of the right border revealed a region of 8 bp called core sequence (5'TGTTTGTT3') (SEQ ID NO:3) appearing at different distances to the right of each right border repeat. The mannopine-type pRi8196 T-DNA right border does not contain any sequence related to the overdrive sequence but contains a different 8 bp sequence (5'ATTAGTTC3') (SEQ ID NO:4), 6 times repeated (Hansen G. et al., "*Agrobacterium rhizogenes* pRi8196 T-DNA: Mapping and DNA sequence of functions involved in manopine synthesis and hairy root differentiation" *Proc. Natl. Acad. Sci* (USA) 88: 7763–7767 (1991)). This sequence is indeed functionally equivalent to the overdrive (Hansen G. et al. "A T-DNA transfer enhancer sequence in the vicinity of the right border of *Agrobacterium rhizogenes* pRi8196". *Plant Mol Biol* 20: 113–122 (1992)). There is no sequence that closely resembles the overdrive sequence near nopaline T-DNA borders (Wang K. et al., "Sequence context of the T-DNA border repeat element determines its relative activity during T-DNA transfer to plant cells" *Mol. Gen. Genet.* 210: 338–346 (1987)) but this does not exclude that some sequence present in this region plays an analogous role.

The 25-bp right border sequence used in the examples derives from pTiAch5 (Van Haaren, M. J. J., *Plant Mol. Biol.* 13: 523–531 (1989)). The left border present on plasmid pNeoRBluc derives from pTiT37 (Bevan, *Nucleic Acids Res.* 12: 8711–8721 (1984)).

Although it has been shown that sequences adjacent to the right border can enhance the transfer of DNA to the plant cell, a minimal length of right border sequence was chosen in experiments described in the examples in order to minimize possible disruption of the expression of the luciferase gene. Longer right border sequences that contain enhancer like sequence such as an overdrive could be used.

DETAILED DESCRIPTION OF THE INVENTION

Many proteins are known that promote stable integrative transformation of eukaryotic cells with exogenous DNA when produced outside the eukaryotic cell and delivered in combination with the exogenous DNA. The present invention is based upon the discovery that such proteins do not have to be produced and associated with the exogenous DNA outside the eukaryotic cell, as they are naturally, in order to promote stable integrative transformation. Instead, delivery to the eukaryotic transformation target cell of a translatable RNA or a chimeric gene expressible in the eukaryotic cell, which encodes such a protein, can also effectively promote stable integrative transformation of co-delivered exogenous DNA.

According to the method of the present invention, the following components are provided to the eukaryotic cell targeted for transformation:

(a) an exogenous DNA fragment; and (b) at least one chimeric gene or RNA, each such chimeric gene or RNA being capable of producing in the eukaryotic cell a protein that promotes, either alone or in combination with other such proteins, the stable integration of the exogenous DNA fragment in intact form.

The exogenous DNA fragment targeted for integration according to the invention may be any DNA fragment that the skilled artisan desires to have integrated in intact form into the eukaryotic cell genome, such as a chimeric gene designed to express a particular biologically active RNA (e.g. antisense RNA or ribozyme) or protein of interest in the eukaryotic cell, resulting eukaryotic organism, or eukaryotic cell culture.

As the examples illustrate, chimeric genes capable of producing, in a eukaryotic cell, a protein that promotes integration can be constructed using standard genetic engineering techniques. Such a chimeric gene will consist of a DNA sequence coding for the protein operably linked to the appropriate regulatory signals (e.g. promoter, leader sequence, transcription terminator, polyadenylation site) which direct expression of the operably linked coding sequence in the eukaryotic cell. Such coding sequences and regulatory signals are readily available in the art. For example, in plants, preferred promoters that are expressed constitutively include the CaMV 35S and 19S promoters, promoters from genes encoding actin or ubiquitin, and promoters from other genes described in U.S. application Ser. No. 08/258,261, which is hereby incorporated by reference. Examples of preferred chemically inducible promoters, such as the tobacco PR-1a promoter, are detailed in the published application EP 0 332 104 (to Ciba-Geigy) and pending application 08/181,271 (incorporated herein by reference). Another preferred category of promoters is that which is wound inducible. Preferred promoters of this kind include those described by Stanford et al. Mol. Gen. Genet. 215: 200–208 (1989), Xu et al. Plant Molec. Biol. 22: 573–588 (1993), Logemann et al. Plant Cell 1: 151–158 (1989), Rohrmeier & Lehle, Plant Molec. Biol. 22: 783–792 (1993), Firek et al. Plant Molec. Biol. 22: 129–142 (1993), and Warner et al. Plant J. 3: 191–201 (1993). Still more preferred plant promoters include green tissue specific, root specific, stem specific, and flower specific promoters. See, e.g., Hudspeth & Grula, Plant Molec. Biol. 12: 579–589 (1989); de Framond FEBS 290: 103–106 (1991) (EP 0 452 269 to Ciba-Geigy); and WO 93/07278 (to Ciba-Geigy).

In addition, to improve expression of the integration-promoting protein, a synthetic version of the coding sequence optimized for expression in the target eukaryotic cell may be used. For example, the transgenic expression in plants of genes derived from microbial sources may require the modification of those genes to achieve and optimize their expression in plants. In particular, bacterial ORFs that encode separate enzymes but which are encoded by the same transcript in the native microbe are best expressed in plants on separate transcripts. See, e.g. U.S. application Ser. No. 08/258,261, supra.

mRNA capable of producing, in a eukaryotic cell, a protein which promotes integration can be prepared using standard systems for preparing translatable capped poly-A mRNA transcripts encoding a desired protein as the examples illustrate or by other means known in the art.

It will be readily apparent to the skilled artisan that the exogenous DNA and chimeric gene(s) or RNA(s) encoding protein(s) that promote stable integration of the exogenous DNA may be provided to the eukaryotic cell in a variety of ways using standard techniques available in the art. The exact manner in which these components are delivered to the eukaryotic cell is not critical, so long as the protein(s) which promote stable integration of the exogenous DNA are produced in the same cell with the exogenous DNA fragment during the relevant time period as described below.

To achieve the beneficial effect of promoting stable integration of the exogenous DNA fragment in intact form, it is not necessary for the proteins providing this effect to be produced in the eukaryotic cell either before the exogenous DNA fragment is provided to the eukaryotic cell or after the exogenous DNA has been integrated into the eukaryotic cell. Instead it is only necessary for these proteins to be produced in the eukaryotic cell so that they are present in sufficient amounts during the transient period after the exogenous DNA fragment is provided to the eukaryotic cell and before the exogenous DNA has been integrated. Any approach that provides a chimeric gene or translatable RNA to the eukaryotic cell such that the encoded protein is produced during this relevant time period may be used.

As the examples provided herein illustrate, one way to achieve production of sufficient amounts of these proteins during the relevant time frame is to introduce the chimeric gene or translatable RNA encoding the protein to the eukaryotic cell together with the exogenous DNA fragment (i.e. simultaneous delivery of the components). This approach may be preferable because it involves a single delivery of nucleic acid molecules (DNA or DNA and RNA) to the eukaryotic cell targeted for transformation. Another potential beneficial aspect of this approach is that it can be used to achieve transient production of the integration-promoting protein during the relevant time period, rather than stable production which might adversely affect the normal growth and development of the eukaryotic cell.

In one exemplified aspect, the present invention is used to achieve stable transformation of a plant cell with an intact exogenous DNA fragment bounded by T-DNA borders, a result that mimics Agrobacterium-mediated T-DNA transformation. According to this aspect of the invention, the following components are provided to the plant cell targeted for transformation:

(a) the exogenous DNA fragment desired to be integrated into the plant cell genome, said fragment being bounded by one or more T-DNA borders (a single T-DNA border may be sufficient to effect T-DNA transfer, particularly of a circular T-DNA where one border can serve both right and left border functions); and (b) at least one chimeric gene or RNA, each such chimeric gene or RNA being capable of producing in the plant cell an Agrobacterium-derived or similar protein which promotes, either alone or in combination with other such proteins, the stable integration of the exogenous DNA fragment in intact form.

The Agrobacterium-derived protein which is produced in the plant cell or other eukaryotic cell according to this aspect of the invention includes, but is not limited to, proteins derived from the virulence region of the Ti or Ri plasmid of an Agrobacterium. In particular this includes VirC1, VirC2, VirD1, VirD2, and VirE2. Preferably, the protein(s) produced are VirD2 protein or a combination of VirD2 with either VirD1, VirE2, or both VirD1 and VirE2. Expression of the Agrobacterium-derived protein(s) in the cell causes the integration of the exogenous DNA as an intact fragment with predictable endpoints. The resulting transformed cell has an exogenous DNA fragment resembling a T-DNA of Agrobacterium integrated into its genome.

Chimeric genes capable of producing an Agrobacterium-derived protein of the invention in a plant cell or other eukaryotic cell can be constructed using standard genetic engineering techniques such as, but not limited to, those illustrated in the examples. Such a chimeric gene will preferably consist of a DNA sequence coding for the Agrobacterium-derived protein operably linked to the appropriate regulatory signals (e.g. promoter, leader, transcription terminator, polyadenylation site) which direct expression of the operably linked coding sequence in the cell. Such coding sequences and regulatory signals are readily available in the art. The VirD1 and VirD2 coding sequences used in the examples are provided in GenBank as accession No. M14762. RNA capable of producing an Agrobacterium-derived protein of the invention in a eukaryotic cell such as a plant cell can be prepared using standard systems for preparing translatable capped poly-A mRNA transcripts encoding a desired protein as the examples illustrate.

In addition, other vir genes such as those from other Agrobacteria or Rhizobiaceae could be used. (In Addition), accumulated data suggests that a close relationship exists between T-DNA transfer from Agrobacterium to plants and plasmid-mediated bacterial conjugation. Sequence relationships have been found between (i) the nick regions of T-borders and the incP transfer origin; (ii) gene clusters of the virD operon and relaxase operon (TraI/TraJ). TraI and VirD2 as well as their targets-the RP4 oriT nick region and T-border repeats, respectively—share significant similarities (see international patent publication no. WO 88/03564 entitled "Plant Transformation"). In vitro, TraI and VirD2 are each sufficient to produce nicks in single-stranded oligonucleotides bearing their respective cognate nick sites (see Pansegrau et al., *Proc. Natl. Acad. Sci.* (USA) 90:11538–11542 (1993)). In the presence of an excess of cleavage products, both TraI and VirD2 can also catalyze the opposite reaction, joining two pieces of single-stranded DNA. VirD2 is also able to catalyze the cleavage of oriT. Functional similarities have also been found between the geminivirus Rep proteins or proteins involved in rolling circle replication of bacterial phages and plasmids and, on the other hand, proteins participating in bacterial conjugative DNA transfer or in the transfer and integration of the T-DNA from Agrobacterium into the plant genome (Heyraud-Nitschke F, et al. *Nucl. Acids Res.* 910–916 (1995)).

The exogenous DNA fragment which is targeted for integration according to this aspect of the invention may be any DNA fragment which the skilled artisan desires to have integrated in intact form into the cell genome, such as a chimeric gene designed to express a particular biologically active RNA (e.g. antisense RNA or ribozyme) or protein of interest in the cell or resulting organism or cell culture. The only requirement is that the fragment be bounded by one or more T-DNA borders such that it can be recognized and acted upon by the VirD1 and VirD2 proteins. An example of the attachment of such T-DNA borders to an exogenous DNA fragment is described in Example 1.

Any eukaryote which is susceptible to delivery of nucleic acids by any one or more of the various mechanisms available in the art may be used as the target for transformation according to the present invention. This includes fungi, yeast, insect cells, fish and other animal cells and embryos, and particularly plant cells. For yeast, transfer of T-DNA has been shown. See, for example, Piers et al., *Proc. Natl. Acad. Sci.* 93: 1613–1618 (1996); and Bundock et al., *EMBO J.* 14: 3206–3214 (1995). For animal cells, localization of VirD2 and VirE2 (after modification of its localization signals) into cell nuclei has been shown. see Guralnick et al., *Plant Cell* 8: 363–373 (1996). Thus, the invention would be optimized for use in other eukaryotes by the modification of the localization signals. The codon preferences of the genes may also be modified by means known in the art to ensure maximal expression. Methods for delivering nucleic acids to various animal cells are well known in the art (see, e.g. "Current Protocols in Molecular Biology", vols. 1–3, ed. by Ausubel, F. M. et al., pub. by John Wily & Sons, Inc. (1995); see, in particular, Chapter 9, "Introduction of DNA into Mammalian Cells"). Potential animal targets include, but are not limited to, the gametes, ova, zygotes, and fertilized ova of sheep, goats, cattle, swine, mice, rats, and cultured animal cell lines.

Potential plant targets include both monocotyledonous and dicotyledonous plants, particularly agronomically important crop plants such as maize and other cereal crops such as wheat, oats, rye, sorghum, rice, barley, millet, turf and forage grasses, and the like, as well as cotton, sugar cane, sugar beet, oilseed rape, bananas, poplar, walnut and soybeans. Other potential plant targets include gymnosperms such as loblolly pine, cedar, and spruce. Any type or source of plant cells which can serve as a target for transformation by any one or more of the various biological and non-biological delivery mechanisms available in the art can also serve as a target for transformation according to the present invention. This includes, but is not necessarily limited to, immature and mature embryos, pollen, protoplasts, suspension culture cells, callus cells, cotyledon or other seed and seedling parts, and leaves or leaf pieces.

Transformed eukaryotic cells obtained by the method of the invention will typically contain an integrated intact exogenous DNA. This integrated exogenous DNA may include partial T-DNA border sequences typically retained on integrated DNA following a T-DNA insertion event. Alternately, the integrated exogenous DNA may show some truncation of the left end of the T-DNA or occasionally of some DNA beyond the left border, as has been observed after transformation with Agrobacterium. Transformed eukaryotic cells obtained by the method of the invention may be used to produce transgenic cell cultures and fertile transgenic organisms according to standard procedures well known in the art.

For example, to breed progeny from plants transformed according to the method of the present invention, a method such as that which follows may be used: maize plants produced as described in the examples set forth below are grown in pots in a greenhouse or in soil, as is known in the art, and permitted to flower. Pollen is obtained from the mature tassel and used to pollinate the ears of the same plant, sibling plants, or any desirable maize plant. Similarly, the ear developing on the transformed plant may be pollinated by pollen obtained from the same plant, sibling plants, or any desirable maize plant. Transformed progeny obtained by this method may be distinguished from non-transformed progeny by the presence of the introduced gene(s) and/or accompanying DNA (genotype), or the phenotype conferred. The transformed progeny may similarly be selfed or crossed to other plants, as is normally done with any plant carrying a desirable trait. Similarly, tobacco or other transformed plants produced by this method may be selfed or crossed as is known in the art in order to produce progeny with desired characteristics. Similarly, other transgenic organisms produced by a combination of the methods known in the art and this invention may be bred as is known in the art in order to produce progeny with desired characteristics.

It will be readily apparent to the skilled artisan that the components of this method (i.e. the exogenous DNA and the chimeric genes or RNA's encoding proteins which promote integration of the exogenous DNA) may be provided to the eukaryotic cell in a variety of ways using standard techniques available in the art. The exact manner in which these components are provided to the cell is not critical, so long as the protein(s) which promote stable integration of the exogenous DNA are produced during the relevant time period as described above.

The exact amount of each component provided to the eukaryotic cell is likewise not critical and may vary depending on the manner and form in which the component is delivered. If desired, the skilled artisan may routinely vary the amount of each component provided to determine the optimum level for each using a particular delivery system. For plant transformation, one successful combination is described in Example 1 and can serve as a starting point for further optimization.

Delivery of the components of this method to the eukaryotic cell may be accomplished by a variety of techniques available in the art for delivering nucleic acids to cells including, but not necessarily limited to, non-biological mechanisms such as microprojectile bombardment, electroporation, microinjection, induced uptake, and aerosol beam injection.

Various transformation methods included here for enabling purposes are disclosed in U.S. patent application Ser. No. 08/181,271, which is hereby incorporated by reference. Such methods used for transfer of DNA into eukaryotic cells such as plant cells include, for example, direct DNA uptake, liposomes, electroporation, micro-injection, and microprojectiles. See, for example, Bilang, et al., *Gene* 100: 247–250 (1991); Scheid et al., *Mol. Gen. Genet.* 228: 104–112 (1991); Guerche et al., *Plant Science* 52: 111–116 (1987); Neuhause et al., *Theor. Appl Genet.* 75: 30–36 (1987); Klein et al., *Nature* 327: 70–73 (1987); Howell et al., *Science* 208: 1265 (1980); Horsch et al., *Science* 227: 1229–1231 (1985); DeBlock et al., *Plant Physiology* 91: 694–701 (1989); *Methods for Plant Molecular Biology* (Weissbach and Weissbach, eds.) Academic Press Inc. (1988); and *Methods in Plant Molecular Biology* (Schuler and Zielinski, eds.) Academic Press Inc. (1989). See also, U.S. Pat. Nos. 4,945,050; 5,036,006; and 5,100,792, all to Sanford et al. In addition, see U.S. patent application Ser. Nos. 08/438,666, filed May 10, 1995, and 07/951,715, filed Sep. 25, 1992, both of which are hereby incorporated by reference in their entireties.

Various techniques known to those skilled in the art relating to the transformation of animal cells and insects are set forth in the following references: Wall et al., *Transgenic Research* 5(1):67–72 (1996); Rexroad et al., *Anim. Biotech.* 1:1–10 (1990); Hogan et al., Manipulating the Mouse Embryo: a Laboratory Manual. Cold Spring Harbor, N.Y.: Cold Spring Harbor Laboratory Press (1986); Shanahan et al., *Mol. Cell. Biol.* 9:5473–9 (1989); Alam et al., *Transgenic Research* 5:87–95 (1996) and references therein; Mitchell, M. F. *Amer. J. Obstet.* 174:1094–11 (1996); Keller, E. T., *The Cancer Gene* 3:186–191 (1996); Lo, D., *Clin. Immunol. Im.* 79:96–104 (1996); Brousseau, M. E., *J. Clin. Invest.* 97:1844–185 (1996); Kim, C. H., *Neurochem. Res.* 21:231–237 (1996); Kroshus, T. J., Cd59 *Transplantation* 61:1513–152 (1996); Cozzi, E., *Xenotransplanta* 3:128–133 (1996); Dziadek, M., T. *Aust. Vet. J.* 73:182–187 (1996); Damak, S., *Bio-Technology* 14:185–188 (1996); Shen, J. H., *Faseb. J.* 9:1623–1631 (1995); Wall, R. J., *Theriogenology* 45:57–68 (1996); Simoens, C., *P. Hum. Reprod. Upda.* 1:523–542 (1995); Wagner, J., *Pediat. Nephrol.* 10:108–35 U.S.C. §112, (1996); Duncker et al., *Transgenic Research* 5:49–55 (1996); Duncker, B. P., *Cryobiology* 32:521–527 (1995).

In a preferred approach, a single procedure is used to deliver all the components of this method (i.e. the exogenous DNA and the chimeric genes or RNA's encoding proteins which promote integration of the exogenous DNA) to the recipient eukaryotic cell.

mRNA encoding an integration-promoting protein, delivered according to the invention, is expected to produce the encoded protein in the transformed eukaryotic cell for a finite period before it is degraded. The protein produced from this mRNA is expected to remain in the cell for a finite period of time before it too is degraded through normal cellular processes. Thus these proteins may be delivered transiently to the cell in the form of RNA according to the method of the invention. Transient delivery of these proteins may be preferred in those situations where the continued presence of such proteins may have deleterious effects. This same effect can be achieved by delivering a chimeric gene encoding an integration-promoting protein in a form which cannot readily integrate into the cell genome in a functional form.

In cases where the integration-promoting proteins are provided to the cell via a chimeric gene, the respective chimeric genes are preferably co-delivered along with the exogenous DNA fragment as separate DNA molecules, though they may be combined and delivered as a single DNA molecule. Delivery as separate DNA molecules allows the ratio of chimeric gene to exogenous DNA fragment to be varied and optimized. It is also likely to be more convenient to engineer these constructs on separate molecules.

Stable incorporation of such chimeric genes into the genome via random integration may be expected to occur at a measurable frequency relative to the directed integration of the exogenous DNA bounded by T-DNA borders. To facilitate separation of such random integration events from the directed integration of the exogenous DNA, the chimeric genes encoding the integration-promoting proteins may preferably be delivered as a single DNA molecule separate from the exogenous DNA. Using this approach, copies of the chimeric genes are likely to be integrated at a different locus from the directed integration of the exogenous DNA bounded by T-DNA borders. As a result, separation of the directed integration events involving the exogenous DNA from the randomly integrated VirD1 and VirD2 genes by subsequent breeding of organisms derived from the transformed eukaryotic cells is easily accomplished.

In another embodiment, a viral vector is used as the vehicle for delivering the chimeric gene or RNA encoding the integration-promoting protein to a eukaryotic cell. In a preferred embodiment of this aspect of the invention, a plant viral vector is used as the vehicle for delivering the chimeric gene or RNA encoding the integration-promoting protein to a plant cell. Such vectors may be engineered from plant DNA virus replicons, such as geminivirus replicons,(Ugaki, M., *Nucleic Acids Research* 19: 371–377 (1994)) and RNA virus vectors (Sablowski, R. W., *Proc. Natl. Acad. Sci.* 92: 6901–6907 (1995)) for incorporation and expression of a desired DNA or RNA in a plant cell. Since these viral vectors typically replicate in the target cell, amplification of the chimeric gene or RNA engineered into such vectors, and increase in the protein produced therefrom, is achieved. Also, viral vectors of this type are not expected to integrate into the genome of the cell because the viral replicons they are derived from do not normally do so. Thus this method has the advantages of transiently producing large amounts of the integration-promoting proteins while reducing the risk of integration of chimeric genes encoding such proteins. It may also be advantageous to use such viral vectors systemically to infect, in advance, plant cells or other eukaryotic cells targeted for transformation. This approach allows delivery of the exogenous DNA desired to be integrated in higher amounts by avoiding the need to co-deliver DNA or RNA encoding the integration-promoting protein or proteins.

A viral vector such as a plant viral vector can also be used as the vehicle for delivering the exogenous DNA fragment targeted for integration to the plant cell or other eukaryotic cell. Since these vectors typically replicate in the target cell, their use in this manner amplifies the number of exogenous DNA fragment templates available for integration.

When a viral vector is used to deliver both the exogenous DNA fragment targeted for integration and the chimeric gene encoding the integration-promoting protein to the targeted cell, the same viral vector may be used to deliver both components or two separate viral vectors may be used. When Agrobacterium-mediated transformation is the technique used to deliver the viral vector(s) to the targeted plant, the approach utilizes "agroinfection" (see Grimsley et al. *Nature* 325: 177–179 (1987)).

As an alternative to co-delivery of the chimeric genes encoding integration-promoting proteins with the exogenous DNA, the exogenous DNA may be delivered to a transgenic eukaryotic cell such as a plant cell already containing these chimeric genes stably incorporated into its genome. Transgenic organisms or transgenic cell cultures generated by transformation using standard techniques with DNA molecules including chimeric genes encoding integration-promoting proteins may be used as the source for such transgenic cells. Using this approach, directed integration events involving the exogenous DNA may be separated from the stably integrated chimeric genes by subsequent breeding of organisms derived from the transformed cells (see, e.g. Peerbolte, R. et al., "Transformation of plant protoplasts with DNA: cotransformation of non-selected calf thymus carrier DNA and meiotic segregation of transforming DNA sequences", *Plant. Mol. Biol.* 5 (4): 235–246 (1985)).

While the present invention is described herein in terms of the transformation of a single cell, the skilled artisan will appreciate that the delivery methods upon which the invention is based are typically applied to a population of cells in the form of a cell culture, callus, protoplasts, embryos, or tissue excised from a whole organism. As a result, a variety of techniques have been developed for use in conjunction with these delivery methods to identify and/or select stably transformed cells from a mixed population of transformed and untransformed cells (e.g. Dekeyser, R. et al., "Evaluation of selectable markers for rice transformation", *Plant Physiol.* 90 (1): 217–223 (1989)). These techniques may also be used in conjunction with the present invention in the same manner.

With respect to the exogenous DNA component, transformation of eukaryotic cells according to the method of the present invention using non-biological delivery methods is contemplated to result in two basic types of integration events: (1) simple insertion of the intact exogenous DNA fragment bounded by T-DNA borders directed by the presence of protein(s) promoting such integration events, and (2) random insertion of various portions and permutations of the exogenous DNA characteristic of the non-biological delivery method used. These two types of integration events may be readily distinguished by applying standard molecular analytical tools to the genomic DNA of the transformed cells such as Southern blot hybridization of restricted genomic DNA using the exogenous DNA fragment or subfragments thereof as a probe, polymerase chain reaction (PCR) based techniques designed to detect the presence of the exogenous DNA fragment in intact form. For cells that contain both types of insertion events, such events may be separated in transgenic organisms derived therefrom by traditional breeding approaches. Using these tools, transgenic cells or organisms arising from application of the present invention, which have a simple insertion of the intact exogenous DNA fragment originally bounded by T-DNA borders, may be identified and used to generate transgenic cell cultures and/or transgenic organisms and progeny.

It should be understood that the present invention is not limited to improved integration systems based on the Agrobacterium T-DNA transfer system. As explained above, additional systems which utilize integration-promoting proteins and recognition sequences analogous to the Vir proteins and T-DNA borders, such as those from other Agrobacteria or Rhizobiaceae, may be modified according to the present invention to improve the frequency of simple integration events in a eukaryotic cell targeted for transformation.

EXAMPLES

Standard recombinant DNA and molecular cloning techniques used here are well known in the art and are described by J. Sambrook, E. F. Fritsch and T. Maniatis, *Molecular Cloning: A Laboratory manual*, Cold Spring Harbor laboratory, Cold Spring Harbor, N.Y. (1989) and by T. J. Silhavy, M. L. Berman, and L. W. Enquist, *Experiments with Gene Fusions*, Cold Spring Harbor Laboratory, Cold Spring Harbor, N.Y. (1984).

BIBLIOGRAPHY OF REFERENCES CITED IN THE EXAMPLES

Ahl Goy, P. & Duesing J. H. (1995) *Bio/Technology* 13, 454–458.

Albert, H., Dale, E. C., Lee, E. & Ow, D. W. (1995) *Plant J.* 7, 649–659.

Albright, L. M., Yanosky, M. F. Leroux, B., Ma D., & Nester, E. W. (1987) *J. Bacteriol.* 169, 1046–1055.

An, G. (1985) *Plant Physiol.* 79, 568–570.

Bevan, M. (1984) *Nucleic Acids Res.* 12, 8711–8721.

Callis, J., Fromm, M. E., Walbot, V. (1987) *Genes & Dev.* 1, 1183–1200.

Chilton M-D. (1993) *Proc. Natl. Acad. Sci.* (USA) 90, 3119–3120.

Chu, C. C., Wang, C. C. Sun, C. S. Hsu, C., Yin, K. G., Chu, C. Y. & Bi, F. Y. (1975) *Sci. Sin.* 18, 659–668.

Chyi, Y. S., Jorgensen, R. A., Golstein, D., Tanksley, S. D. & Loaiza-Figueroa, F. (1986) *Mol. Gen. Genet.* 204, 64–69.

Citovsky V., Warnick, D. & Zambryski, P. (1994) *Proc. Natl. Acad. Sci.* (USA) 91, 3210–3214.

deWet, J. R, Wood, K. V., DeLuca, M., Helsinki, D. R., and Subramani, S. (1987), "Firefly luciferase gene: Structure and expression in mammalian cells", *Mol. Cell. Biol.* 7: 725–737

DiMaio, J. J. & Shillito, R. D. (1992) *J. Tissue Cult. Methods* 12, 163–169.

Dowson Day, M. J., Ashurst, J. L., Mathias, S. F., Watts, J. W., Wilson T. M. A., & Dixon, R. A. (1993) *Plant Mol.Biol.* 23, 97–109.

Durrenberger, F., Crameri, A., Hohn, B., & Koukolikova-Nicola, Z. (1989) *Proc. Natl. Acad. Sci.* (USA) 86, 9154–9158.

Filichkin, S. A. & Gelvin, S. B. (1993) *Mol. Microbiol.* 8, 915–926.

Fukushige, S. & Sauer, B. (1992) *Proc. Natl. Acad. Sci.* (USA) 89, 7905–7909.

Gallie, D. R., Lucas, W. J. & Walbot, V. (1989) *Plant Cell* 1, 301–311.

Gallie, D. R. (1991) *Genes & Dev.* 5, 2108–2116.

Gallie, D. R. (1993) *Plant Cell reports* 13, 119–122.

Ghai, J. & Das A. (1989) *Proc. Natl. Acad. Sci.* (USA) 8,: 3109–3113.

Gheysen, G., Villaroel, R. & Van Montagu, M. (1991) *Genes & Dev.* 5:,287–297.

Gordon-Kamm, W. J., Spencer, T. M., Mangano, M. L., Adams, T. R., Daines, R. J., Start, W. G., O'Brien, J. V. Chambers, S. A., Adams, R. A., Willets, N. G., Rice, T. B., Mackey, C. J., Krueger, R. W., Kausch, A. P. & Lemaux, P. G. (1990) *Plant Cell* 2, 603–618.

Hall, G., Allen, G. C., Loer, D. S., Thompson, W. F. & Spiker, S. (1991) *Proc. Natl. Acad. Sci.* (USA) 88, 9320–9324.

Herman, L., Jacobs, A., Van Montagu, M., & Depicker, A. (1990) *Mol. Gen. Genet.* 224, 248–256.

Herrera-Estrella, A., Chen, Z., Van Montagu, M., & Wang, K., (1988) *EMBO J.* 7, 4055–4062.

Herrera-Estrella, A., van Montagu, M. & Wang, K. (1990) *Proc. Natl. Acad. Sci.* (USA) 87, 9534–9537.

Higgs, D. C. & Colbert, J. T. (1993) *Plant Cell reports* 12, 445–452.

Howard, E. A., Winsor, B., De Vos, G., & Zambryski, P. (1989) *Proc. Natl. Acad. Sci.* (USA) 86, 4017–4021.

Howard, E. A., Zupan, J. R., Citovsky, V. & Zambryski, P. (1992) *Cell* 68, 109–118.

Jasper, F., Koncz, C., Schell, J. & Steinbiss, H.-H. (1994) *Proc. Natl. Acad. Sci.* (USA) 91, 694–698.

Kado, C. I. (1993) in *Bacterial conjugation*, ed. Clewell, D. B. (Plenum, N.Y.), pp. 243–254.

Kertbundit, S., De Greve, H., Deboeck, F., Van Montagu, M. & Hemalsteens, J.-P. (1991) *Proc. Natl. Acad. Sci.* (USA) 88, 5212–5216.

Klein, T. M., Harper, E. C., Svab, Z., Sanford, J. C., Fromm, M. E. & Maliga, P. (1988) *Proc. Natl. Acad. Sci.* (USA) 85, 8502–8505.

Klein, T. M., Kornstein, L., Sanford, J. C., & Fromm, M. E. (1989) *Plant Physiol.* 91, 440–444.

Koncz, C., Martini, N., Mayerhofer, R., Koncz-Kalman, Zs., Körber, H., Redei, G. P. & Schell, J. (1989) *Proc. Natl. Acad. Sci.* (USA) 86, 8467–8471.

Koukolikova-Nicola, Z., Raineri, D., Stephens, K., Ramos, C., Tinland, B., Nester, E., & Hohn, B. (1993) *J. Bacteriol.* 175, 723–731.

Koziel, M. G., Beland, G. L., Bowman, C., Carozzi, N. B., Crenshaw, R., Crossland, L., Dawson, J., Desai, N., Hill, M., Kadwell, S., Launis, K., Lewis, K., Maddox, D., McPherson, K., Meghji, M. R., Merlin, E., Rhodes, R., Warren, G. W., Wright, M. & Evola, S. V. (1993) *Bio/Technology* 11, 194–200.

Lakso, M. Sauer, B., Mosinger, B., Lee, E. J., Manning, R. W., Yu, S. H., Mulder, K. L. & Westphal, H. (1992) *Proc. Natl. Acad. Sci.* (USA) 89: 6232–6236.

Matsuzaki, H., Araki, H. & Oshima, Y. (1988) *Mol. Cell. Biol.* 8, 955–962.

Matsuzaki, H., Nakajima, R., Nishiyama, J., Araki, H. & Oshima, Y. (1990) *J. Bacteriology* 172, 610–618.

Matzke, M. A. & Matzke, A. J. M. (1995) *Plant Physiol.* 107, 679–685.

Mayerhofer, R., Koncz-Kalman, Z., Nawrath, C., Bakkeren, G., Crameri, A., Angelis, K., Redei, G. P., Schell, J., Hohn. B. & Koncz, C. (1991) *EMBO J.* 10, 697–704.

Morrish F. M. and Fromm M. E. 1992 Current Opinion in Biotechnology 3:141–146.

Murashige, T. & Skoog, F. (1962) *Physiol. Plant* 15, 473–497.

Odell, J. T. & Russell S. H. (1994) in *Homologous Recombination and gene Silencing in Plants*, ed. Paszkowski, J. (Kluwer Academic Publishers) pp. 219–270.

O'Gorman, S., Fox, D. T. & Wahl, G. M. (1991) *Science* 251, 1351–1355.

Ohba, T., Yoshioka, Y., Machida, C. & Machida, Y. (1995) *Plant J.* 7, 157–164.

Ohta, S., Mita, S., Hattori, T. & Nakamura, K. (1990) *Plant Cell Physiol.* 31, 805–813.

Onouchi, H., Yokoi, K., Machida, C., Matsuzaki, H., Oshima, Y., Matsuoka, K., Nakamura, K. & Machida, Y. (1991) *Nucleic Acids Res.* 19, 6373–6378.

Onouchi, H., Nishihama, R., Kudo, M., Machida, Y. & Machida, C. (1995) *Mol. Gen. Genet.* 247, 653–660.

Ow, D. W., Wood, K. V., DeLuca, M., deWet, J. R., Helinski, D. R. & Howell, S. H. (1986) *Science* 234, 856–85.

Pansegrau, W., Schoumacher, F., Hohn, B. & Lanka, E. (1993) *Proc. Natl. Acad. Sci.* (USA) 90, 11538–11542.

Raskin, I. 1996 Proc. Natl. Acad. Sci. USA 93 3164–3166.

Rothstein, S. J., Lahners, K. N., Lotstein, R. J., Carozzi, N. B., Jayne, S. M. & Rice, D. A. (1987) *Gene* 53, 153–161.

Rosenberg, A. H., Lade, B. N., Chui, D-S., Lin, S-W., Dun, J. J., Studier, F. W. (1987) *Gene*, 125–135.

Rossi, L., Hohn, B. & Tinland, B. (1993) *Mol. Gen. Genet.* 239, 345–353.

Russell, S. H., Hoopes, J. L. & Odell, J. T. (1992) *Mol. Gen. Genet.* 234, 49–59. Saunders, K., Lucy, A., and Stanley, J. (1991) *Nucleic Acids Research* 19, 2325–2330.

Shurviton, C. E., Hodges, L. & Ream, W. (1992) *Proc. Natl. Acad. Sci.* (USA) 89, 11837–11841.

Stachel, S. E., Timmermann, B. & Zambryski, P. (1986) Nature (London) 322, 706–712.

Stachel et al., *Proc. Natl. Acad. Sci.* USA 83: 379–383 (1986)

Stachel, S., Timmerman, B., & Zambryski, P. (1987) *EMBO J.* 6, 857–663.

Stenger, D. C. Revington, G. N., Stevenson, M. C., and Bisaro, D, M. (1991) *Proc. Natl. Acad. Sci.* (USA) 88, 8029–8033.

Thompson, C. J. Movva, N. R. Tizard, R., Crameri, R., Davies, J. E. Lauweereys, M. and Botterman, J. (1987) *EMBO J.* 6:2519–2523.

Tinland, B., Koukolikova-Nicola, Z., Hall, M. N. & Hohn, B. (1992) *Proc. Natl. Acad. Sci.* (USA) 89, 8000–8004.

Tinland, B. et al., *Proc. Natl. Acad. Sci.* USA 91: 8000–8004 (1994)

Tinland, B., Schoumacher, F., Gloeckler, V., Bravo Angel, A. M. B. & Hohn, B. (1995) *EMBO J.* 14, 3585–3595.
Ugaki, M., Ueda, T., Timmermans, M. C. P., Vieira, J., Elliston, K. O. and Messing, J. (1991) *Nucleic acids Research* 19, 371–377.
Van Haaren, M. J. J., Sedee, N. J. A., De Boer, H. A., Schilperoort, R. A. & Hooykaas, P. J. J. (1989) *Plant Mol. Biol.* 13, 523–531.
Vasil, V., Castillo, A. M., Fromm, M. E. & Vasil, I. K. (1992) *Bio/Technology* 10, 667–674.
Vogel, A. M. & Das, A. (1992) *J. Bacteriol.* 174, 303–312.
Wallroth, M., et al. *Mol. Gen. Genet.* 202: 6–15 (1986)
Wan, Y. & Lemaux, P. G. (1994) *Plant Physiol.* 104, 37–48.
Wang, K., Stachel, S. E., Timmerman, B., Van Montagu, M., & Zambryski, P. (1987) *Science* 235, 587–591.
Ward, E. R. & Barnes, W. M. (1988) *Science* 242, 927–930.
Winans et al, *Nucl. Acids Res.* (1987) 15:825–837
Yanofsky, M. F., Porter, S. G., Young, C., Albright, L. M., Gordon, M. P. & Nester, E. W. (1986) *Cell* 47, 471–477.
Young, C. & Nester, E. W. (1988) *J. Bacteriol.* 8, 3367–3374.
Yusibov, V. et al., *Proc. Natl. Acad. Sci.* USA 91: 2994–2998 (1994).
Zambryski, P. (1992) *Annu. Rev. Plant Physiol.* 43, 465–490.
Zupan J. R. & Zambryski P. (1995) *Plant Physiol.* 107: 1041–1047

Example 1

"Agrolistic" Transformation of Plant Cells: Integration of T-Strands Generated in Planta After Biolistic Delivery of VirD1 and VirD2 Genes and a T-DNA-Bordered Selectable Marker Gene A. Abstract The virulence genes VirD1 and VirD2 are required for excision of T-strands from the Ti plasmid in Agrobacterium tumefaciens prior to delivery to host plant cells, where T-DNA inserts into plant nuclear DNA. We have employed biolistic delivery of plasmid DNAs to test for binding and/or site-specific nicking of a T-DNA border sequence by VirD1 and VirD2 in planta. Gold microprojectiles were coated with a mixture of 3 plasmids containing, respectively, VirD1 and VirD2 coding regions under the control of the CaMV35S promoter and a test gene containing a right border sequence inserted between the CaMV35S promoter and the luciferase coding region. We measured luciferase transient expression to test for integrity and transcriptional availability of the test gene. In both tobacco and maize cells, luciferase gene transient expression was strongly inhibited by codelivery of VirD1 and VirD2 plasmids. Inhibition was greater when the ratio of VirD plasmids to test gene plasmid was increased. Significant inhibition occurred only with one orientation of the border sequence, i.e. the direction that would lead to VirD2 nicking of the DNA strand that is the template for luciferase mRNA. The effect of VirD1 alone or VirD2 alone was less. Biolistic delivery of a transformation vector with a selectable marker and the luciferase test gene plus the mixture of VirD plasmids produced a moderate frequency of "agrolistic" inserts whose right junctions with plant DNA had precisely the sequence expected for T-DNA insertion events. We found both biolistic and "agrolistic" events in some transformant lines.

B. Introduction

Gene delivery by particle bombardment has become a widely accepted technique with broad applications in plant transformation (reviewed in Ahl Goy and Duesing, 1995). For example, maize resistant to European corn borer has been developed by this technique (Koziel et al, 1993). In the course of product development, the structure and copy number of the transgenes as well as their stability must be established. The most desirable product would be one with a single simple insert and no extraneous plasmid vector DNA. However in plant transformation by particle bombardment, there is a tendency towards integration of multiple copies of the introduced genes including plasmid vector (Klein et al., 1988, Klein et al., 1989; Gordon-Kamm W. J. et al., 1990; Vasil et al., 1992; Wan Y. and Lemaux P, 1994). This procedure appears to promote plasmid concatemerization, either before or during integration. The multiple copies inserted during biolistic transformation generally are genetically linked and cannot be segregated during subsequent breeding.

Multiple copies of transgenes can lead to instability of their expression by several mechanisms (reviewed in Matzke M and Matzke A., 1995): multiple copies of transgenes can interact to inactivate each other and related host genes by epigenetic mechanisms variously labeled "cosuppression" or "gene silencing." In addition, homologous recombination may cause genetic instability of multiple copies. For these reasons, reduction of the copy number of transgenes inserted should prove beneficial for maintaining the fidelity of introduced genes.

The integration pattern for foreign genes introduced via Agrobacterium-mediated transformation is in general strikingly different from that resulting from particle bombardment of plant cells (review, Chilton, 1993). The number of copies of intact and rearranged transgenes resulting from biolistic delivery exceeds, often greatly, the copy number of transgenes introduced into plants by the Agrobacterium system. Agrobacterium has evolved a mechanism in which the transferred genes are located on plasmids, called tumor-inducing (Ti) or root-inducing (Ri) plasmids (reviewed in Kado, 1993). A specific segment called T-DNA (transferred DNA) of Ti or Ri plasmid DNA, which is flanked on the Ti/Ri plasmid by 25-bp directed repeated border sequences, travels from the bacterium to the plant cell nucleus and becomes integrated into the plant's chromosomal DNA. An elaborate mechanism for DNA transfer is encoded by a series of virulence (vir) genes (reviewed in Zambryski, 1992). Activation of the vir genes results in the generation of site-specific nicks within the T-DNA border repeats and produces a linear single-stranded DNA molecule (T-strand) corresponding to the bottom strand of the T-DNA. Nicking requires two polypeptides encoded by the VirD operon: VirD1 and VirD2 (Stachel and Nester, 1986; Stachel et al., 1987; Herrera-Estrella et al., 1988; DeVos and Zambryski, 1989; Durrenberger et al., 1989; Howard et al., 1989; Koukolikova-Nicola et al., 1993). VirD1 exhibits a DNA-relaxing activity (Ghai and Das, 1990; Filichkin and Gelvin, 1993) while VirD2 has an endonuclease activity that cleaves the lower strand of the border sequence (Stachel et al., 1986; Yanofsky et al., 1986; Wang et al., 1987; Albright et al., 1987). In vitro experiments have also demonstrated that purified VirD2 specifically cleaves single-stranded DNA (Pansegrau et al., 1993; Jasper et al., 1994). Neither supercoiled nor relaxed double-stranded DNA act as substrate for cleavage by VirD2 alone in vitro (Jasper et al., 1994).

VirD2 becomes covalently attached to the 5' end of the nicked DNA (Ward and Barnes, 1988; Young and Nester, 1988; Howard et al., 1989) via tyrosine residue 29 (Durrenberger et al., 1989; Vogel and Das, 1992; Pansegrau et al., 1993). A second cleavage at the left border sequence leads to the liberation of the T-strand. The T-strand is, in addition, coated along its length by a single-strand binding protein, VirE2. VirD2 and VirE2 contain nuclear localization signals (NLSs) that are believed to pilot the T-strand into the plant cell nucleus (Herrera-Estrella, 1990; Howard et al., 1992; Shurviton et al., 1992; Tinland et al., 1992; Rossi et al., 1993). The NLSs of VirD2 and VirE2 are recognized in tobacco and in maize (Citovsky et al., 1994) but their efficiency is dependent on the developmental stage of the tissue. Recent data support the view that VirD2 may participate in the ligation of the 5' end of the T-strand to the plant DNA (Tinland et al., 1995).

In the present study, we have developed a novel plant transformation technique that combines some of the advantages of the Agrobacterium system with the proven high efficiency of the biolistic and other delivery systems for a wide range of crop plants. It is designed to integrate the gene of interest with no vector sequence, as in T-DNA inserts, and to control the copy number. Our approach is to use plant expression cassettes for VirD1 and VirD2 genes codelivered with a transforming plasmid containing T-DNA border sequences flanking a selectable marker. We have found that the transiently expressed VirD1 and VirD2 gene products can indeed cleave T-DNA border sequences in planta and produce T-DNA-type insertion events ("agrolistic" events) after biolistic delivery.

C. Materials and Methods

1. Plasmids

Structures of all plasmid inserts used in this Example are presented in FIG. 1. pCIB1711 is a pUC derivative containing the firefly luciferase gene driven by the cauliflower mosaic virus 35S (CaMV35S) promoter.

Construction of pCIB1711 pCIB1711 contains a luciferase gene linked to 35S expression signals. The parent vector pCIB710 (Rothstein et al. 1987) was modified prior to insertion of the luciferase gene by removing unique restriction sites PstI and NarI. The PstI site located upstream of the CaMV promoter was removed by cleavage at adjacent SalI and SphI restriction sites and ligation of synthetic linker [TCGACATG] (SEQ ID NO:5) to recreate the SalI site and remove the SphI and PstI sites. The NarI site located 3' to the CaMV polyadenylation sequences was removed by cleavage with NarI and NdeI, excising a 52 bp fragment, followed by klenow digestion and blunt end ligation. Plasmids pJD204 (Ow et al., Science 234: 856–859 (1986)) and pDO0432 (De Wet et al., Mol. Cell. Biol. 7(2): 725–737 (1987)) were obtained from Dr. Donald Helinski and Dr. Steve Howell, respectively. A 1826 bp HindIII-bamHI fragment from pJD204 containing the luciferase gene, 22 bp of the luciferase 5' UTL, and about 130 bp of the 3' end was ligated with a synthetic linker made from the oligos [GATCCCTGCAGA] (SEQ ID NO:6) and [AGCTTCTGCAGG] (SEQ ID NO:7) into the BamHI site of pCIB710 so as to be between the 35S promoter and polyadenylation signals.

Insertion of the luciferase gene fragment into the modified pCIB710 vector produced pCIB1701. pCIB1711 was constructed by digesting pCIB1701 with PstI and NarI, and ligation of the resulting plasmid with a linker R5B1 containing the leader and 5' end of the gene.

Linker R5B1 consists of an fragment made from the following complimentary oligomers:

(SEQ ID NO:8)
5'ATCTCCACTGACGTAAGGGATGACGCACAATCCCACTATCCTTCGCA
AGACCCTTCCTCTATATAAGGAAGTTCATTTCATTTGGAGAGGGATCCCT
GCAGGACACGCTGAAATCACCAGTCTCTCTCTACAAATCTATCTCTCTC
TATG3'.

and (SEQ ID NO:9)
5'GATCCATAGAGAGAGATAGATTTGTAGAGAGAGACTGGTGATTTCA
GCGTGTCCTGCAGGGATCCCTCTCCAAATGAAATGAACTTCCTTATATAG
AGGAAGGGTCTTGCGAAGGATAGTGGGATTGTGCGTCATCCCTTACGTC
AGTGGAGAT3'.

Figure 2:
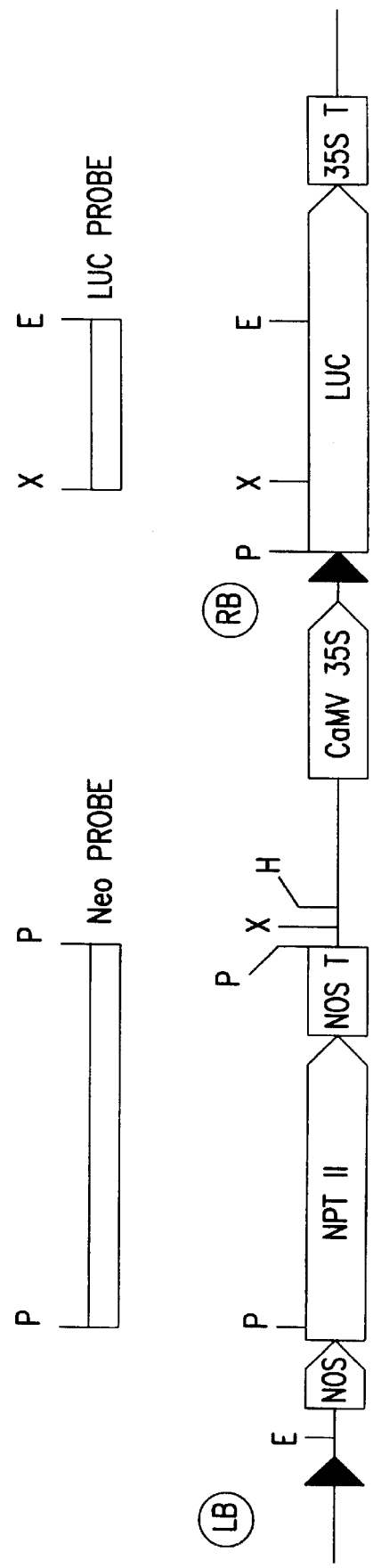
FIG. 2: A schematic diagram of the pNeoRBLuc plasmid is provided. LB, left border; RB, right border. The top boxes above the diagram indicate the probes used for southern blot analysis of transformants. Restriction sites are indicated as follows: E=EcoRI; P=Pst; X=XbaI, H=HindIII. "NOS" designates the nopaline synthase promoter. "NPTII" designates the neomycin phosphotransferase II open reading frame. "NOS T" designates the nopaline synthase terminator. "CaMV 35S" designates the 35S promoter from cauliflower mosaic virus(CaMV). "LUC" designates the open reading frame for luciferase. "35S T" designates the terminator of the CaMV 35S transcript.

For introduction of T-DNA borders, two synthetic oligonucleotides corresponding to the right border sequence of LBA5269 (Van Haaren et al., 1989) were annealed to yield the duplex: (ATCCGGCAGGATATATACCGTTGTAATTCTGCA) (SEQ ID NO:10). This duplex flanked by BamHI-PstI sites was inserted into the corresponding sites in pCIB1711 between the promoter and the luciferase coding sequence yielding pRB(+)Luc. In pRB(-)Luc, the right border sequence was introduced in reverse orientation with respect to the promoter.

pNeoRBLuc was designed for stable transformation of tobacco suspension cells and contains a left border sequence, the neomycin phosphotransferase gene (nptII) and the luciferase gene with the right border inserted between the promoter and the luciferase coding region from pRB(+) Luc (FIG. 2). The nptII gene driven by the nos (nopaline synthase) promoter was excised from the plasmid pBin19 as a 2.2 kb SacII-HindIII fragment (Bevan, 1984). The left border sequence was excised from pBin19 as a BglII-EcoRI fragment. Both of these fragments were inserted into XbaI-HindIII sites of pRB(+)Luc. pNeoLuc is the equivalent of pNeoRBluc with no right border sequence inserted between the CaMV35S promoter and the luciferase coding region.

VirD1 and VirD2 genes from pTiA6 were subcloned into expression vector pMF6 (Callis et al., 1987), consisting of the CaMV35S promoter (0.5 kb), the Adh1 first intron (0.5 kb), and the nopaline synthase (nos) polyadenylation region (0.25 kb) (FIG. 1). The 0.6 kb EcoRI-PstI from pAD1187 (Ghai and Das, 1989) corresponding to the VirD1 coding sequence was cloned into pMF6 yielding p35SAdhD1. The VirD2 coding sequence was excised as a 1.8 kb EcoRI fragment from pAD1190 (Ghai and Das, 1989) and cloned in pMF6. The plasmids obtained, p35SAdhD2 and p35SAdhD2(rev), carried the VirD2 coding region in either the sense or the antisense orientation. The Adh1 intron sequence was deleted from p35SAdhD1, p35SAdhD2 and p35SAdhD2(rev) to create p35SD1, p35SD2 and p35SD2 (rev), respectively, for experiments designed for tobacco tissues.

pGUS is a pUC derivative containing the β-glucuronidase (GUS) coding sequence GUS gene under the control of the CaMV35S promoter and the castor bean catalase gene intron (Ohta et al., 1990).

2. Plant Material

Maize suspension cells: Suspension cultures of maize (*Zea mays* L.) were initiated from cryopreserved embryogenic type II callus selected from immature embryos of an elite line related to B73. About 1 g of cryopreserved callus (DiMaio and Shillito, 1992) was added to 50 ml N6 liquid medium (Chu et al., 1975) supplemented with 30 g/l sucrose and 2 mg/l 2,4-dichlorophenoxy acetic acid (2,4-D) (2N63S). Cultures were incubated at 25° C. in the dark on an orbital shaker at 150 rpm. Suspension cultures were subcultured every 7 days by transferring 1 ml packed cell volume into 50 ml fresh 2N63S liquid medium.

Maize cell suspensions used for bombardment experiments were taken from 3 day-old rapidly growing cultures. Before bombarding, approximately 0.5 ml of packed volume cells was vacuum filtered onto 7-cm filters (Whatman, N°4).

Filters were then transferred onto gelrite-solidified N6 medium containing 120 g/l of sucrose. Plated cells were kept 4 hours at 25° C. prior to bombardment. After bombardment, plates were incubated at 25° C. for 24 hr.

Tobacco suspension cells: The *Nicotiana tabacum* cell line NT-1 (An, 1985) was grown in Murashige and Skoog medium (Murashige and Skoog) supplemented with 2 mg/l of 2,4-D and sucrose (30 g/l) (MS3S). Cells were subcultured once per week by adding 5 ml of inoculum to 100 ml of fresh medium in 500-ml flasks. The flasks were incubated at 27° C. on a rotary shaker at 125 rpm. Aliquots of 0.5 ml from four-day-old cultures were spread onto sterile filters (Whatman N°4), which were then transferred onto MS medium supplemented with 12% sucrose and kept at room temperature for 4 hours prior to bombardment.

3. Bombardment of Plant Cells

Tissues were bombarded with gold microprojectiles onto which was precipitated a mixture of plasmids. pGUS plasmid DNA was used as internal control for maize and tobacco experiments in all cases. For cotransformation experiments, the gold particles carried either an equal mass of all plasmid DNAs (0.5 μg of each plasmid DNA per target plate) or 2:1 molar ratio of plasmids carrying VirD1 and VirD2 genes to substrate plasmid. For stable transformation experiments, co-transformation mixtures contained a 5:1 molar ratio of plasmids carrying VirD1 and VirD2 genes to nptII selection plasmid. Each aliquot of plasmid mixture bombarded per target plate consisted of 0.1 μg of the selection marker and 0.5 μg each of p35SD1 and p35SD2 plasmid DNAs. Appropriate quantities of each DNA were mixed in a total volume of 10 μl and precipitated with 50 μl of 2.5 M $CaCl_2$ and 20 μl of 0.1 M spermidine-free base to effect precipitation onto 50 μl of 1.0 μm gold microcarriers (60 mg/ml). Microprojectile bombardment was performed with the PDS-1000 He biolistic device (DuPont) using 1500 psi rupture discs with the sample positioned 8 cm below the stopping screen shelf.

4. Stable Transformation of Tobacco Suspension Cells 24 hr after bombardment, tobacco cells were transferred onto MS3S plates with 300 μg/ml kanamycin. Independent microcalli that appeared about 3 weeks after bombardment were transferred onto fresh plates supplemented with 300 μg/ml kanamycin. After two subcultures on the same medium, suspension cultures were initiated by inoculating about 100 mg of tobacco cells into 25 ml liquid medium supplemented with 300 μg/ml kanamycin.

5. Transient Expression Assays

Luciferase was assayed in tissue extracts according to the recommendation of the supplier (Luciferase assay system, Promega). β-glucuronidase activity was determined by a chemoluminescent assay with the GUS-Light kit (Tropix). Luciferase and β-glucuronidase activities are expressed as light units detected by an Analytical Luminescence model 2001 Luminometer integrated over 10 seconds at 25° C.

6. DNA Extraction and Southern Blot Hybridization

Cell cultures were harvested by filtration 10 days after inoculation and frozen in liquid nitrogen. DNA was isolated as described (Hall et al., 1991). Approximately 5 μg of genomic DNA was used for digestion with EcoRI. Following separation on a 0.7% agarose gel, the DNA was transferred to genescreen plus membrane and hybridization was performed according to the conditions described by the manufacturer (NEN Research Products, DuPont). DNA probes were labeled with [a-$^{32}$ P]dCTP using the oligo labeling kit of Pharmacia . The neo probe corresponded to a 2-kb PstI fragment of the nptII gene (FIG. 2). The luc probe corresponded to a 0.7 kb XbaI-EcoRI fragment of the luciferase gene (FIG. 2). For removal of probes, membranes were stripped with a solution of 0.1% SDS at 100° C. for 5 min.

7. Cloning of T-DNA/Plant DNA Junctions

DNA (30 μg) from transgenic tobacco calli was digested with EcoRI and subjected to preparative electrophoresis on a 1% sea-plaque agarose gel (FMC). Slices of agarose corresponding to the size of fragments to be cloned were cut out of the gel and DNA was extracted from agarose with QIAquick Gel Extraction Kit (Qiagen). Fragments were then cloned into the dephosphorylated EcoRI site of pUC19. Ligation mixes were used to transform E.coli HB101 cells by electroporation. Colonies containing the plasmid with the correct insert were identified by colony filter hybridization, using a 0.5 kb CaMV35S promoter fragment as probe. Sequence of the junction of donor plasmid DNA with plant DNA was analyzed using the primer (CCACTATCCTTCGCAAGACC) (SEQ ID NO:11) located in the CaMV35S promoter at a distance of 106-bp from the right border sequence.

D. Results

1. Experimental Design

In order to investigate whether VirD1 and VirD2 gene products can nick a T-DNA border sequence when expressed in plant cells, we constructed the test plasmid pRB(+)Luc, containing a substrate T-DNA border sequence between the promoter and the coding region of the luciferase gene. The insertion of the right border sequence between the CaMV35S promoter and the luciferase coding region does not interfere with the expression of the luciferase gene in plant tissues (data not shown). The border sequence was situated in such a way that a site-specific nick introduced by VirD1 and VirD2 gene products would lead to a break in the DNA strand that is template for the luciferase mRNA, and thus should decrease the production of luciferase transcript and enzyme. After co-bombardment of plant cells with pRB(+)Luc and plasmids carrying the vir D genes, any nicking at the border sequence should be measurable quantitatively by assaying luciferase activity. However, any decrease of luciferase activity could also be explained by the binding of VirD1 and VirD2 gene products at the border sequence located between the promoter and the coding sequence, binding that might inhibit the transcription of the luciferase gene. pRB(-)Luc, a plasmid that contains the border sequence in reverse orientation with respect to the promoter, was therefore tested to distinguish between these two possibilities. If a decrease of luciferase activity is the result of the binding of the VirD gene product(s) to the border sequence, then this decrease would probably be observed even with the border sequence in reverse orientation.

Since VirD1 and VirD2 proteins must be produced transiently in the bombarded plant cells before they can nick the border sequence, any such nicking presumably would occur after transcription of the luciferase gene has already started. Therefore luciferase activity measurements would presumably underestimate the VirD1 and VirD2 activity in plant cells.

To express VirD1 and VirD2 genes in plant cells, their respective open reading frames (ORFs) were placed under the control of the CaMV35S promoter. The VirD2 ORF was also introduced in antisense orientation with respect to the promoter to serve as control. As the presence of the maize alcohol dehydrogenase 1 intron 1 has been found to increase the expression of genes in maize (Callis et al., 1987), we also constructed p35SAdhD1 and p35SAdhD2 (containing the intron inserted between the promoter and the coding region of VirD1 and VirD2 ORF genes respectively) for use in maize transient expression experiments. A plasmid expressing the β-glucuronidase (GUS) gene, pGUS , was included in each bombardment as an internal standard to control for the efficiency of DNA transfer. In all cases, the activity of reporter is expressed as a ratio of luciferase to GUS activity, to correct for variability in efficiency of DNA delivery.

2. Transient Expression Assays to Test for Cleavage of the Border Sequence by VirD1 and VirD2 Gene Products in Planta Maize and tobacco cells were first transiently transformed with our test plasmid codelivered with VirD1 and VirD2 genes separately, in order to test their ability individually to affect transcription through the T-DNA border sequence. Following co-delivery of either p35SD1 DNA or p35SAdhD1 DNA with pRB(+)LUC DNA, 80% of the control level of luciferase to GUS activity was observed in tobacco and maize tissues (Table 1 and Table 2; see below). Codelivery of p35SD2 DNA (tobacco) or p35SAdhD2 DNA (maize) with pRB(+)LUC DNA resulted in 50% and 80% of the control level of luciferase to GUS activity (Table 1 and Table 2; see below).

TABLE 1

Activity of VirD1 and VirD2 in tobacco suspension cells.

| Plasmids + pGUS | Mean | ±SD | % of control |
|---|---|---|---|
| pRB(+)LUC | 1.36 | ±0.06 | — |
| pRB(+)LUC + p35SD1 | 0.98 | ±0.03 | 72 |
| pRB(+)LUC + p35SD2 | 0.69 | ±0.07 | 50 |
| pRB(+)LUC + p35SD1 + p35SD2 (1:1:1) | 0.27 | ±0.05 | 20 |
| pRB(+)LUC + p35SD1 + p35SD2 (1:2:2) | 0.14 | ±0.05 | 10 |
| pRB(+)LUC + p35SD1 + p35SD2(rev) (1:1:1) | 1.08 | ±0.13 | 80 |
| pRB(+)LUC + p35SD1 + p35SD2(rev) (1:2:2) | 1.13 | ±0.08 | 83 |
| pRB(−)LUC | 1.40 | ±0.14 | — |
| pRB(−)LUC + p35SD1 | 1.33 | ±0.13 | 95 |
| pRB(−)LUC + p35SD2 | 1.19 | ±0.12 | 85 |
| pRB(−)LUC + p35SD1 + p35SD2 | 1.56 | ±0.38 | 112 |

Table 1. Activity of VirD1 and VirD2 in tobacco cells.

Plasmid constructs are described in FIG. 1 and were delivered to tobacco cells by the biolistic device. Numbers between brackets indicate the molar ratio of plasmids. Following incubation for 24 hrs, tissues were homogenized and enzyme activities determined. Activities are expressed as a ratio of luciferase (Luc) to β-glucuronidase (Glu). Independent bombardments were analyzed and data are presented as mean values of 6 repetitions plus or minus standard deviation. % control values are determined from the ratio of the luciferase to β-glucuronidase activities to those activities observed with control plasmid.

TABLE 2

Activity of VirD1 and VirD2 genes in maize suspension cells.

| Plasmids + pGUS | Mean | ±SD | % of control |
|---|---|---|---|
| pRB(+)LUC | 1.26 | ±0.27 | — |
| pRB(+)LUC + p35SAdhD1 | 1.32 | ±0.28 | 105 |
| pRB(+)LUC + p35SAdhD2 | 1.02 | ±0.15 | 81 |
| pRB(+)LUC + p35SAdhD1 + p35SAdhD2 (1:1:1) | 0.11 | ±0.03 | 8.7 |
| pRB(+)LUC + p35SAdhD1 + p35SAdhD2 (1:2:2) | 0.006 | ±0.007 | 0.5 |
| pRB(+)LUC + p35SAdhD1 + p35SAdhD2(rev) (1:1:1) | 0.99 | ±0.20 | 78.6 |
| pRB(+)LUC + p35SAdhD1 + p35SAdhD2(rev) (1:2:2) | 0.96 | ±0.26 | 76 |

Table 2. Activity of VirD1 and VirD2 in maize cells. Activities are expressed as described in footnote to Table 1.

The two vir genes together appeared to have a synergistic effect. Co-delivery by the biolistic device of equal amounts of pRB(+)LUC DNA with both plasmids carrying VirD1 and VirD2 genes (ratio of 1:1:1) reduced luciferase activity to ca. 20% of control in tobacco (Table 1) and 10% in maize cells (Table 2). At a higher ratio of VirD1 and VirD2 plasmids to test plasmid (2:2:1), the luciferase activity was reduced further to ca. 10% in tobacco cells (Table 1) and 1% in maize cells(Table 2). Analogous experiments using the control plasmid p35SD2(rev) (tobacco) or p35SAdhD2(rev) (maize) with the VirD2 coding sequence in antisense orientation gave results similar to those with VirD1 alone (Table 1 and Table 2) as expected. This demonstrated that our internal standard GUS gene was an effective control for any effects of altering total DNA concentration delivered.

Reversal of orientation of the T-DNA border in the test plasmid eliminated or greatly reduced any influence of VirD1 and/or VirD2 genes on transient expression of the luciferase gene. When pRB(−)Luc was co-bombarded into tobacco cells with p35SD1 and p35SD2 plasmid DNA, no significant decrease in luciferase activity was observed. Co-delivery of pRB(−)Luc performed with p35SD1 or p35SD2 separately likewise showed no significant decrease of luciferase activity (Table 1). These observations strongly indicated that the decrease of luciferase activity seen with pRB(+)Luc test plasmid plus VirD1 and VirD2 genes was the result of a strand-specific nick at the right border sequence by vir gene products similar to that observed in Agrobacterium (for review, Zambryski, 1992).

3. Analysis of Stable Transformants

Stable transformation of tobacco suspension cells was next undertaken to assess the activity of VirD1 and VirD2 gene products on the pattern of DNA integration after co-delivery of these genes with their substrate DNA by the biolistic device. For these experiments pNeoRBLuc was used, which contains a left T-DNA border, nptII as selectable marker, and the 35SRB(+)Luc gene with the right T-DNA border inserted between promoter and luciferase coding region. In the results and discussion below, we designate as "agrolistic events" those DNA insertions into the tobacco genome that would result after VirD1 and VirD2 activity on border sequences, generating a T-strand. In contrast, we designate as "biolistic events" those DNA inserts representing the process normally occurring after gene delivery into plant cells by the biolistic device. The initial criterion to distinguish biolistic events and putative agrolistic events was absence of luciferase activity in the transformed clone, arising from exclusion of the Luc coding region by T-DNA excision from pNeoRBLuc. At the molecular level, the transgenes representing an agrolistic event should hybridize with the neo probe and not with the luc probe. Moreover, in an agrolistic event, the sequence of the junction between introduced DNA and plant DNA should correspond precisely to the right border end of a T-strand. Both types of events may occur in the same plant cell, but such clones would be scored genetically as biolistic events based on the presence of luciferase activity. Both biolistic and putative agrolistic events were investigated by southern hybridization to measure the frequency of each type of insertion.

Tobacco suspension cells were bombarded with microprojectiles coated with pNeoRBLuc plasmid DNA together with p35SD1 and p35SD2 DNA in a ratio 1:5:5. As controls, pNeoRBLuc plasmid was also bombarded alone and the borderless control plasmid pNeoLuc was co-bombarded with p35SD1 and p35SD2. Stable transformants were selected by growth on kanamycin-containing medium. An average of 40 kanamycin-resistant clones appeared per bombarded filter, but only one or two calli were further analyzed per plate. Similar numbers of kanamycin-resistant calli were recovered following bombardment with the control plasmids pNeoRBluc DNA alone or pNeoLuc DNA plus p35SD1 DNA and p35SD2 DNA.

A rough estimate of the frequency of agrolistic events could be made by the ratio of the total number of kanamycin-resistant calli analyzed that do not express luciferase to total kanamycin calli. By this criterion, the frequency of agrolistic events was about 10%; out of 32 callus lines analyzed, 3 did not express luciferase activity. As argued above, this number is probably an underestimate of agrolistic events because agrolistic events and biolistic events can take place in the same plant cell.

4. Southern Blot Analysis of Control "Biolistic" Events

Southern blot hybridization was performed on DNA from control kanamycin-resistant callus lines obtained after bombardment with (i) pNeoRBLuc alone, and (ii) pNeoLuc plasmid co-bombarded with p35SD1 and p35SD2 DNAs. Genomic DNA was digested with EcoRI, which produces a 3.9 kb fragment from the pNeoRBLuc plasmid that is homologous to both neo and luc probes (FIG. 2). When genomic DNA digests were hybridized with the neo probe, all lanes exhibited a hybridizing band of the predicted size (3.9 kb) and the number of intact fragment copies, based on comparison of hybridization intensity with copy control lanes, varied from 1 to more than 10 per nucleus. Southern blot analysis of transformed lines from co-bombardment with p35SD1 DNA and p35SD2 DNA together with the borderless control plasmid pNeoLuc used as probes revealed the presence of both intact and rearranged copies of the nptII gene in these lines. Such rearrangements are often observed in transformants obtained by the biolistic device.

5. Southern Blot Analysis of Candidate Agrolistic Events

Southern blot analysis was also performed on DNA from 16 kanamycin-resistant callus lines obtained after co-bombardment of pNeoRBLuc using p35SD1 and p35SD2 plasmid DNA as hybridization probes. For Southern blot analysis, 13 callus lines were chosen randomly among the 32 that tested positively for the luciferase activity, along with three clones found not to express luciferase. DNA from the luciferase-positive callus lines contained a band of the predicted size (3.9 kb) hybridizing with the neo probe. The number of intact nptII gene copies, based on comparison of hybridization intensity with copy control lanes, ranged from 1 to 10 per nucleus. The number of copies observed was much lower in calli transformed with pNeoLuc DNA and p35SD1 and p35SD2 DNA.

We observed a 3.4 kb band in DNA from all transgenic calli bombarded with p35SD1 and p35SD2 DNA together with pNeoRBLuc. A fragment of this size was found to hybridize with VirD2 probe in these lines. The fragment used for the neo probe contained a piece of terminator sequence that was also present in p35SD1 and p35SD2 constructs, and although it represents only 1.2% of the labeled probe, there may be many copies of VirD gene inserts and this could give a signal of the magnitude seen.

When blots were hybridized with the luc probe, 3 groups of transgenic callus lines could be distinguished: (i) callus lines with inserts hybridizing with the neo probe and the luc probe; (ii) callus lines in which some inserts hybridized with only the neo probe and some inserts hybridized with both probes neo and luc; (iii) callus lines with inserts hybridizing only with the neo probe. The first group of calli probably did not contain agrolistic events. The second group of calli probably contained two types of events: agrolistic events evidenced by the presence of 4.8 kb, 4.6 kb and 5 kb fragments hybridizing to the neo probe, and biolistic events evidenced by the presence of a 3.9 kb fragment hybridizing to the luc probe. The third group of calli exhibited only putative agrolistic events based on their ability to hybridize only with the neo probe. Three callus lines fell into this group; one containing a 3.2 kb hybridizing band, a second containing two hybridizing bands of 3.8 kb and 5 kb, and a third containing one band of 5.5 kb. These 3 hybridization patterns were unique, clearly representing independent single cell transformation events. Among 16 transgenic tobacco lines analyzed by southern hybridization, 10 exhibited biolistic events, 3 exhibited putative agrolistic events and 3 exhibited both.

6. Molecular Analysis of Putative Agrolistic Events

The nature of putative agrolistic insertion events was ultimately verified by determining the sequence of the junction between integrated DNA and plant DNA in callus lines exhibiting hybridization patterns consistent with such putative events. DNA fragments from these callus lines which included these junctions were cloned and sequenced outward from inside the T-DNA borders (see methods). The nucleotide sequence revealed that each of these fragments contained a sequence indicative of a right border/plant DNA junction. The right end point of the T-DNA was identical to the nicking site of the right border sequence of T-DNA.

The plant nucleotide sequence in four of the five cases perfectly matched tobacco junction sequences that have been previously reported in cDNA form by others. Interestingly, in all four cases, the right border of T-DNA is inserted with the CaMV35S promoter oriented in the anti-sense direction with respect to the plant genes in high AT regions near the polyadenylation site in the 5'-untranslated region of the gene. No additional nucleotides and no repeated sequences were observed at the right junction sites. It is not possible to conclude whether any deletions of the target sites have occurred because the left border of the insert was not determined.

As controls, DNA fragments including the right border sequence and adjoining regions on either side were also cloned from callus lines exhibiting hybridization patterns consistent with biolistic events DNA fragments. The nucleotide sequence from these events did not show any right border sequence-plant DNA junction, but rather the full length right border sequence and the expected luciferase coding sequence beyond.

E. Conclusion

The Ti plasmid-encoded virulence proteins VirD1 and VirD2 are required for the formation of T-strands in Agrobacterium. Here we present evidence for T-DNA formation in planta and integration in plant cells after introducing by the biolistic device the two virulence genes VirD1 and VirD2 under the control of the CaMV35S promoter together with a plasmid harboring the border sequences. About 10% of the transformed tobacco calli exhibited agrolistic inserts, i.e. DNA integrated after the action of VirD1 and VirD2 gene products only. A similar fraction of transformed calli contained both agrolistic events and biolistic events. The transgene:: plant DNA junctions in agrolistic events demonstrated site-specific cleavage within the right border sequence, in concordance with compiled data showing the right border T-DNA ends just after the first 3 nucleotides of the 25-bp repeat (Gheysen et al, 1991; Mayerhofer et al., 1991; Ohba, 1995). The precision of integration events has been interpreted as a direct involvement of VirD2 in the recombination process in the plant cell nucleus (Tinland et al., 1995).

The integration sites of the agrolistic events are here identified in transcribed regions, supporting the data that T-DNA is preferentially integrated into potentially transcribed genomic loci in different plant species (Koncz et al., 1989; Herman et al., 1990, Kertbundit et al., 1991) with T-DNA insertions randomly distributed in plant chromosomes (Chyi et al., 1986; Wallroth et al., 1986). Although T-DNA integration is usually not correlated with large rearrangements in the plant DNA, deletions, inversions and duplications of target plant DNA sequences can occur during T-DNA transformation. For the agrolistic events examined here, no major rearrangement was noted in the plant target sites.

The consistent pattern of agrolistic integrations near the polyadenylation signal of known tobacco light-inducible and/or photosynthetic genes with the CaMV35S promoter at the right border directed in an antisense orientation to the open reading frame is intriguing. In this orientation, the insertion of the T-DNA structure may generate an antisense transcript that might inactivate expression of the corresponding tobacco gene. Such photosynthetic genes are, however, not required by these non-photosynthetic cultured NT1 cells.

Based on the transient expression experiments in which cleavage at the right border sequence appeared to occur at high frequency, a high percentage of substrate molecules were apparently cleaved. Surprisingly, this proportion is not kept for stable transformation. This could be explained by a ligation reaction at the right border sequence after cleavage by VirD2, for in vitro assays have shown that VirD2 catalyzes a site-specific cleaving-joining reaction within single-stranded oligonucleotides containing T-DNA border sequences (Pansegrau et al., 1993). Another explanation may be the absence of the single-strand binding VirE2 necessary for efficient Agrobacterium-mediated transformation. Although one can presume that there is an equivalent to the non-specific single-strand binding protein VirE2 in plant cells that could bind and protect the T-strand, the addition of the virE2 gene together with VirD1 and VirD2 might improve the efficiency of recovery of agrolistic events.

We note also the disadvantage that the accompanying VirD1 and VirD2 genes codelivered with the transforming plasmid presumably are biolistically integrated into the same transformed lines at high frequency: cotransformation is very efficient with the biolistic device. These unwanted genes represent a different kind of extraneous DNA. However we presume, because of their unique insertion mechanism, that they are not linked to the "agrolistic" insert and can be eliminated by subsequent breeding of the transgenic plant. This presumption cannot be tested with these transgenic NT1 cells, which are not regenerable.

The agrolistic transformation system offers several distinct advantages: (i) It should be immediately applicable to any plant target tissue susceptible to biolistic transformation methods.(ii) The inserted DNA does not carry extraneous vector DNA (iii) Fewer copies of the gene of interest are inserted than is the case for DNA delivered without VirD1 and VirD2 genes. This should minimize regions of homology which may contribute to instability.

The agrolistic approach thus combines the best features of biolistic delivery with the elegance and precision of Agrobacterium T-DNA insertion mechanism to afford a new, widely applicable technology for producing transgenic crop plants of agricultural value.

Example 2
Construction of Plant Expression Cassettes

Gene sequences intended for expression in transgenic plants or plant cells are firstly assembled in expression cassettes behind a suitable promoter and upstream of a suitable transcription terminator to create a chimeric gene. These expression cassettes can then be easily transferred to the plant transformation vectors described above in Example 3.

Promoter Selection

The selection of a promoter used in expression cassettes or chimeric genes will determine the spatial and temporal expression pattern of the transgene in the transgenic plant. Selected promoters will express transgenes in specific cell types (such as leaf epidermal cells, mesophyll cells, root cortex cells) or in specific tissues or organs (roots, leaves or flowers, for example) and this selection will reflect the desired location of expression of the transgene. Alternatively, the selected promoter may drive expression of the gene under a light-induced or other temporally regulated promoter. A further alternative is that the selected promoter be chemically regulated. This would provide the possibility of inducing expression of the transgene only when desired and caused by treatment with a chemical inducer.

Transcriptional Terminators

A variety of transcriptional terminators are available for use in expression cassettes. These are responsible for the termination of transcription beyond the transgene and its correct polyadenylation. Appropriate transcriptional terminators and those which are known to function in plants and include the CaMV 35S terminator, the tml terminator, the nopaline synthase terminator, the pea rbcS E9 terminator. These can be used in both monocotyledons and dicotyledons.

Sequences for the Enhancement or Regulation of Expression

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize Adh1 gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., Genes Develop. 1: 1183–1200 (1987)). In the same experimental system, the intron from the maize bronze1 gene had a similar effect in enhancing expression (Callis et al., supra). Intron sequences have been routinely incorporated into plant transformation vectors, typically within the non-translated leader.

A number of non-translated leader sequences derived from viruses are also known to enhance expression. Specifically, leader sequences from Tobacco Mosaic Virus (TMV, the "omega-sequence"), Maize Chlorotic Mottle Virus (MCMV), and Alfalfa Mosaic Virus (AlMV) have been shown to be effective in enhancing expression (e.g. Gallie et al. Nucl Acids Res. 15: 8693–8711 (1987); Skuzeski et al. Plant Molec. Biol. 15: 65–79 (1990))

Example 3
A "Hit and Run" Method for Effecting Site Specific Recombination in Biolistically Delivered DNA: Co-Delivery of Recombinase mRNA A. Abstract We describe a method for co-delivery of DNA and mRNA to plant cells using the biolistic device. By gel electrophoresis we have demonstrated the stability and recovery of DNA and RNA precipitated onto microprojectiles under various conditions. For delivery of active mRNA, precipitation by $CaCl_2$ alone or $CaCl_2$ plus spermidine plus Tris buffer was effective, while unbuffered spermidine fragmented the RNA.

Using efficient precipitation methods and biolistic delivery to maize and tobacco cells, we demonstrated expression of in vitro synthesized capped polyadenylated mRNA encoding firefly luciferase. Kinetic studies demonstrated that luciferase mRNA expression peaked earlier than that for transient expression of a 35S/luciferase DNA delivered concurrently.

To demonstrate activity of biolistically delivered mRNA encoding R, the site-specific recombinase of *Zygosaccharomyces rouxii*, we codelivered to maize cells a substrate plasmid containing a reversed 35S promoter flanked by inverted copies of RS, the 31 bp specific target site for the recombinase, followed by 35S leader, luciferase gene and 35S terminator regions. While the substrate plasmid alone gave no significant luciferase expression, when codelivered with R mRNA, its 35S promoter was flipped by recombinase and luciferase enzyme was produced.

The potential use of site-specific recombinase systems to control transgene insertion and expression are discussed, together with the advantages of introducing recombinase activity transiently as mRNA.

B. Introduction

When particle bombardment is used for gene-delivery to plant cells, the transgene DNA inserts randomly into the genome, generally at a single site containing multiple copies (Klein et al., 1988, Klein et al., 1989; Gordon-Kamm W. J. et al., 1990; Vasil et al., 1992; Wan Y. and Lemaux P, 1994). The arrangement, insertion position and often high copy number of transgenes can lead to instability of expression by several mechanisms: for example, multiple copies of transgenes interacting to inactivate each other through antisense or methylation or other "silencing" mechanisms that are not well understood (reviewed in Matzke M and Matzke A., 1995). Because the multiple copies of transgenes are linked at a single insertion site, it is not possible to decrease copy number through segregation in subsequent generations of plants. Both for basic studies of transgene expression and for commercial production of transgenic crop plants for agricultural applications, improvement in the arrangement and expression of introduced genes is a high priority. Site-specific recombination systems can serve as a useful means of simplifying the pattern of insertion of transgenes and even directing them to a predetermined site in the plant genome (Albert et al., 1995).

Several site-specific recombinases have been shown to be active in plant cells (for review, see Odell & Russell, 1994): the Cre/lox system of the bacteriophage P1, the FLP/FRT recombination system from the 2 μ plasmid of *Saccharomyces cerevisiae*, and the R/RS system from pSR1 plasmid of *Zygosaccharomyces rouxii* (Matsuzaki et al., 1988). These systems are of potential utility because of their simplicity; to be fully operational, they need only a single recombinase protein (Cre, FLP, R) and its corresponding target, a short defined recombination site (lox, FLP, RS, respectively). Further, their frequency of recombination is remarkably high. The recombinase can mediate three types of DNA rearrangements through its recombination reactions, depending on the location and orientation of the recognition sites. If a DNA fragment is bounded by two recognition sites that are inverted with respect to each other, inversion of the intervening DNA occurs. If the two recognition sites are in the same orientation, excision and circularization of the intervening DNA occurs. When the recognition sites are on separate DNA molecules, genetic exchange occurs and if one is circular, that molecule becomes linearly integrated into the other.

Site-specific recombinase activity can be used to simplify and target transgenes introduced into plants. If this activity persists, however, it can render the recombinant structure unstable. It is therefore desirable to express the recombinase activity only transiently. This was achieved in a recent study which demonstrated targeted integration of a lox-containing transgene into a lox site in a transgenic plant expressing Cre (Albert, et. al., 1995). Because the lox site was situated between the promoter and coding region of the cre gene, the site-specific recombination event inactivated Cre expression, stabilizing the product. All integration events examined were single copy, based on Southern hybridization analysis.

In the present study we have adapted the R/RS site-specific recombinase system for use with biolistic gene delivery. The R/RS system has been shown to function efficiently in tobacco: when the R gene was transiently transformed into protoplasts, its gene product turned on a cryptic glucuronidase (GUS) gene by site-specific inversion or excision of DNA (Onouchi, et. al. 1992). We demonstrate here that the R-recombinase delivered by biolistics to maize and tobacco cells functions similarly, though with low efficiency (efficiency could be increase by optimization of parameters), to turn on a cryptic luciferase gene by flipping its promoter. Moreover use of mRNA rather than NA to produce recombinase ensures that it is produced quickly after introduction of the DNA substrate into the cell. The target RS-site contains a 31 bp palindromic nucleotide sequence consisting of a pair of 14 bp inverted repeats separated by a 3 bp asymmetric core (Matsuzaki et al, 1988). For production of transgenic plants, it is desirable to utilize recombinase mRNA rather than DNA in order to avoid insertion of the R-gene into the plant genome, and thus ensure recombinase expression only transiently, during the early stages of transformation. We describe below a method for co-introduction of mRNA coding for R-recombinase together with a target RS-containing cryptic luciferase DNA construct, resulting in transient recombinase activity that activates luciferase gene expression.

C. Materials and Methods

1. Plant Materials

Maize cells

Suspension cultures of maize (*Zea mays* L. ) were initiated from cryopreserved embryogenic type II callus selected from immature embryos of an elite line related to B73. Cryopreserved calli (DiMaio and Shillito, 1992) were thawed rapidly and about 1 g was added to 50 ml N6 liquid medium (Chu et al., 1975) supplemented with 30 g/l sucrose and 2 mg/l 2,4-dichlorophenoxy acetic acid (2,4-D) (2N63S). Cultures were incubated at 25° C. in the dark on an orbital shaker at 150 rpm. Suspension cultures were subcultured every 7 days by transferring 2 ml packed cell volume into 50 ml 2N63S liquid medium.

Aliquots containing 200 mg of cells were spread evenly onto sterile Durapore filters and placed on medium 2N6 supplemented with 12% sucrose as osmoticum. Plated cells were kept at room temperature for 4 hours prior to bombardment and up to 24 hours post-bombardment.

Tobacco cells

The *Nicotiana tabacum* cell line NT-1 (An, 1985) was grown in Murashige and Skoog medium (Murashige & Skoog , 1962) supplemented with 2 mg/l of 2,4-D and sucrose (30 g/l). Cells were subcultured once per week by adding 5 ml of inoculum to 100 ml of fresh medium in 500-ml flasks. The flasks were incubated at 27° C. on a rotary shaker at 125 rpm. Aliquots of 0.5 ml of cells four days after subculture were spread onto sterile filters (Whatman No. 4). Filters were then transferred onto MS medium supplemented with 12% sucrose and kept at room temperature for 4 hours prior to bombardment and up to 24 hours post-bombardment.

2. Plasmids

Figure 4A:
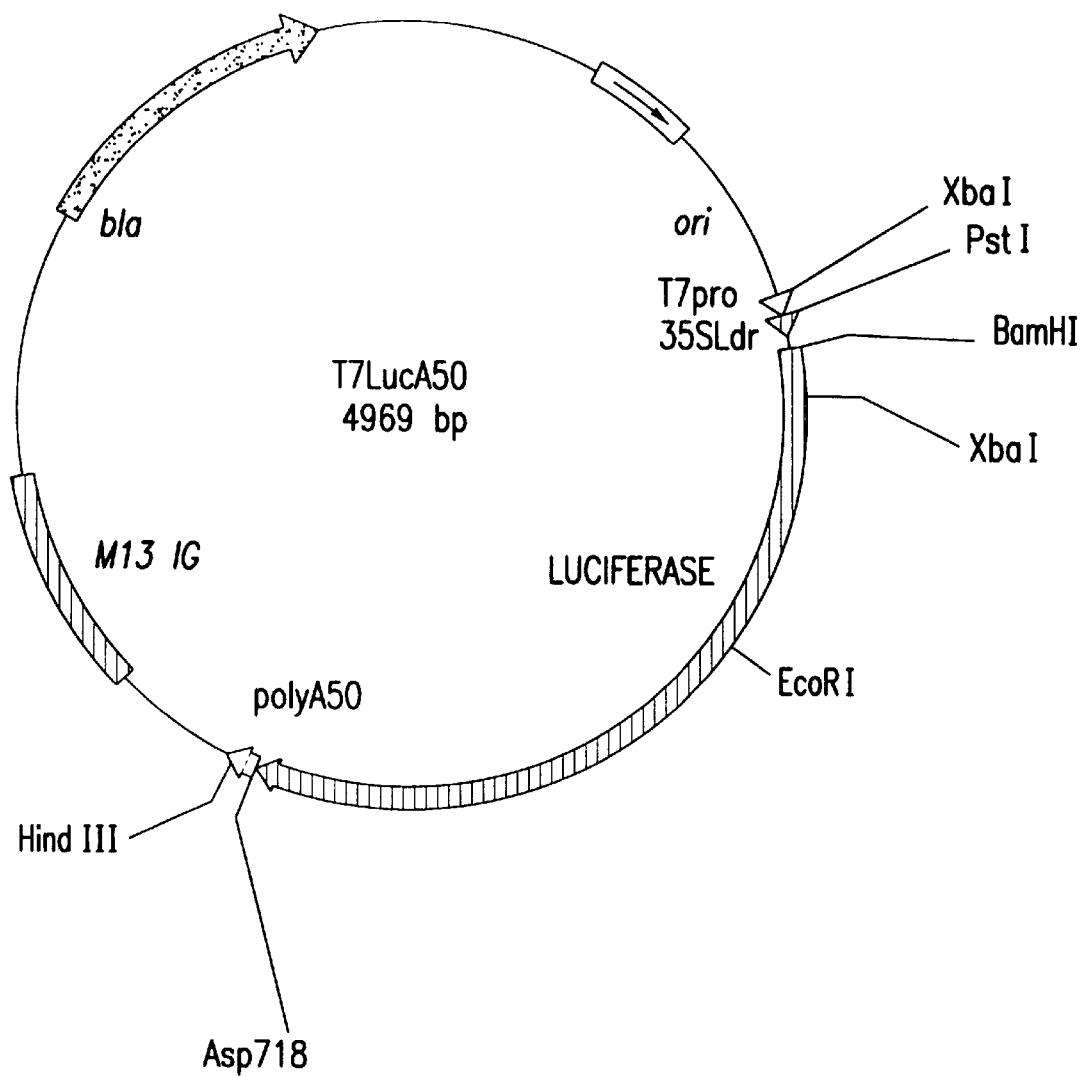
FIGS. 4A–4F: Maps of plasmids used in Examples 3 and 4 are provided. Abbreviations used are described in the "Materials and Methods" section of Example 3.
Figure 4B:
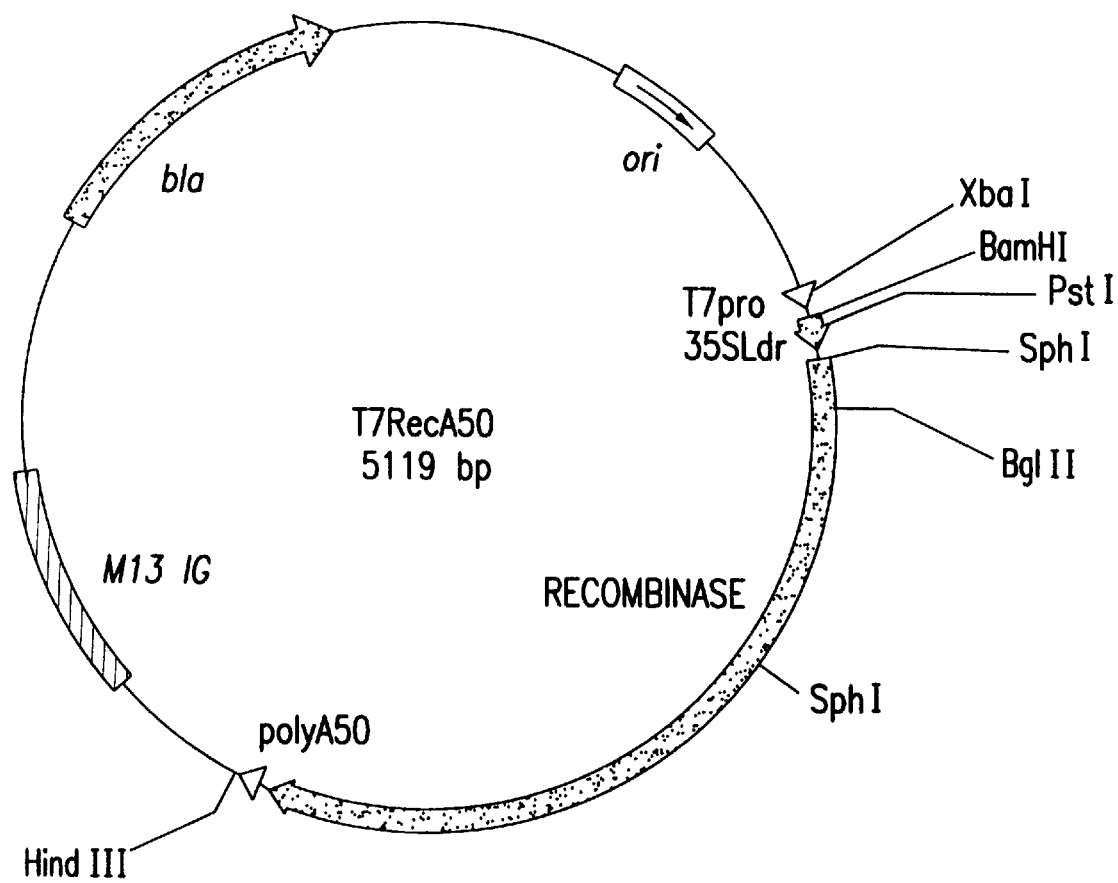
Figure 4C:
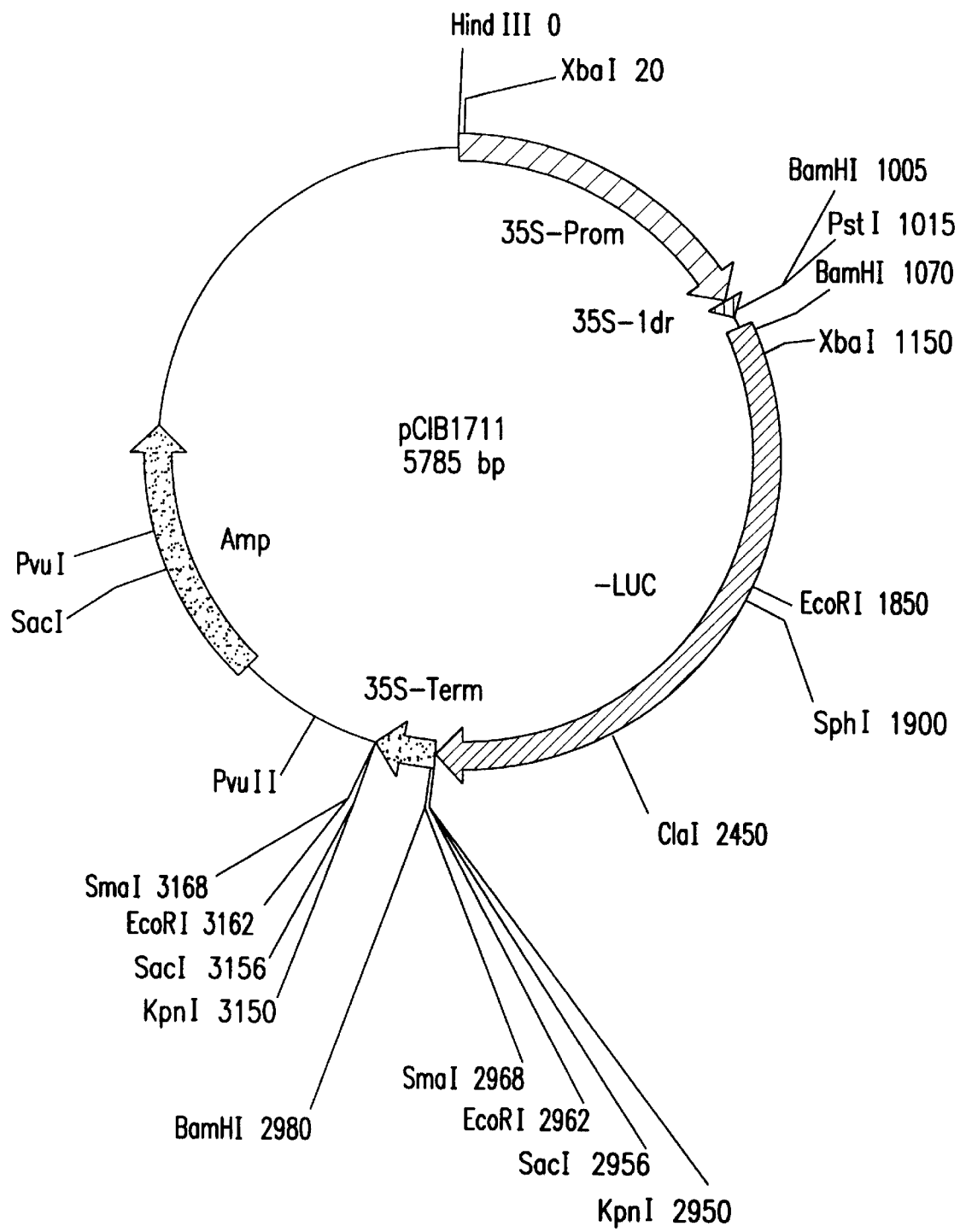
Figure 4D:
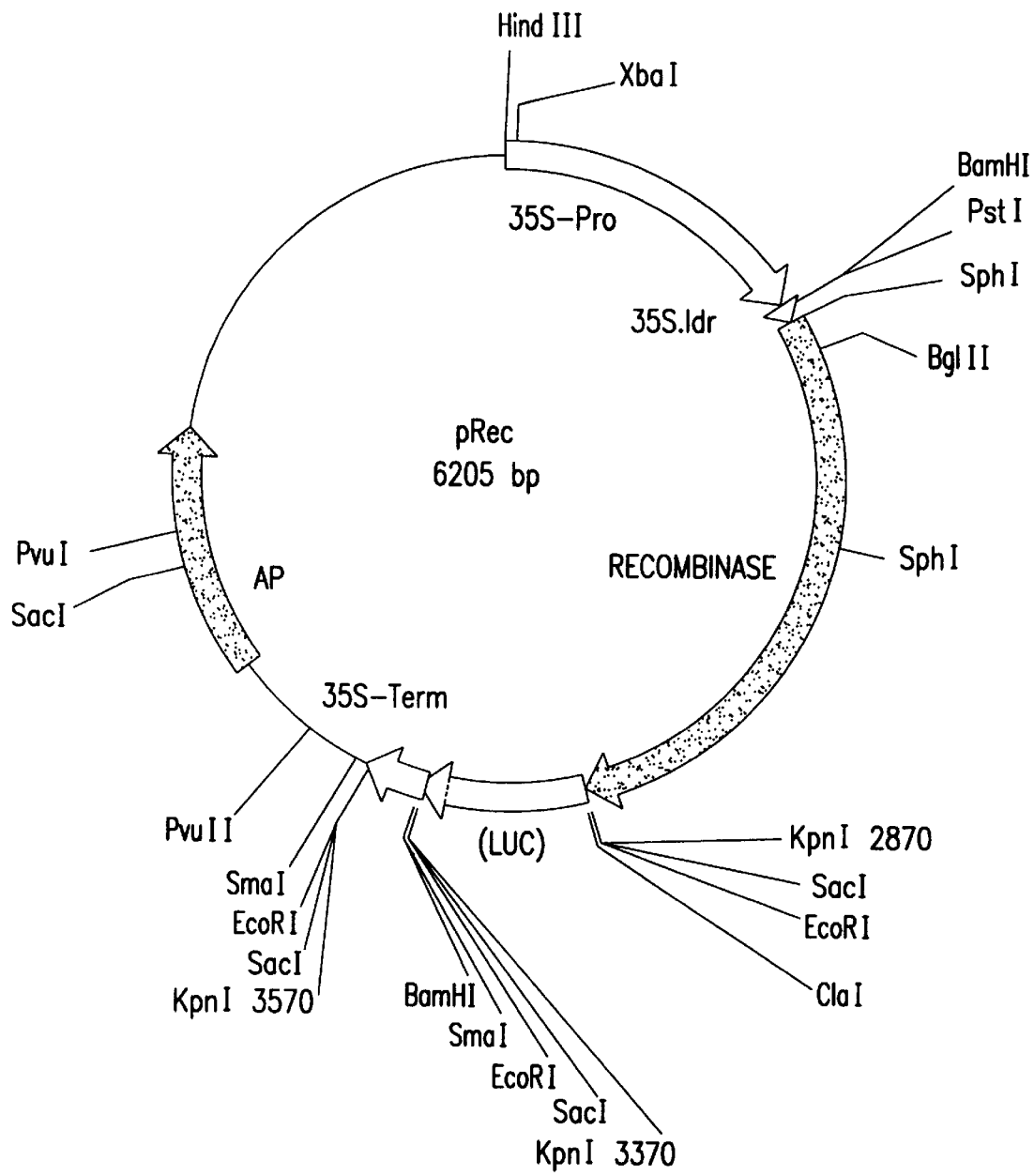
Figure 4E:
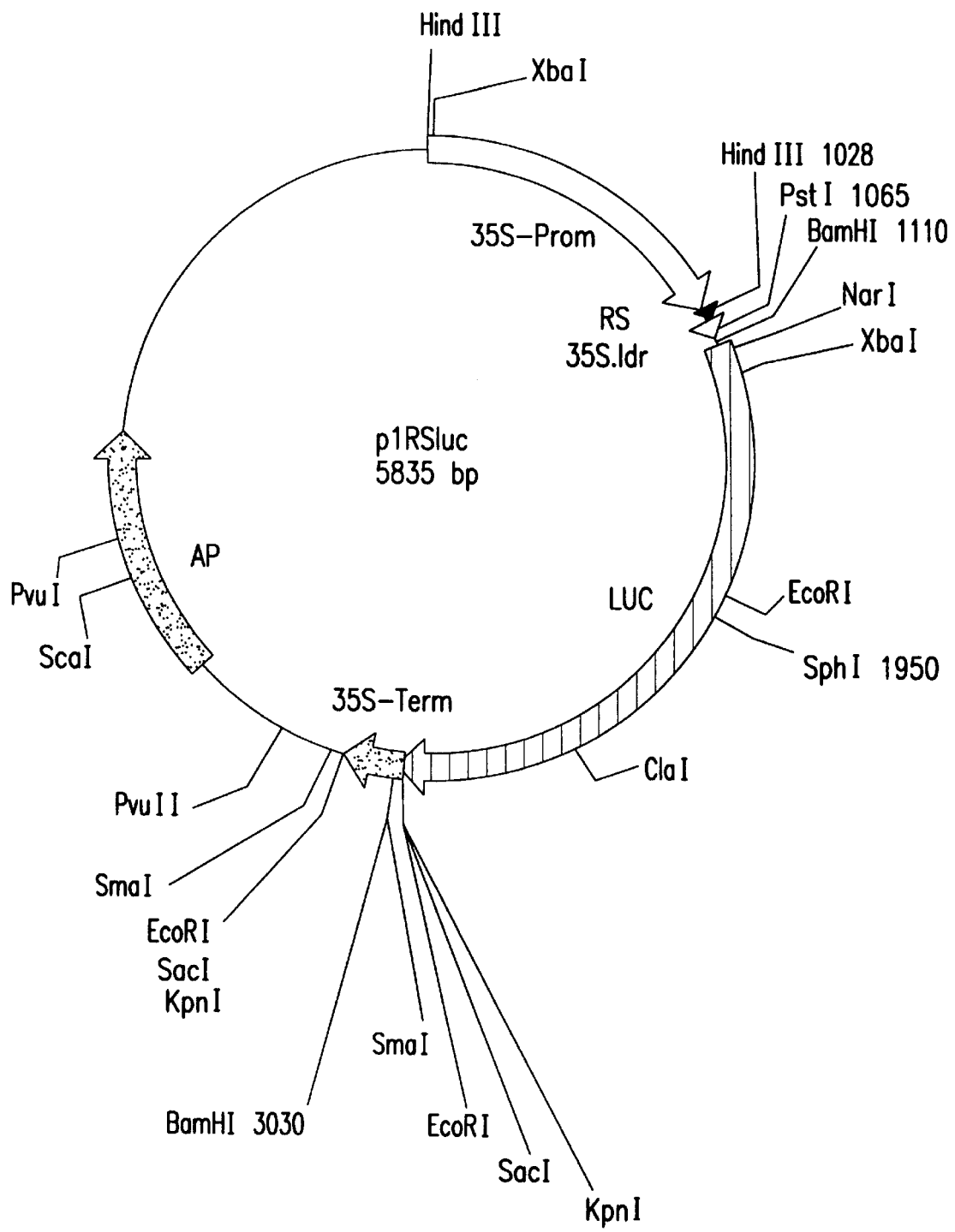

T7LUCA50 template (FIG. 4A) for in vitro transcription of firefly luciferase mRNA was constructed by first joining luc to a T7 promoter, then inserting the T7/luc fragment into a pUC18 derivative with a polyA insert. To join the T7 promoter to luc coding region, the T7 promoter was excised from pET3 (Rosenberg et al., 1987) as a BglII fragment and cloned into the BamHI site of pUC19 to form pAT26. The sequence from +9 to +26 was replaced by a BamHI site by a PCR-mediated deletion to form pAT27. The 35S-leader-luciferase fragment excised from pCIB1711 (FIG. 4C, see below) as a BamHI/Asp718 fragment was introduced into pAT27 to form T7Luc. The T7/luc insert from this plasmid was moved to pUC18A50X as an XbaI/Asp718 fragment. pUC18A50X is a pUC18 derivative containing an oligonucleotide pair with 50 A-residues flanked by Asp718 (5') and HindIII (3') overhangs, whose EcoRI site was converted to an XbaI site with a synthetic oligonucleotide.

pT7RecA50 (FIG. 4B) is a pUC18A50X derivative containing the T7 promoter, 35S leader and recombinase coding region in addition to its polyA-encoding region. The 35S leader/Recombinase fragment from pRec (see below) was excised as a BamHI/Asp718 fragment and ligated into pAT27 to form pT7Rec. the XbaI/KpnI fragment from pT7Rec was next inserted into pUC18A50X to form pT7RecA50.

pCIB1711 (FIG. 4C) is a derivative of pCIB710 (Rothstein et al, 1987) into which the luciferase coding region from pJD204 (de Wet et al., 1987) was introduced as a HindIII-BamHI fragment into the BamHI site of the vector with a BamHI/PstI/HindIII oligo adapter at the 5' end to form pCIB1701. The 35S promoter/leader of the resulting plasmid was tailored to position the BamHI site exactly at the start of transcription by substituting its EcoRV-BamHI fragment with that of pDO435 (Ow et al., 1986) to form pCIB1700. The hybrid 35S leader (50 bp)/luciferase leader (22 bp) from pCIB1700 was removed at the PstI site through NarI in the luc gene, and replaced by a synthetic oligonucleotide corresponding to the 58 bp 35S leader and the start of the luc ORF (see Carozzi et al., in preparation, for details of this construction).

pRec (FIG. 4D) is a derivative of pCIB1711 that retains the 35S promoter, leader and terminator sequences and has the luciferase coding region replaced by the recombinase coding region. To achieve this, the 5' end of the recombinase gene from pGAHR (Onouchi et al., 1991) was cloned as a BamHI/BglII fragment into the corresponding sites of pSP72 (Promega), and the DNA between vector XhoI and insert PvuII sites was replaced with an oligonucleotide: TCGAGTTGC<u>ATG</u>CAG (SEQ ID NO:12), such that the start codon of recombinase (underlined) was converted to an SphI site. The pCIB1711 vector was likewise modified to place an SphI site at the end of the 35S-leader as follows: The PstI/EcoRI fragment containing the 35S promoter/leader was subcloned into pSGpoly11 vector to make its BamHI site unique. After digestion with BamHI/XbaI, a linker containing an SphI site was introduced: GATCG-CAGC<u>ATG</u>C(CTAG) (SEQ ID NO:13). (Portion in parentheses indicates sequence on the complementary strand of the oligonucleotide.) The resulting modified PstI/EcoRI fragment was restored to the pCIB1711 backbone by 3-way ligation. The recombinase gene was subsequently introduced in place of the luc gene in two successive ligations because of the internal SphI site.

p1RSLuc (FIG. 4E) is a derivative of pCIB1711 in which the 31-bp RS site has been introduced between the 35S-promoter and the 35S leader of the luciferase gene. The promoter fragment between HindIII and PstI sites was first subcloned into pSGpoly7 to form pSG35S, and into the unique BamHI site an oligo pair corresponding to the following sequence with RS (bold) and a HindIII site (underlined) was ligated:

GATC<u>AAGCTT</u>TTGATGAAAGAATA
CGTTATTCTTTCATCAA(GATC) (SEQ ID NO:14) A clone whose inserted oligo was determined by sequencing to be clockwise as shown above was chosen, and its RS-containing XbaI/PstI subfragment was restored to the backbone of pCIB1711 by 3-way ligation to form p1RSLuc.

p2RSLuc (FIG. 4F) is a derivative of pCIB1711 in which synthetic RS sites have been introduced on both sides of the 35S promoter in opposite orientation, and in which the entire 35S promoter is reversed with respect to the remainder of the luc gene. The 35S-promoter subclone pSG35S described above was digested with HindIII/XbaI and an oligo pair corresponding to the following sequence with RS (bold) and a PstI site (underlined) was introduced:

AGCTA<u>CTGCAG</u>TTGATGAAAGAATA
CGTTATTCTTTCATCAA(CTAG) (SEQ ID NO:15) The resulting clone was digested with BamHI, and a second copy of RS was introduced by ligating in the oligo pair described in the previous paragraph. A clone was chosen in which the orientation of the second RS site was opposite to that of the first one (i.e. GATC<u>AAGCTT</u>TTGATGAAAGAATA
CGTTATTCTTTCATCAA(GATC) (SEQ ID NO:16) was in counterclockwise orientation). The orientation of the palindromic RS sequence is defined by the underlined central asymmetrical trinucleotide <u>CGT</u> (or <u>ACG</u> on the other strand). From the resulting 2RS promoter clone, a HindIII/PstI fragment was excised and restored to the pCIB1711 backbone by 2-way ligation, reversing the orientation of the 35S-promoter fragment, to form p2RSLuc.

3. mRNA Synthesis

The T7lucA50 and T7RecA50 plasmids (FIG. 4A and 4B) were linearized with HindIII, which cuts immediately downstream of the poly(A) stretch. Linearized DNA was phenol/chloroform extracted and then ethanol precipitated. In vitro transcription of linearized DNA was carried out using the T7 polymerase from the T7 Cap-Scribe kit containing [m⁷G(5') ppp(5')] (Boehringer). For some experiments, the transcription product was immediately treated with RNase free DNase (0.03 u/ml Worthington Biochemical) in the presence of rRNasin (1 u/ml, Promega) for 5 min, 37°, and finally phenol/chloroform extracted and ethanol precipitated. The integrity and concentration of mRNA were determined by agarose gel electrophoresis.

4. Sterilization of biolistic supplies

Gold particles (1.0 μm—Biorad, 0.3 μm—Heraeus) were sterilized by placing 60 mg particles in 100% ethanol and 0.1% DEPC. Particles were rinsed 3 times with RNase-free water and then resuspended in 1 ml RNAse-free water or 1 ml RNAse-free 50% glycerol solution. Aliquots of 50 μl prepared particles were used for 6 shots. Macrocarriers were submerged in 100% ethanol and 0.1% DEPC, then rinsed 3 times in 100% ethanol and air dried. Stopping screens were autoclaved.

5. Nucleic Acid Precipitation

DNA was precipitated onto a 50 μl suspension of gold particles (60 mg/ml) following the instructions of BioRad. mRNA was precipitated onto a 50 μl suspension of gold particles under various conditions indicated in the text. All precipitation reagents were RNase free and were added to gold particle suspension during continuous vortexing at 4° C. After all reagents were added, vortexing was continued for 3 minutes, after which the particles were sedimented by brief microcentrifugation (1 min). The supernatant was removed and the particles were washed once with cold 100% ethanol, and resuspended in 60 μl 100% ethanol. This mixture was vortexed, and 10 μl aliquots were pipetted onto a macrocarrier disk and allowed to air dry in a laminar flow hood.

6. Microprojectile Delivery to Plant Cells

Microprojectiles were delivered to plant cells by a particle accelerator (PDS-1000/He device) using 1100–1550 psi rupture disks with the sample positioned 5.5 cm from the launch assembly. A 100 μm mesh stainless steel screen was placed halfway between the stopping plate and the tissue. Target plates were bombarded 1 time (tobacco cells) or 2 times (maize cells).

7. Luciferase Assays

Luciferase was assayed in tissue extracts with the luciferase assay system of Promega according to the recommendation of the supplier. Luciferase activity is expressed as light units detected by an Analytical Luminescence model 2001 Luminometer integrated over 10s at 25° C. For calculation of specific activity, protein concentration was determined using the Bio-Rad protein assay kit.

D. Results

1. Precipitation of Intact mRNA onto Gold Particles

In order to optimize mRNA delivery and subsequent expression, several methods of precipitating mRNA onto gold particles were tested and the condition and recovery of mRNA in precipitate and supernate were analyzed by electrophoresis on agarose gels. Fractions were designated "supernatant" (pipetted directly from the initial precipitation reaction), "gold" (gold particles suspended in water after mRNA precipitation) and "water eluate" (the supernatant after mRNA-coated gold particles suspended in water were centrifuged). The water eluate was examined to determine how readily the precipitated mRNA might redissolve after delivery to the plant cell.

When subjected to the DuPont DNA precipitation method of 1.0M CaCl$_2$ and 16 mM spermidine, mRNA was severely degraded (data not shown). Spermidine free base is likely to cause alkaline hydrolysis of RNA. Accordingly, various concentrations of CaCl$_2$ (1.0M, 0.3M and 0.07M) without spermidine were tested for precipitation of mRNA onto gold particles. 1.0M CaCl$_2$ gave superior results and overnight incubation of gold particles with RNA in 1.0M CaCl$_2$ at −20° was found to improve efficiency to 90–100%. The mRNA dissolved off the particles into the water eluate more readily after two ethanol washes than after only one, presumably because of CaCl$_2$ removal.

2. Transient Expression of Luciferase mRNA after Biolistic Delivery

To determine whether mRNA precipitated onto gold particles in this manner survives the biolistic delivery process and can function transiently in plant cells, in vitro synthesized luciferase mRNA was delivered to plant cells. The CaMV35S leader sequence and a poly (A) tail with 50 adenylate residues were incorporated into the T7LucA50 template construct in an effort to enhance luciferase expression in plant cells. Capped luciferase mRNA was precipitated onto gold particles with 1.0M CaCl2 and incubated overnight at −20° C., and particles were bombarded into maize and tobacco suspension cells. Luciferase assays were performed at 2, 6 and 24 hours after delivery. Results are shown in Table 3 below. By 2 hours, significant luciferase activity was detected. Activity increased by 6 hours, but decreased by 24 hours. In contrast, transient expression of the DNA plasmid containing the 35S-luciferase gene (pCIB1711), precipitated onto gold particles by the BioRad DNA regimen, was highest at 24 hours.

TABLE 3

Demonstration of luciferase activity in tobacco cells and maize cells after bombardment with luciferase RNA. Results of luciferase activity measurements (Light Units/μg protein) 2 hrs, 6 hrs, and 24 hrs after bombardment are shown.

|  | Description | Time | Tobacco | Maize |
| --- | --- | --- | --- | --- |
| Luciferase RNA | RNA | 2 hrs | 980 | 2100 |
|  |  | 6 hrs | 5300 | 2400 |
|  |  | 24 hrs | 700 | 400 |
| pCIB1711 DNA | luciferase DNA | 2 hrs | 78500 | 1000 |
|  |  | 6 hrs | 198000 | 6900 |
|  |  | 24 hrs | 1034600 | 14800 |
| T7-LucA50 DNA | template alone | 6 hrs | 30 | 300 |
| No RNA-DNA |  | 24 hrs | 0 | 100 |

Figure 4F:
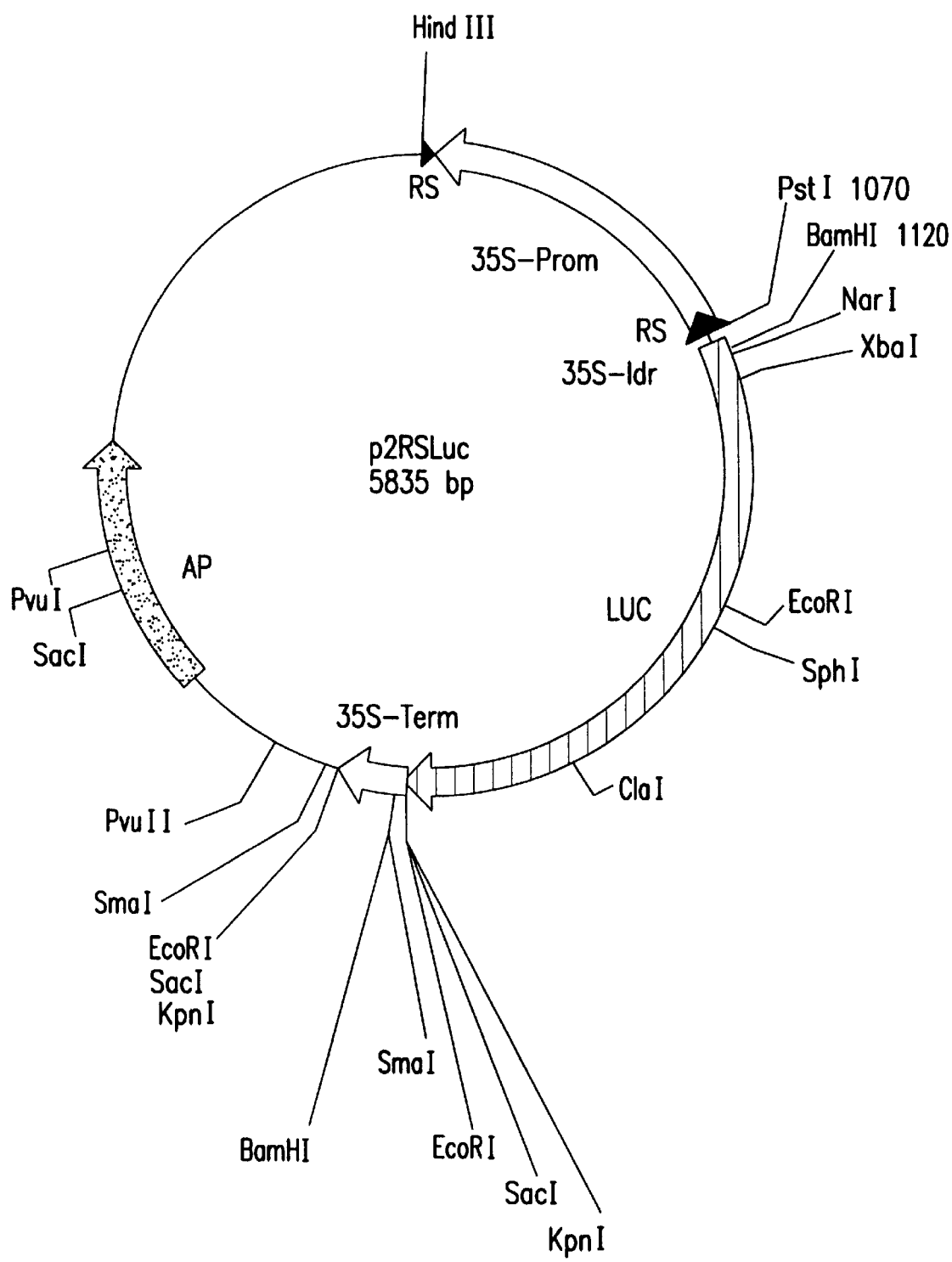
Figure 6:
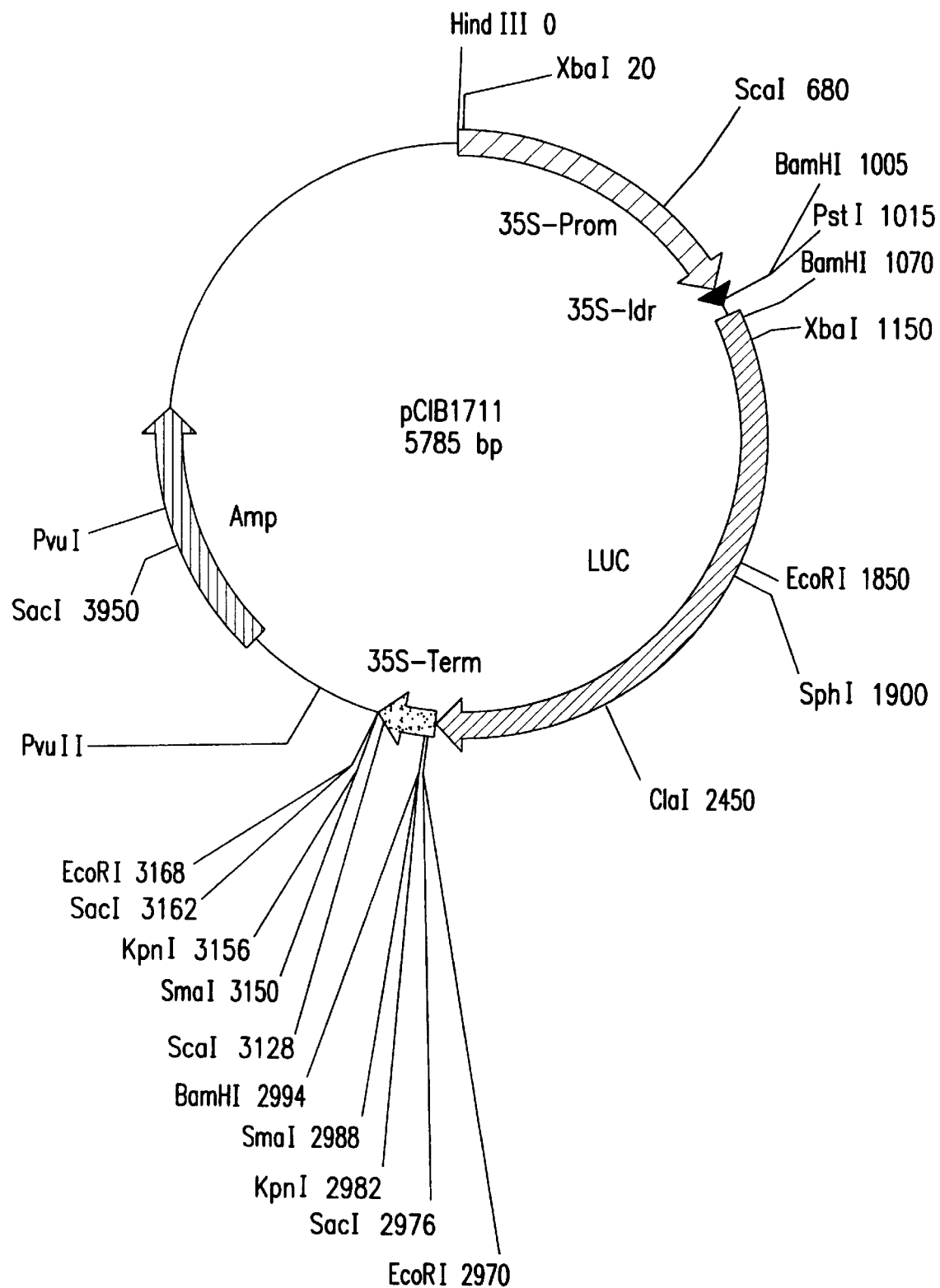
FIG. 6: Schematic representation of plasmid pCIB1711 (see Example 1).
Figure 7:
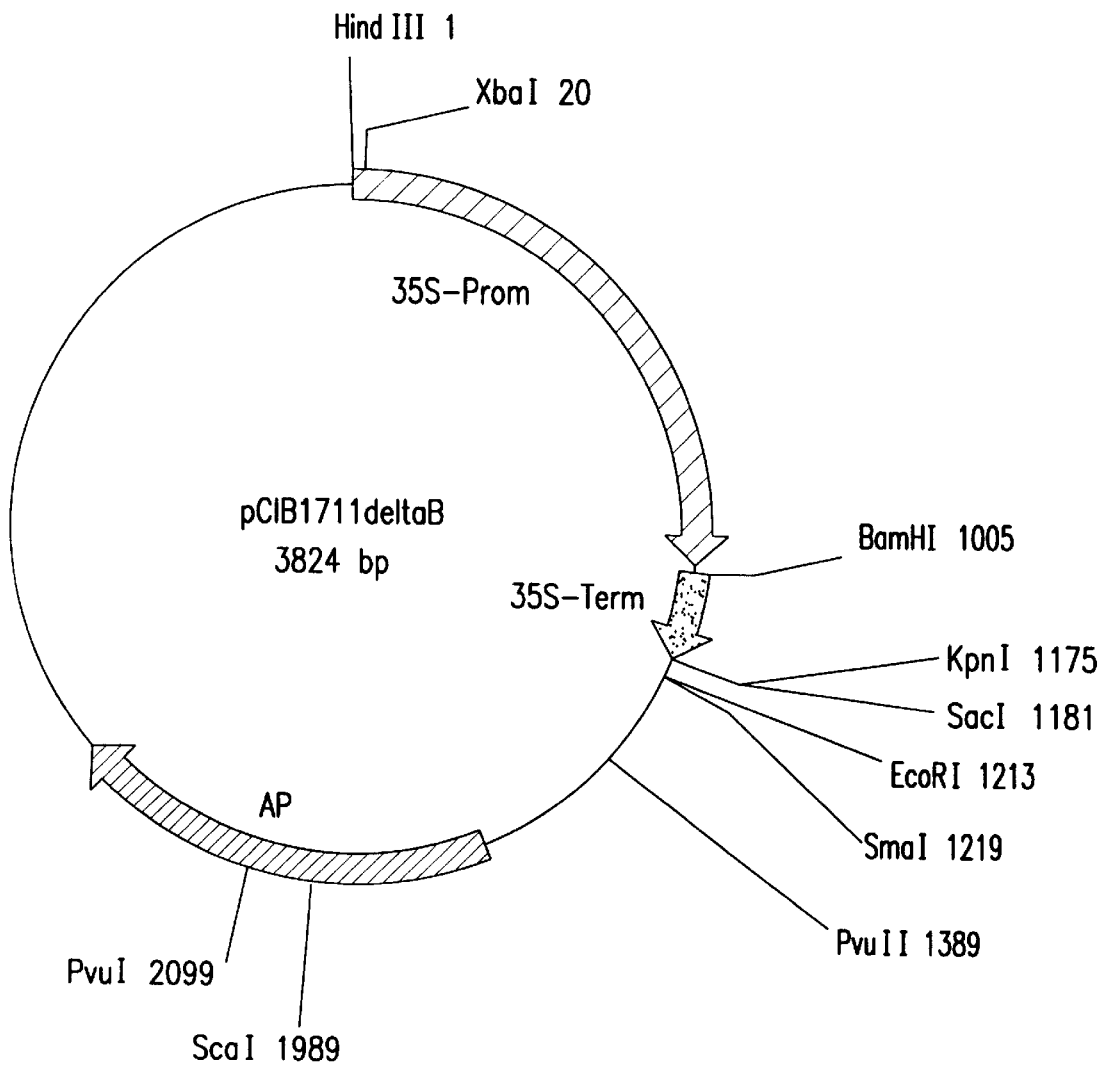
FIG. 7: Schematic representation of plasmid pCIB1711deltaB (see Example 7).
Figure 8:
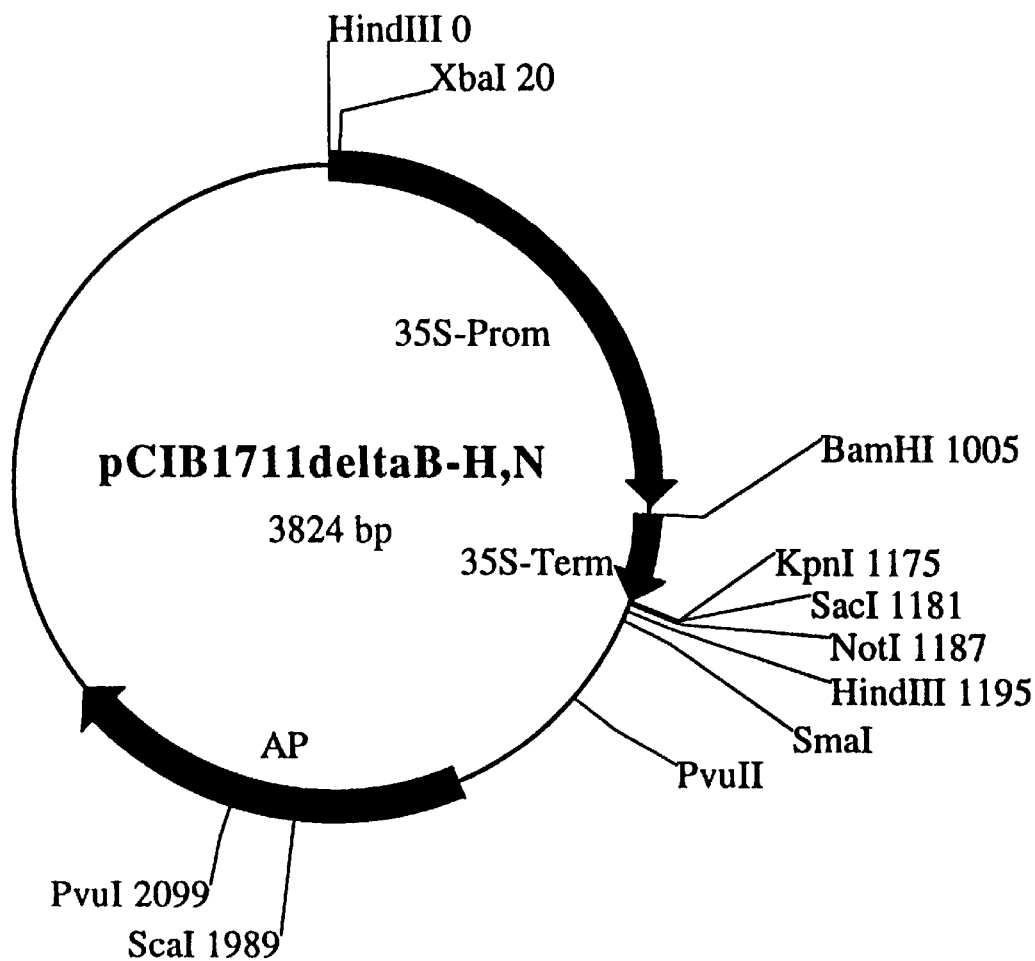
FIG. 8: Schematic representation of plasmid pCIB1711deltaB-H,N (see Example 7).
Figure 9:
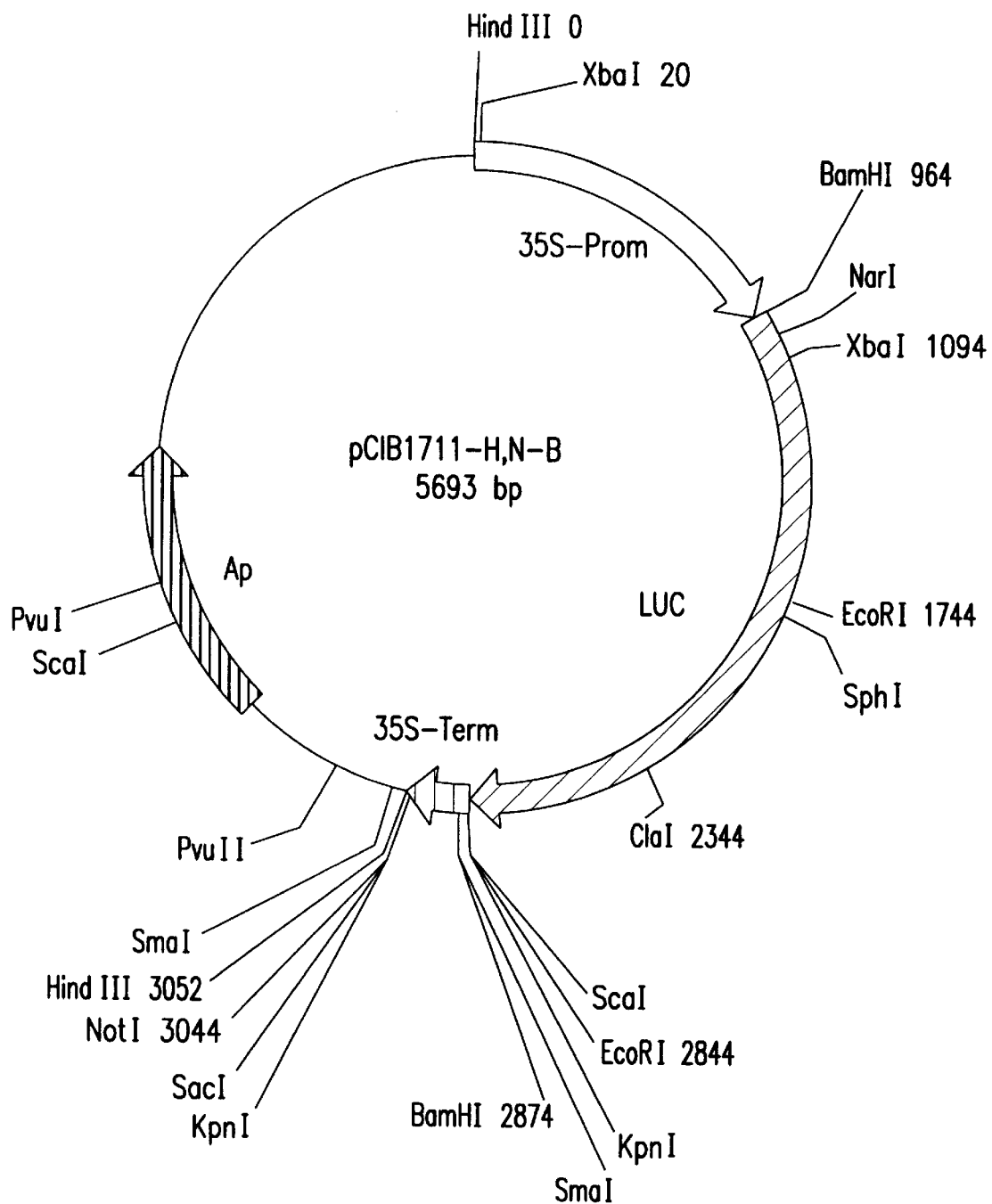
FIG. 9: Schematic representation of plasmid pCIB1711-H,N-B (see Example 7).
Figure 10:
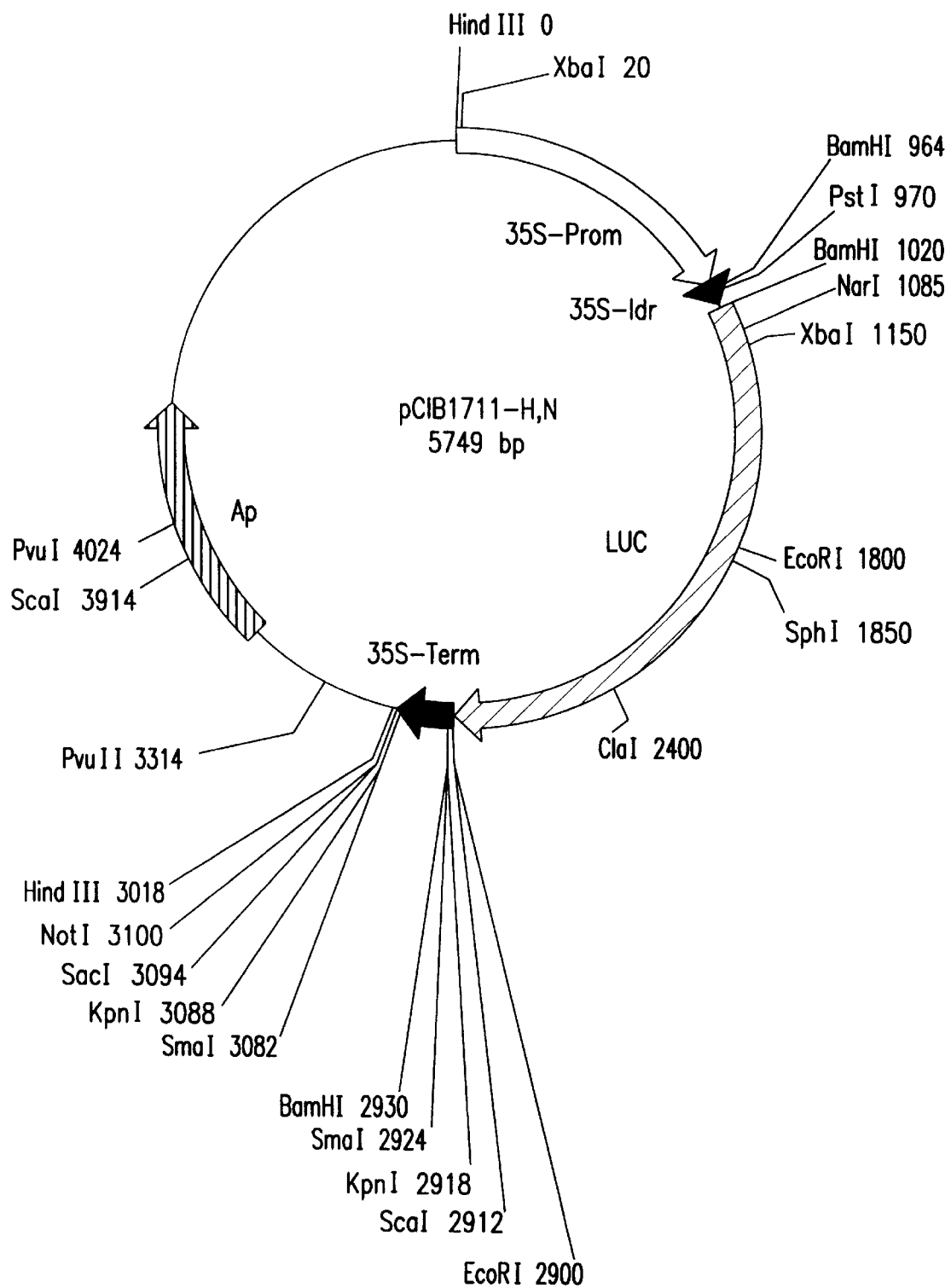
FIG. 10: Schematic representation of plasmid pCIB1711-H,N (see Example 7).
Figure 11:
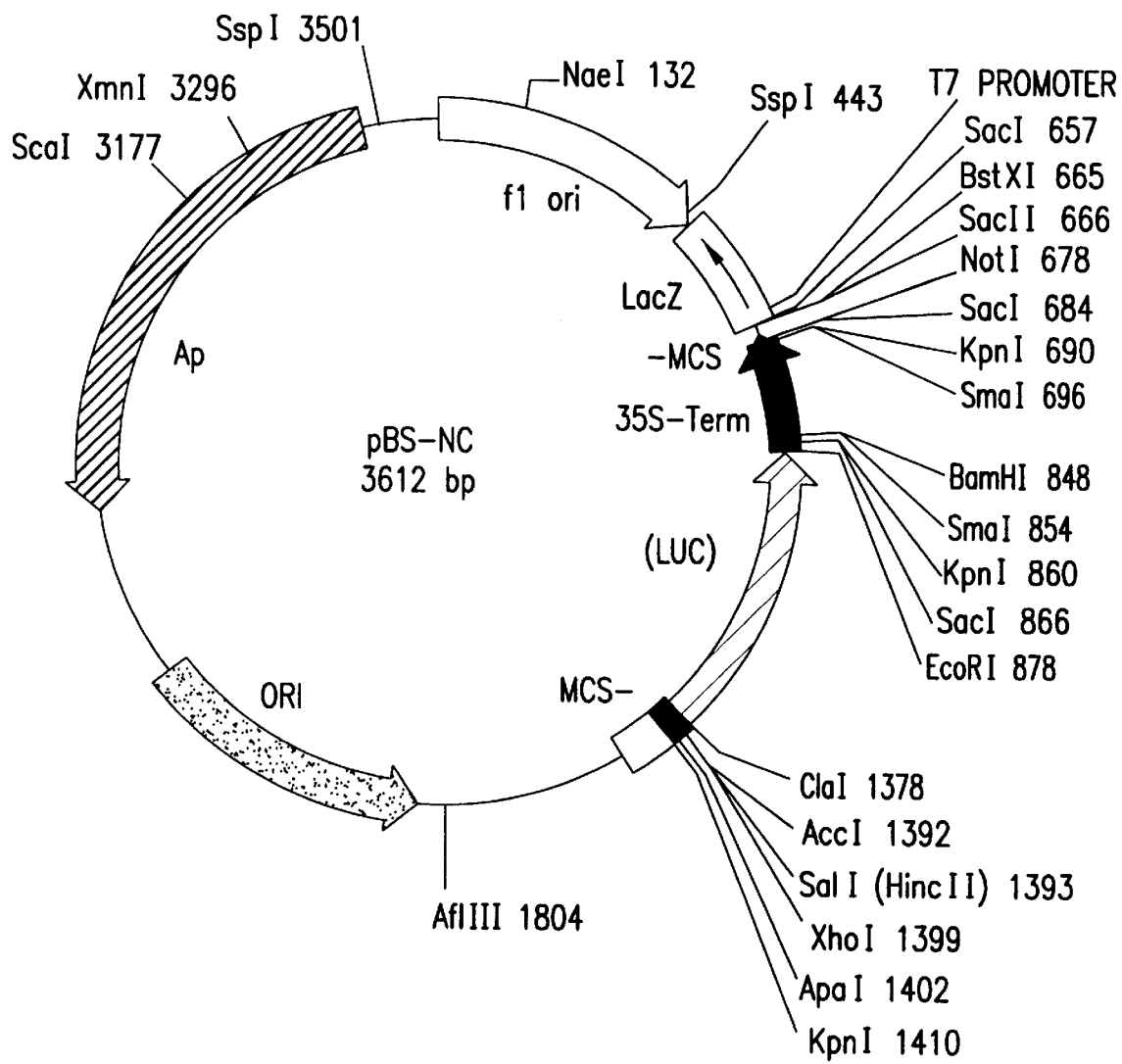
FIG. 11: Schematic representation of plasmid pBS-NC (see Example 7).
Figure 12:
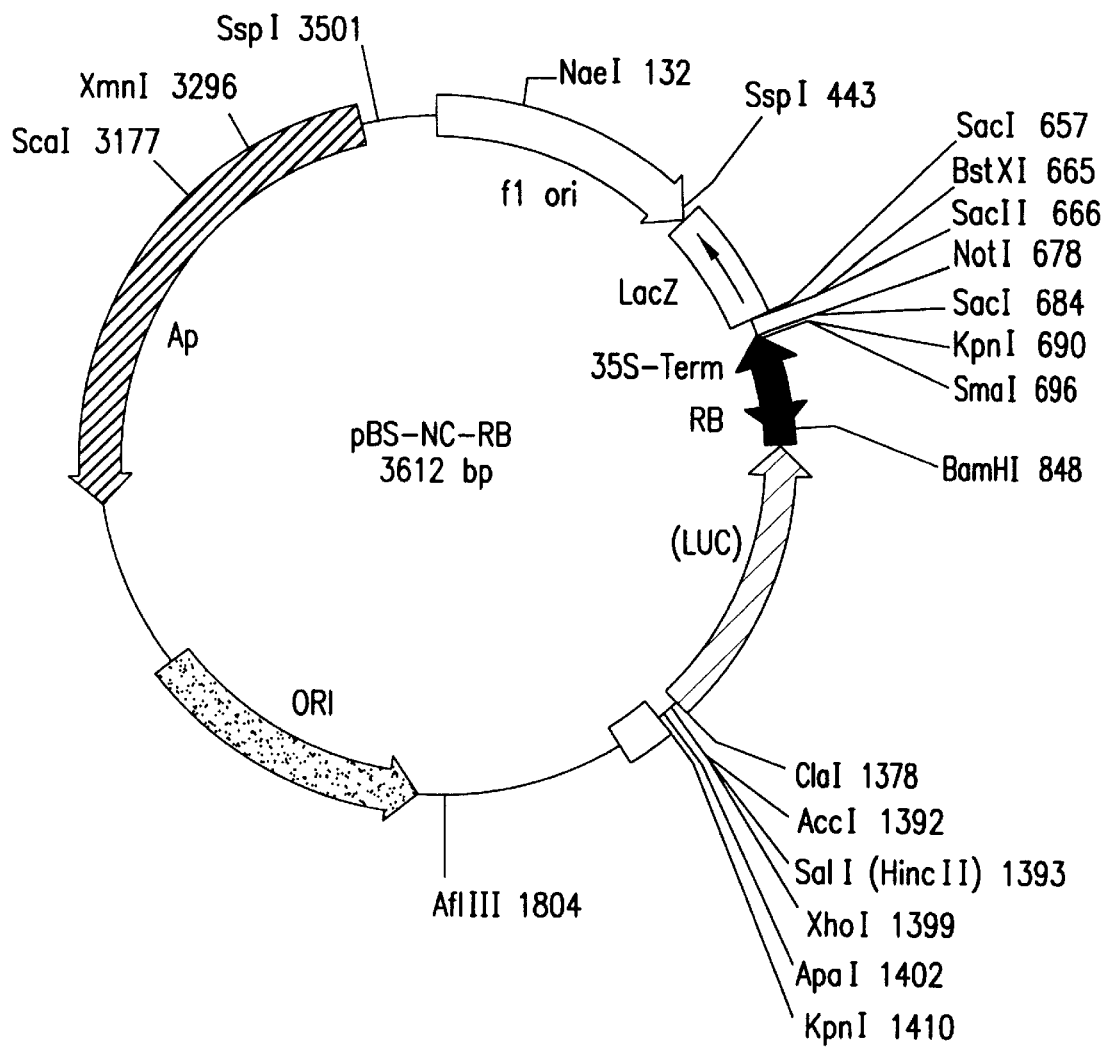
FIG. 12: Schematic representation of plasmid pBS-NC-RB (see Example 7).
Figure 13:
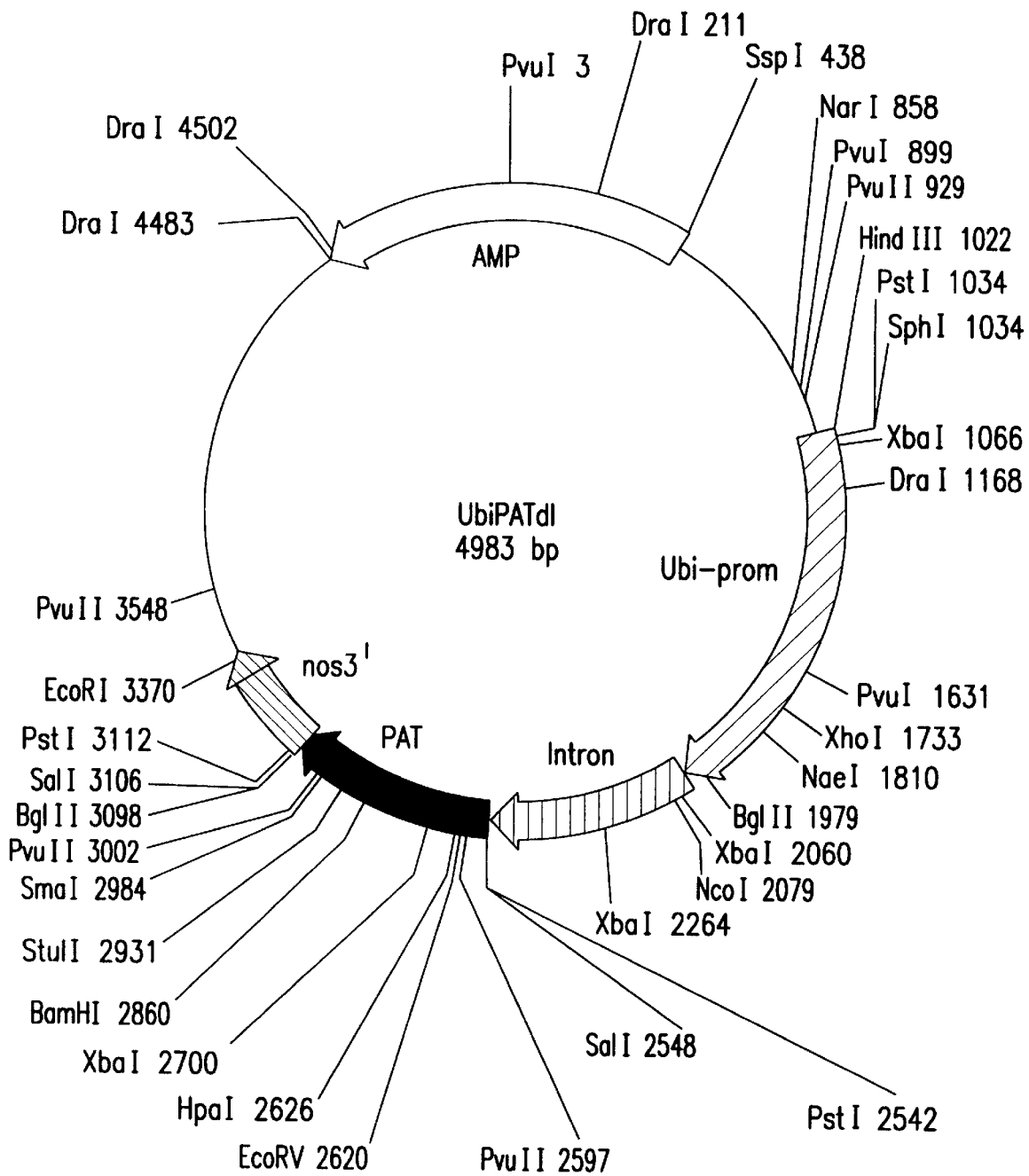
FIG. 13: Schematic representation of plasmid UbiPATdI (see Example 7).
Figure 14:
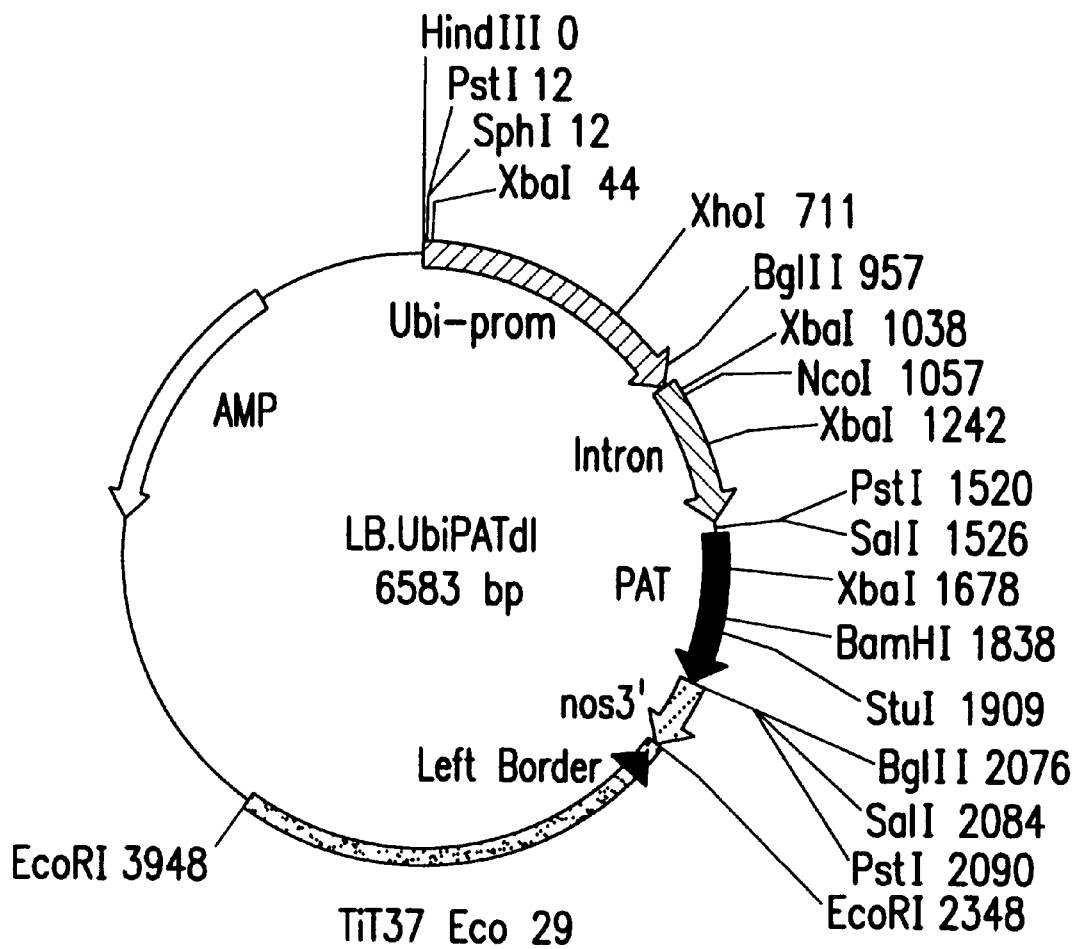
FIG. 14: Schematic representation of plasmid LB.Ubi-PATdI (see Example 7).
Figure 15:
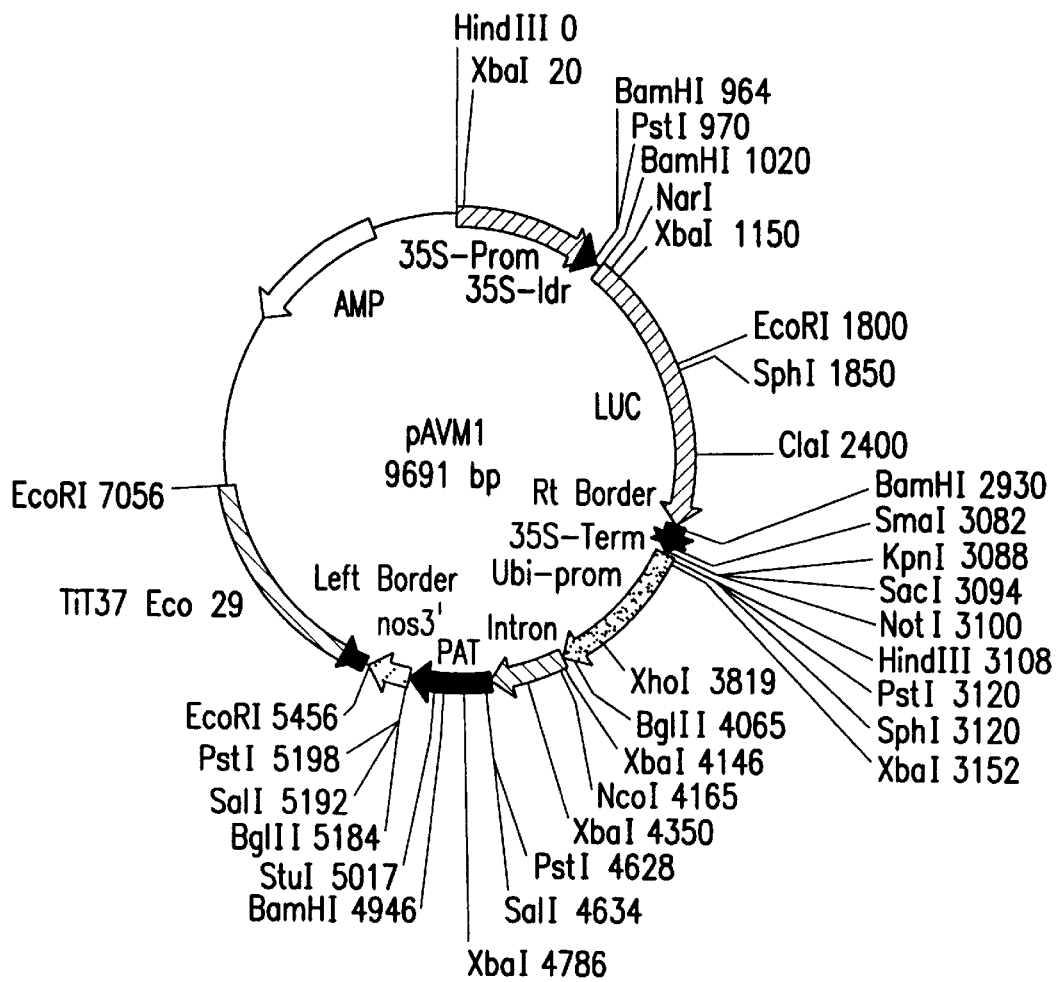
FIG. 15: Schematic representation of plasmid pAVM1 (see Example 7).
Figure 16:
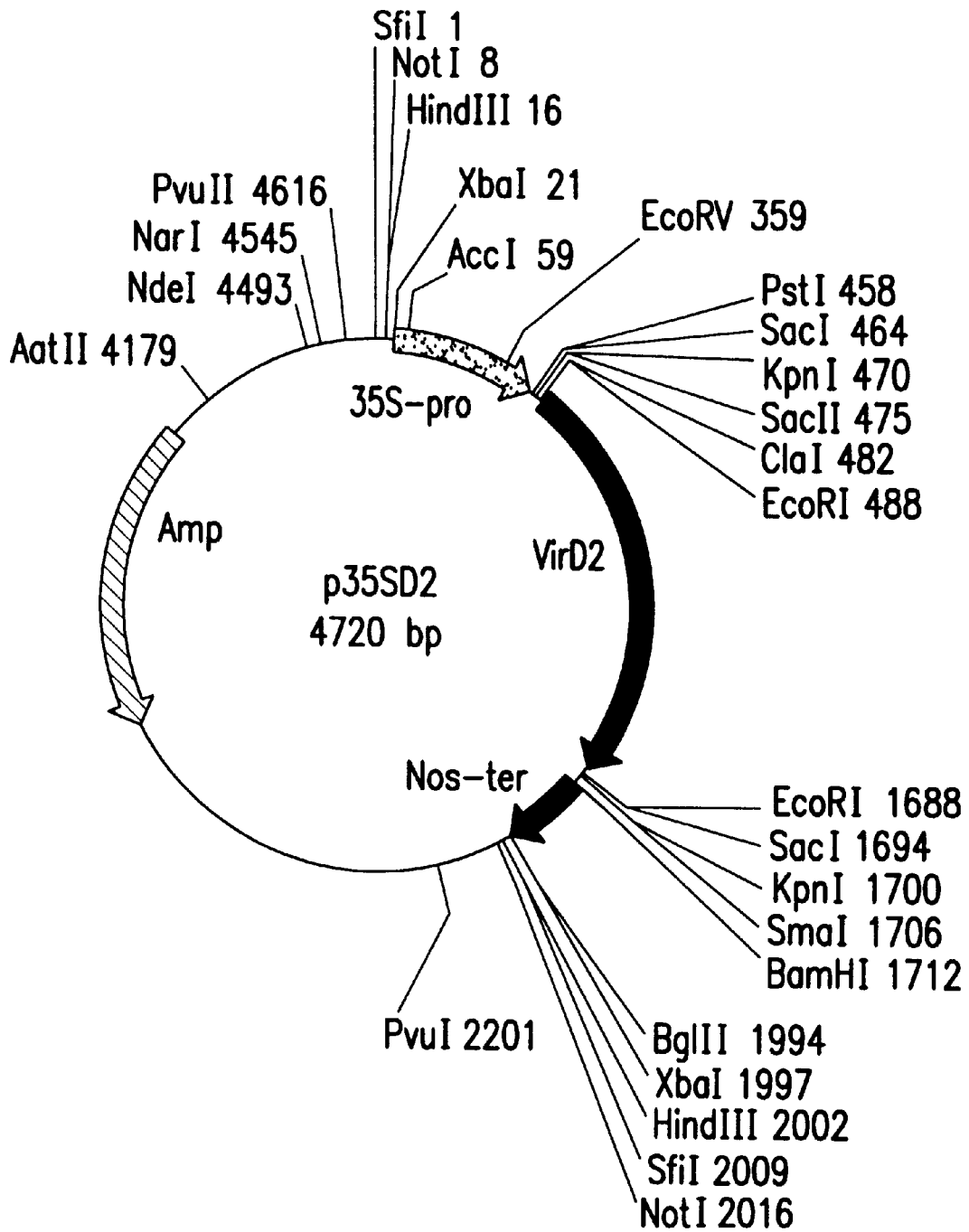
FIG. 16: Schematic representation of plasmid p35SD2 (see Example 8).
Figure 17:
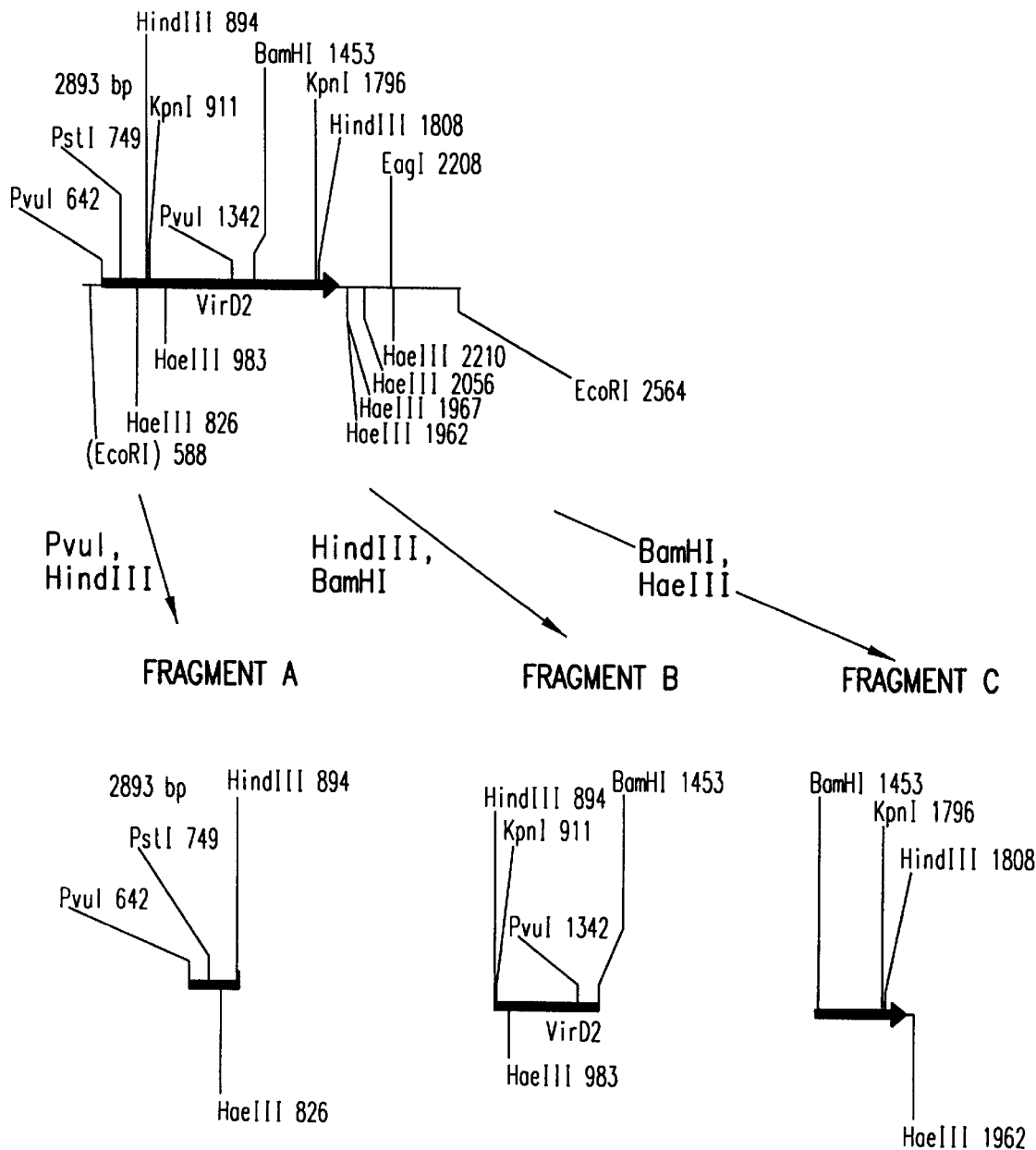
FIG. 17: Schematic representation of the preparation of fragments A–C from the EcoR1 fragment of p35SD2 containing the virD2 open reading frame (see Example 8).
Figure 18:
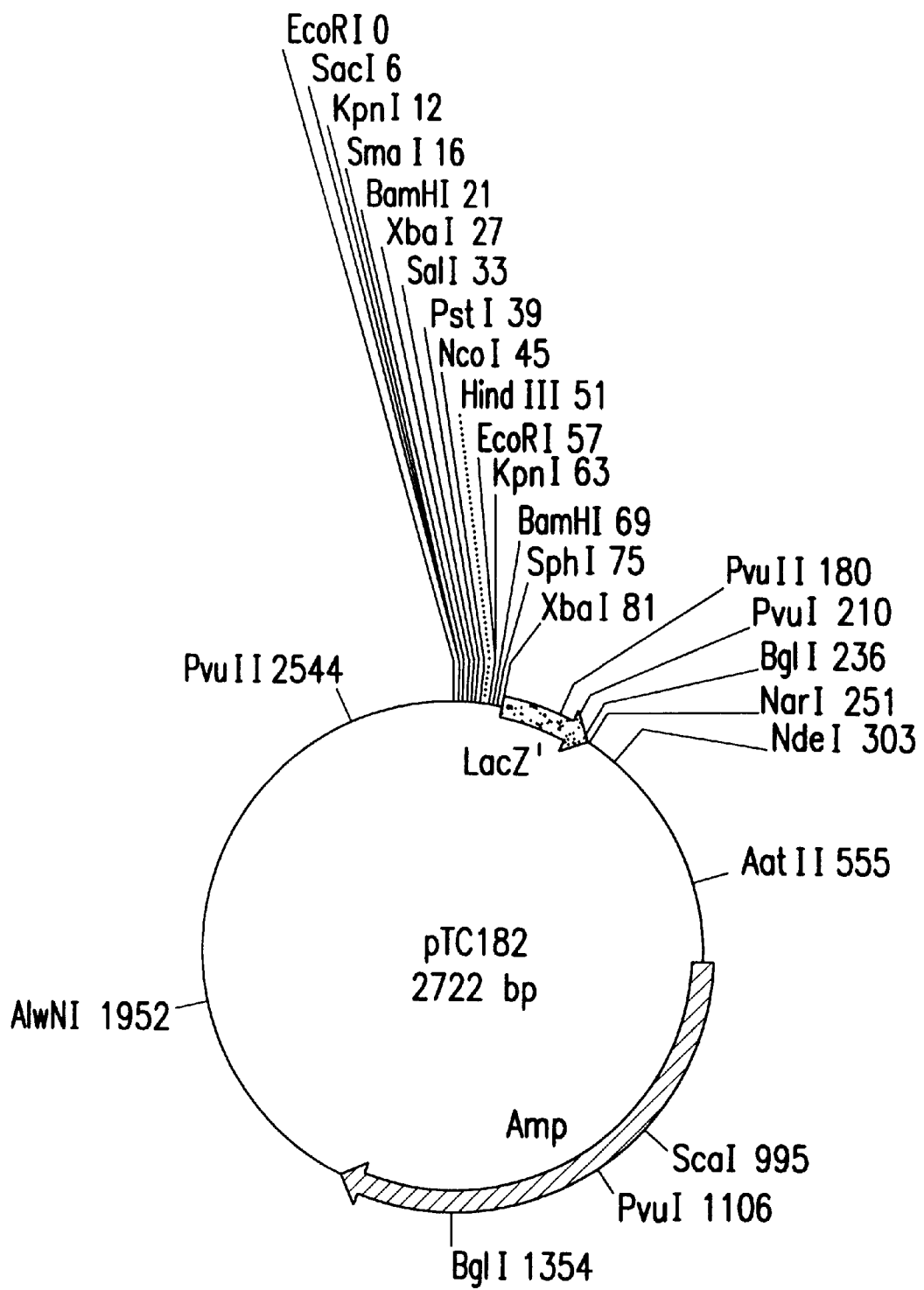
FIG. 18: Schematic representation of plasmid pTC182 (see Example 8).
Figure 19:
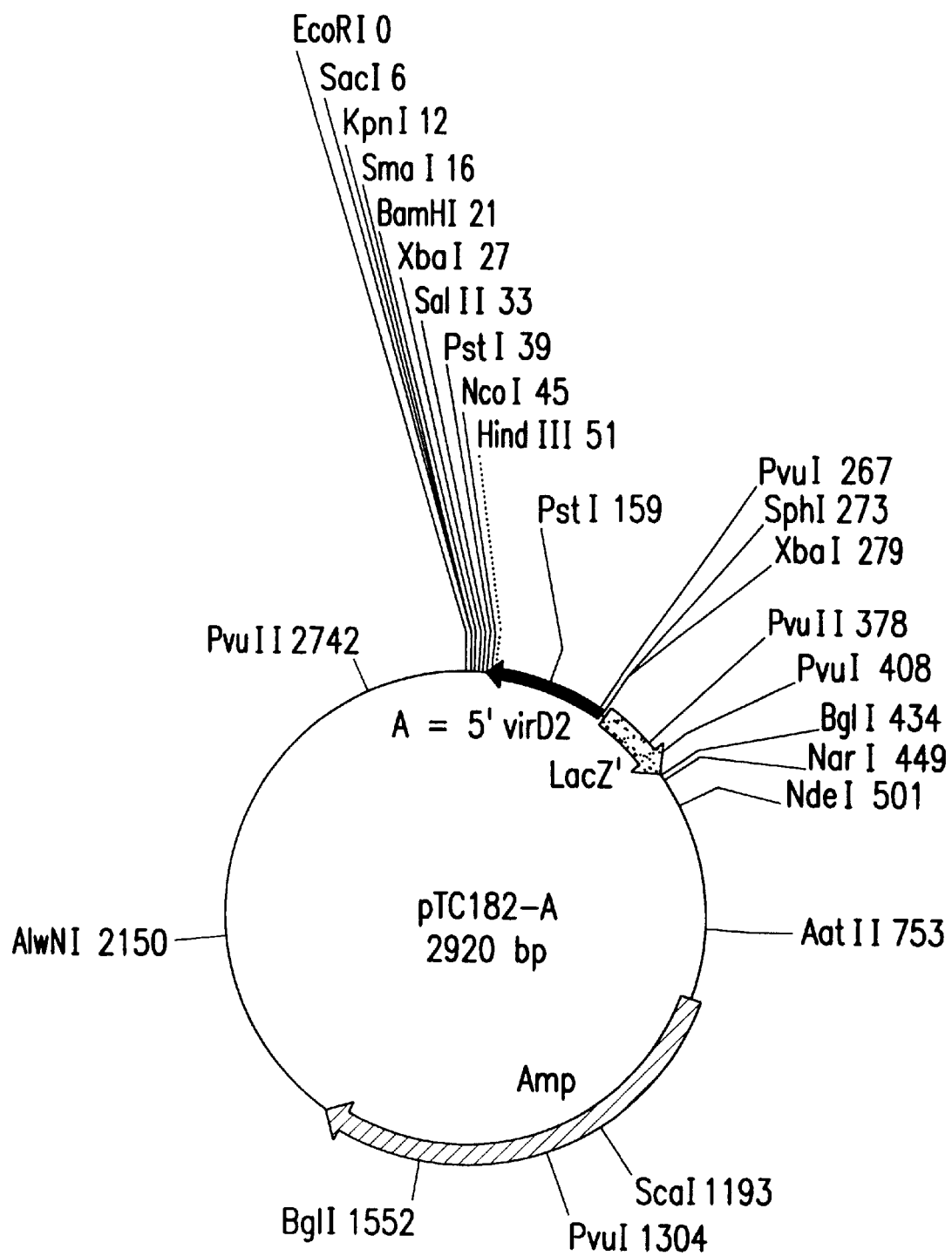
FIG. 19: Schematic representation of plasmid pTC182-A (see Example 8).
Figure 20:
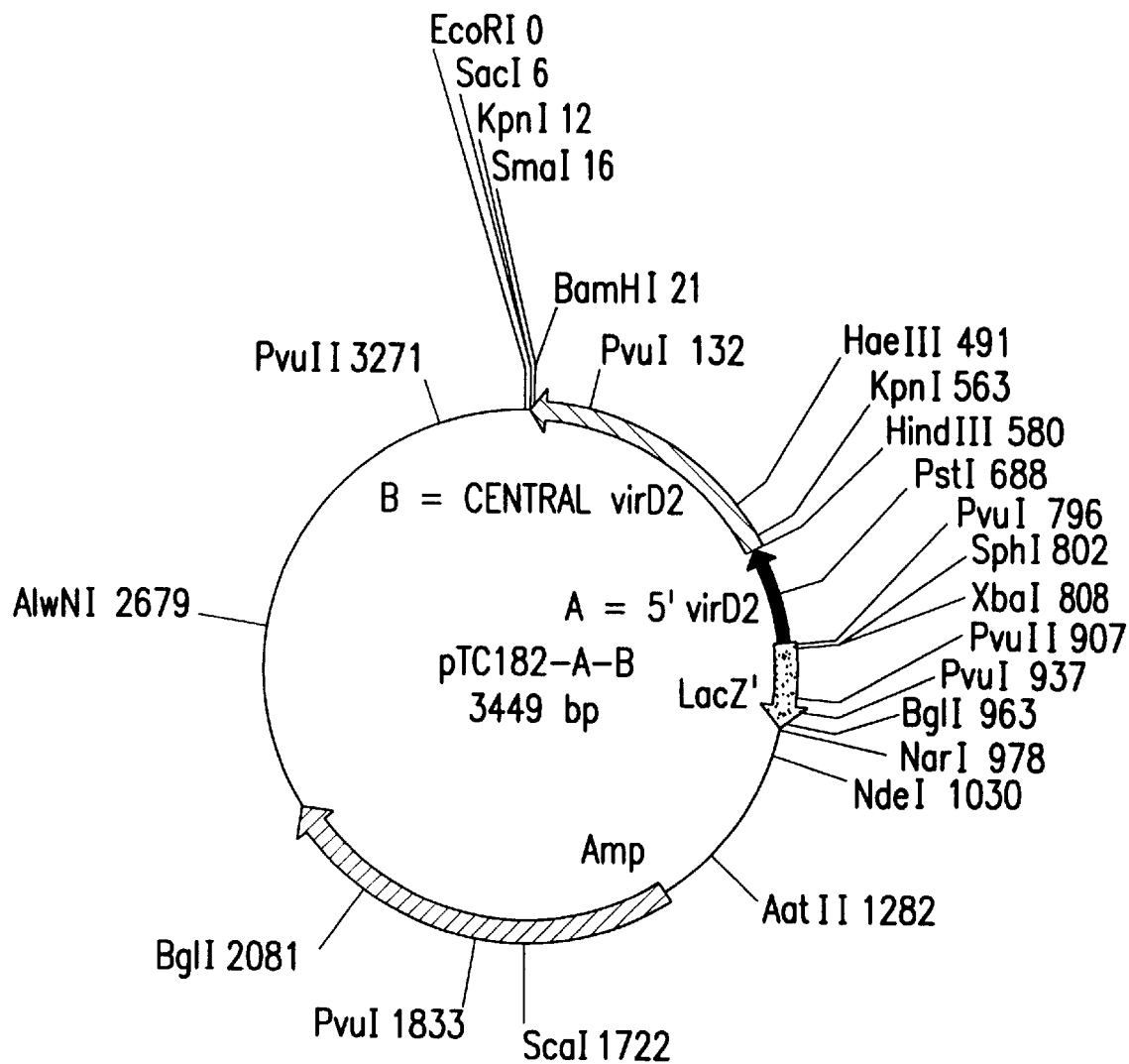
FIG. 20: Schematic representation of plasmid pTC182-A-B (see Example 8).
Figure 21:
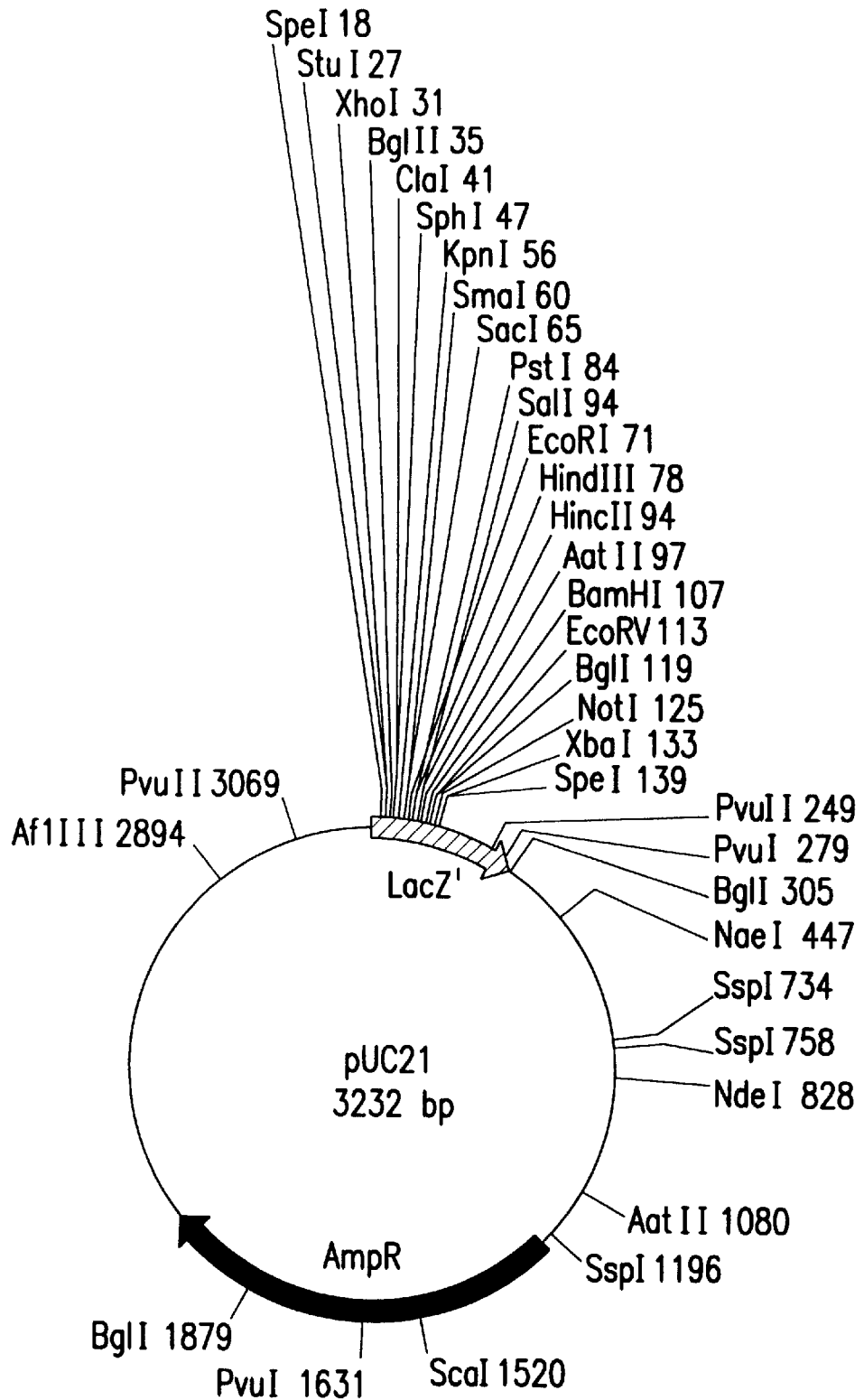
FIG. 21: Schematic representation of plasmid pUC21 (see Example 8).
Figure 22:
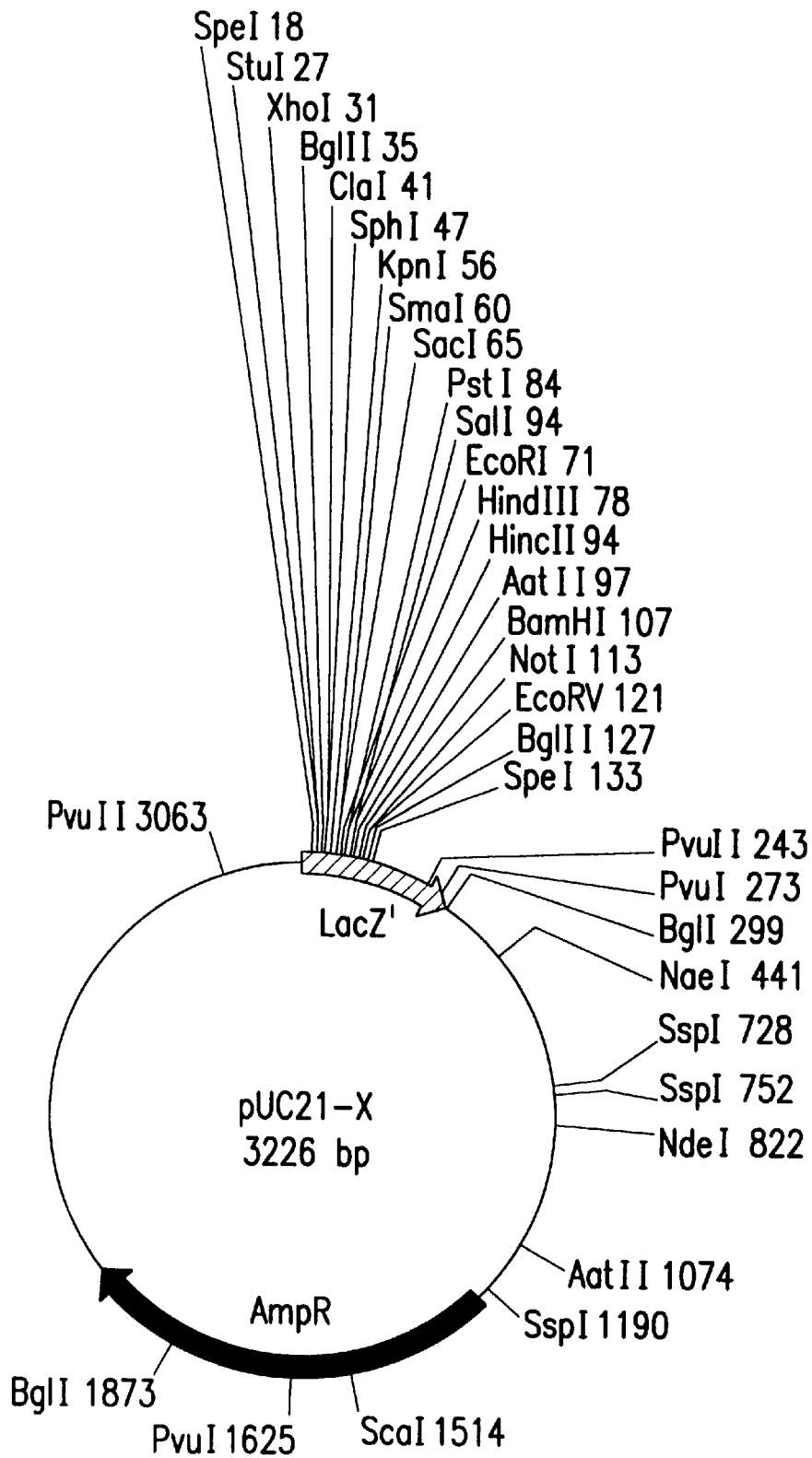
FIG. 22: Schematic representation of plasmid pC21-X(see Example 8).
Figure 23:
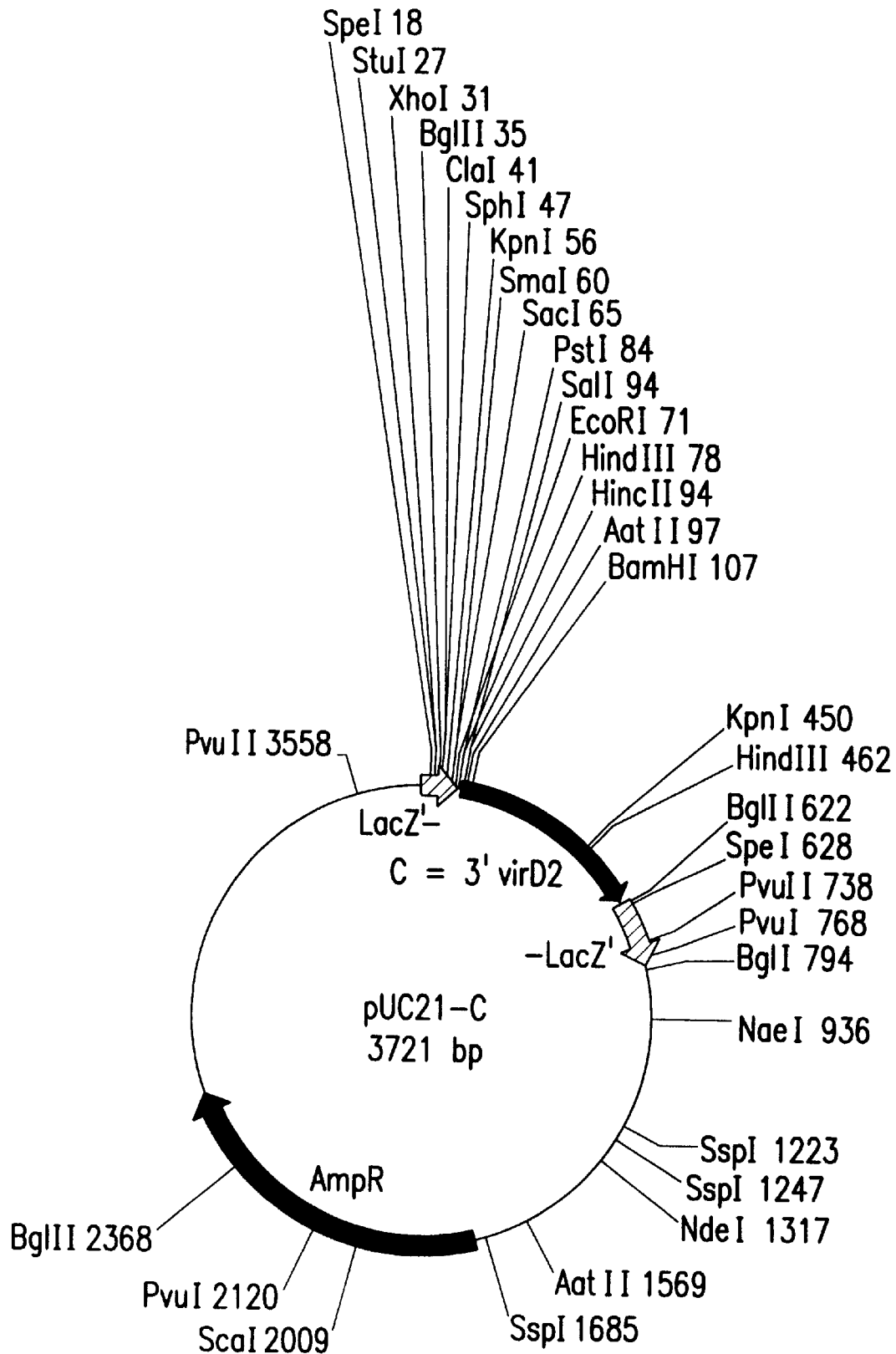
FIG. 23: Schematic representation of plasmid ppUC21-C (see Example 8).
Figure 24:
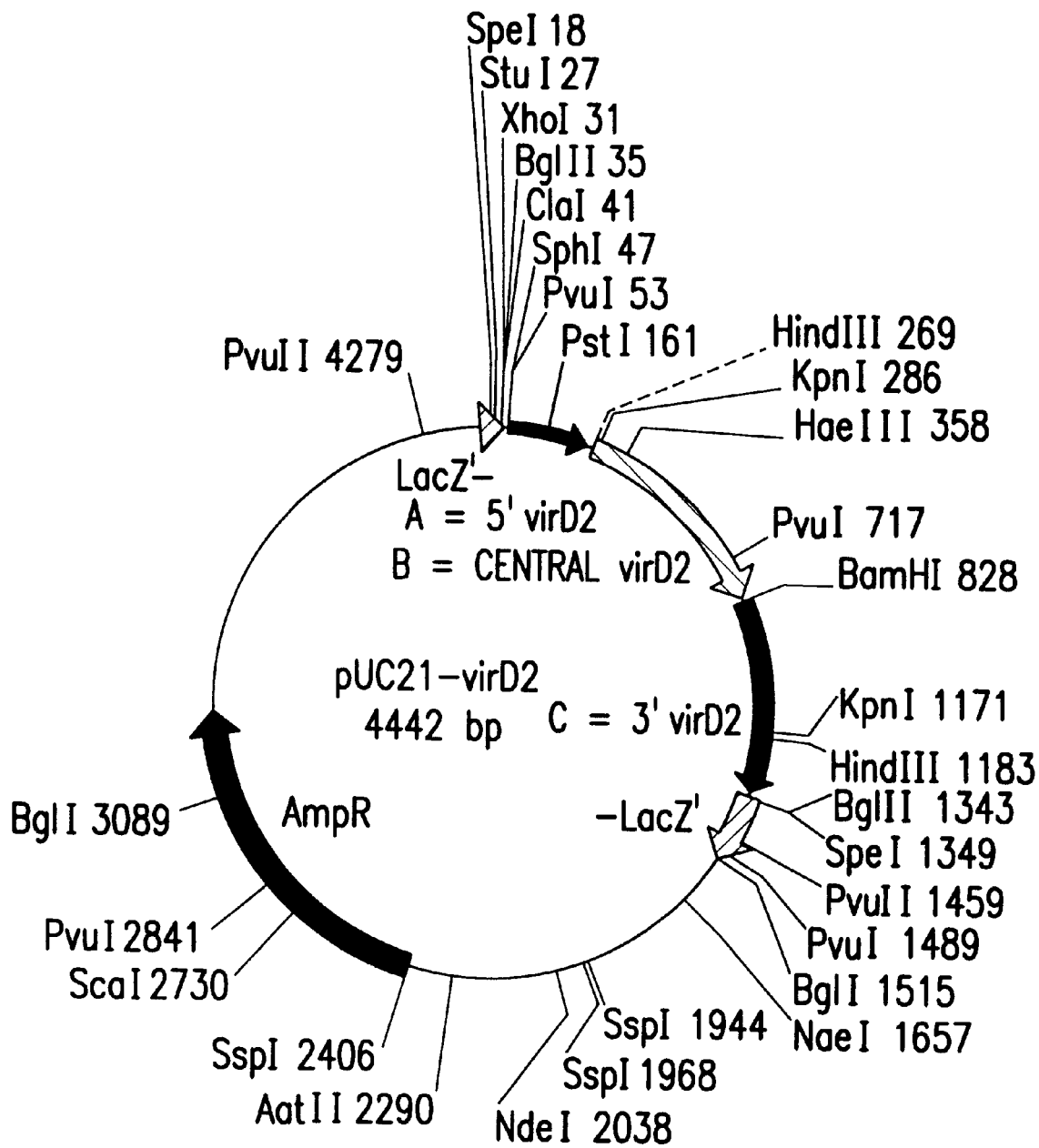
FIG. 24: Schematic representation of plasmid pUC21-virD2 (see Example 8).
Figure 25:
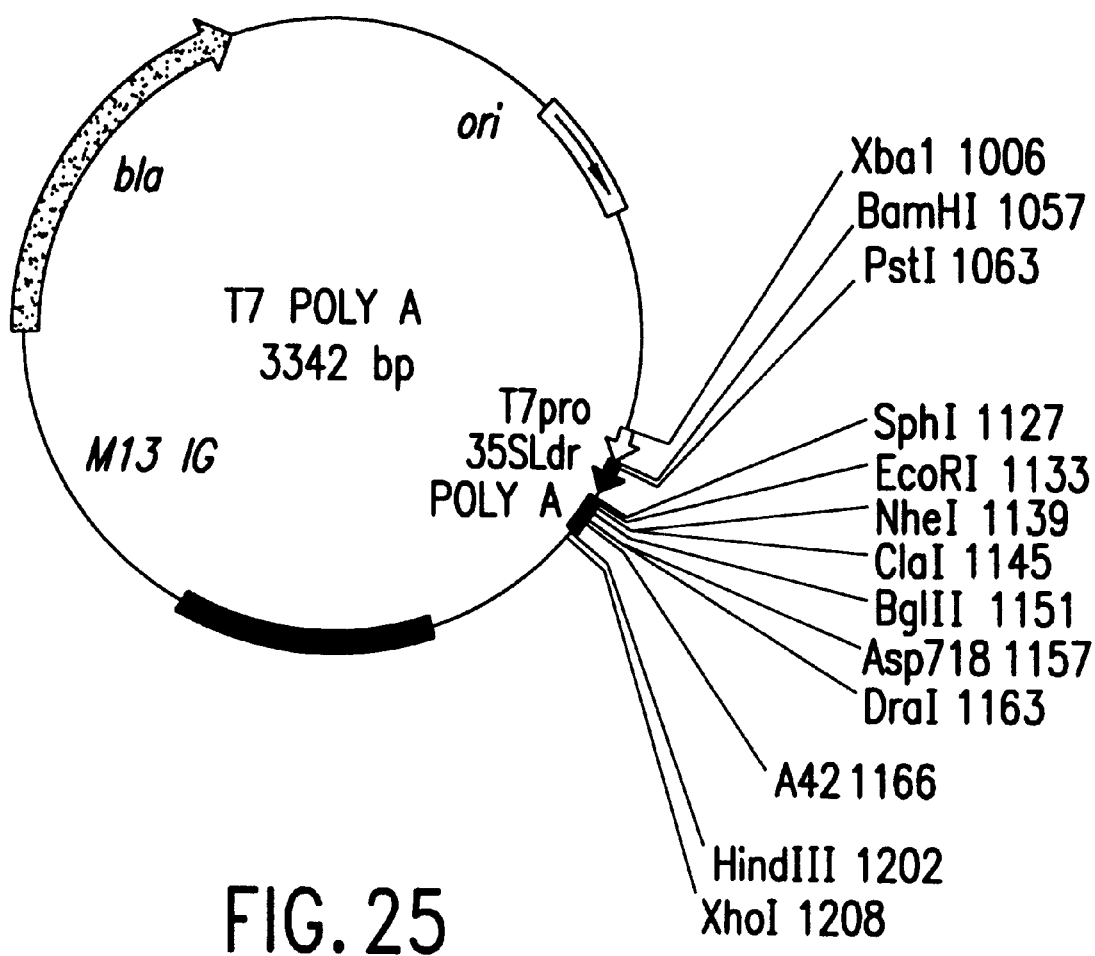
FIG. 25: Schematic representation of plasmid T7polyA (see Example 8).
Figure 26:
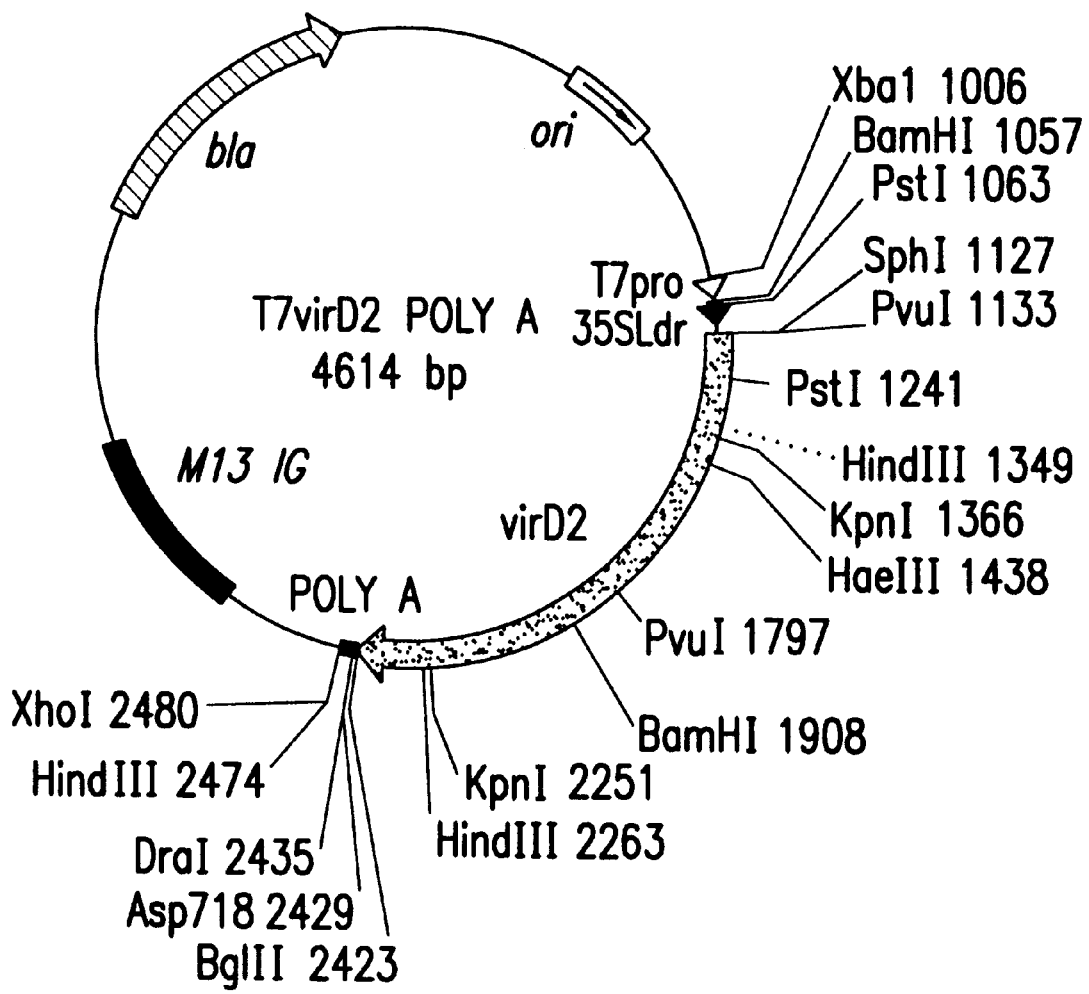
FIG. 26: Schematic representation of plasmid T7virD2polyA (see Example 8).

3. Demonstration that the R/RS Recombinase System Functions in Maize: an Inverted Promoter is Flipped to turn on Luciferase Transient Expression In order to test whether the site-specific recombinase system R/RS, from *Z. rouxii*, would function in maize as it has been reported to function in tobacco (Onouchi et al., 1991), a double transient expression assay was used in which R-recombinase, transiently expressed in maize cells, is required to flip a promoter in order to turn on transient expression of a codelivered cryptic luciferase gene. As a positive control, the double transient assay was tested in tobacco cells. By microprojectile bombardment, the pRec plasmid (FIG. 4D) containing a 35S-recombinase gene was codelivered to maize cells with the cryptic luciferase plasmid, p2RSLuc (FIG. 4F). Flipping the promoter of p2RS would leave a copy of RS (31 bp) between promoter and luc gene whose impact on luc expression was unknown. We therefore also constructed a positive control plasmid, p1RSLuc was therefore also constructed (FIG. 4E), to simulate the expected product of p2RSLuc inverted by recombinase. p1RSLuc contains the CaMV35S promoter correctly oriented but separated by a single RS site from the leader and the luciferase coding sequence. p1RSLuc was found to be expressed at a level similar to that of pCIB1711 in both tobacco and maize (data not shown); thus the RS "footprint" in the gene has only a minor effect on luc expression.

A mixture of plasmids p2RSLuc and pRec, as well as control plasmids p2RSLuc alone, p1RSLuc and p1RSLuc plus pRec, were precipitated onto gold particles by the BioRad protocol and bombarded into tobacco and maize cells (Table 4). While R-recombinase turned on the luc gene in tobacco with at least 4% efficiency by 24 hours (26,000 vs. 597,000 light units/μg protein) the process appeared far less efficient in maize with only 0.27% efficiency (53 vs. 20,000 light units/μg protein). The very low activity detected in maize was indeed found to be significant and reproducible. The feature limiting recombinase activity in maize in this experiment might be nuclear (slow transcription, false splice sites, failure of mRNA to exit the nucleus) or cytoplasmic events (translational stalling, rare codon usage, mRNA instability, etc.). If the problem were nuclear, we anticipated that it could be circumvented by biolistic delivery of recombinase mRNA, which presumably would introduce the transcript directly into the cytoplasm.

TABLE 4

Recombinase activity in tobacco and maize cells after bombardment. Results of the mean and the standard deviation of the luciferase activity (Light Units/μg protein) from 6 replicates of tobacco cells and 3 replicates of maize cells.

|  | Tobacco | Maize |
| --- | --- | --- |
| no DNA | 16 | <1 |
| p2RSluc | 1300 ± 2300 | 4 ± 1 |
| p2RS + pRec | 26100 ± 2600 | 53 ± 4 |
| p1RSluc | 852000 ± 91000 | 15700 ± 4100 |
| p1RSluc + pRec | 597000 ± 122000 | 20700 ± 2600 |

The target site for the Z. rouxii recombinase has previously been narrowed to a 58 bp region (Matsuzaki et al., Molecular and Cellular Biology 8, 955–962 (1988)) including the 31 bp palindromic sequence employed here. Our results show that the 31 bp palindrome is sufficient to allow R-gene-mediated flipping of the promoter of our cryptic luciferase construct. Thus this abbreviated RS sequence is sufficient for site-specific recombination in both tobacco and maize.

4. Transient Expression of Luciferase DNA via Recombinase mRNA Activity

Recombinase mRNA was co-precipitated with p2RSLuc DNA onto gold particles under conditions favoring RNA recovery: 1.0M $CaCl_2$ and incubation overnight at −20° C. The particles were bombarded into maize cells and luciferase activities were measured 2 and 24 hours later. Results are shown in Table 5 below. Luciferase expression was negligible at 2 hours post-bombardment. By 24 hours, luciferase expression was evident for both the mRNA recombinase treatment and 35S-recombinase DNA acting on the 2RS cryptic luciferase plasmid. The inversion reaction as it approaches equilibrium reaches a steady-state with 50% "on" and 50% "off" orientations of the promoter. The maximum level of luciferase expression expected would thus be 50% that of p1RSLuc activity. The mRNA-driven flipping achieved the surprisingly high efficiency of 67% of that theoretical maximum. The efficiency of the DNA-driven inversion was also improved significantly, however, the extremely low level of p1RSLuc expression indicated that the precipitation method developed for mRNA was very inefficient for DNA. Therefore further precipitation conditions were tested to seek an optimal compromise effective for both DNA and RNA.

TABLE 5

Demonstration of recombinase RNA activity in maize cells. The luciferase activity is expressed as light units per μg of protein and was measured 2 hours and 24 hours after bombardment.

|  | Description | 2 hours | 24 hours |
| --- | --- | --- | --- |
| p2RSluc | target alone | 5.3 | 6.4 |
| p2RSluc + T7-RecA50 | target + template alone | 4.5 | 7.8 |
| p2RSluc + Rec RNA | target + rec RNA | 6.7 | 34.8 |
| p2RSluc + Rec DNA | target + rec DNA | 5.0 | 15.6 |
| p1RSluc | positive control | 37.4 | 89.6 |

5. Efficient Co-precipitation of mRNA and DNA onto Gold Particles

In an effort to improve the efficiency of DNA co-delivery with mRNA, we re-examined using spermidine in the precipitation mix, but included the addition of Tris buffer to lower the pH and possibly avoid RNA degradation. In the presence of 50 mM Tris buffer at pH 7.5, DNA and mRNA were co-precipitated onto particles using 1.0M $CaCl_2$ and 2, 4, 10 or 16 mM spermidine. The efficiency of nucleic acid precipitation was examined by agarose gel electrophoresis as described above. Intact DNA and mRNA were precipitated efficiently onto particles at all spermidine concentrations (data not shown). The lowest concentration allowed more DNA and mRNA to re-dissolve off the particles into water, a possible advantage for transient expression and stable transformation.

In a final refinement, we varied the concentration of Tris buffer and tested for efficacy by the criterion of biological activity: Luc mRNA was precipitated using 2 mM spermidine with 5 mM (treatment A) or 50 mM (treatment B) Tris buffer pH 7.5 and was bombarded into maize cells. At 5 hours after bombardment, transient expression levels were 1,091 and 8,000 Light Units/μg protein for treatments A and B, respectively. The higher mRNA activity achieved using 50 mM Tris represents a 3–4 fold improvement over previous precipitation conditions of 1.0M $CaCl2$ and overnight incubation at −20° C. (Table 1).

Treatments A and B were used to precipitate recombinase mRNA with p2RSLuc DNA which was bombarded into maize and tobacco cells. Luciferase activity was measured at 24 hours, with results shown in Table 6 below. DNA expression improved using both 5 mM and 50 mM Tris, but the levels did not approach those achieved using the BioRad precipitation procedure (Table 4). Conditions which favor mRNA expression, 50 mM Tris, gave the highest efficiencies of recombinase activity at 18.9% and 9.4% for maize and tobacco, respectively. Although the recombinase efficiency is lower than that seen in Table 5, the higher level of DNA expression is important for achieving stable transformation. We conclude that a low concentration of spermidine, buffered with Tris, could be used with RNA and improved DNA expression.

TABLE 6

Recombinase mRNA expression in tobacco and maize cells. mRNA (4 μg/6 shots), p2RSLuc DNA (2 μg/6 shots) and p1RSLucDNA (2 μg/6 shots) were bombarded into tobacco and maize cells. mRNA synthesized from the B-glucuronidase gene was used in control experiments. Luciferase activity expressed as light Units/μg protein, was measured 24 hours post-bombardment.

|  | Tobacco | | Maize | |
| --- | --- | --- | --- | --- |
|  | 5 mM | 50 mM | 5 mM | 50 mM |
| p2RSLuc + Rec mRNA | 139 ± 2.8 | 311 ± 18 | 19 ± 1.7 | 20 ± 0.07 |
| p2RSLuc + mRNA | 57 ± 10 | 34 ± 2 | 3.5 ± 0.2 | 3.8 ± 0.9 |
| p1RSLuc + mRNA | 16683 ± 1460 | 6644 ± 1565 | 426 ± 5 | 211 ± 40 |

E. Discussion

We report here a method for co-delivery of mRNA and DNA via particle bombardment which enables transient action of the mRNA-encoded protein on the DNA molecule. Co-delivery of mRNA and DNA allows for the introduction of trans-acting functions into the cell without the possibility of permanent expression resulting from stable transformation. The mRNA-encoded recombinase is only active transiently during a brief period at the time of delivery. This approach can be used for site-specific introduction of donor DNA into an RS site in the plant genome without the complication of recombinase expression in the resulting plant.

Both the agarose gel and luciferase expression studies indicate that conditions which favor DNA delivery are not optimal for mRNA and vice versa. By choosing different precipitation conditions, one can favor either of the two to achieve optimal levels of rearranged DNA in the target plant cell. Electrophoretic analysis of the nucleic acid on the gold particles after precipitation proved an elegant means of qualitatively and quantitatively assessing the efficiency of different precipitation conditions. This approach can be used to explore further refinements of nucleic acid delivery conditions via particle bombardment. The final diagnostic, however, must be biological activity since gel electrophoresis can only detect gross damage.

The mRNA molecules introduced exogenously in this study were designed with three features known to play a role in efficient transcript expression. A cap was added at the 5' terminus to act as the recognition site for binding the eukaryotic initiation factor, an early and essential step in translation. A poly (A) tail of 50 adenylate residues was synthesized onto the 3' terminus during in vitro transcription since non-adenylated mRNA's translate ca. 100- to 200-fold less efficiently than their adenylated counterparts in electroporated tobacco, carrot, maize and rice protoplasts (Gallie et al., 1989 Plant cell). Efficiency of a polyadenylated mRNA has also been shown to be enhanced by an order of magnitude in the presence of the 5' cap (Gallie, 1991). The untranslated leader sequence of CaMV35S was included and has been shown to enhance expression in both tobacco and in maize (Gallie et al., 1989 Plant cell; Dowson Day et al., 1993; Carozzi N. personal communication).

Direct delivery of mRNA to plant cells provides advantages to the study of cell functions. mRNA stability and translational efficiency can be examined in vivo independent of transcriptional factors, processing and transport to the cytoplasm. Electroporation (Higgs & Colbert, 1993) and polyethylene glycol (Gallie, 1993 Plant cell reports) have proven to be useful and efficient methods of introducing mRNA to plant protoplasts. However, these methods of delivery are limited to protoplasts, whereas biolistic delivery is widely applicable to many kinds of plant cells and organs. Proteins that might be disadvantageous or too deleterious when stably expressed in a transgenic plant can be expressed transiently from mRNA delivered by biolistics. Recombinase expression in the R/RS plant, for example, could lead to mosaic patterns of excision, just as genetic crosses performed between recombinase gene-containing plants and target site-containing plants often led to chimeric recombination activity and mosaic expression in F1 plants (Russell et al., 1992, Onouchi et al., 1995).

For production of successively improved transgenic constructs in a crop plant, the R/RS system can be used to substitute the new gene(s) in the exact position of the old. Thus a first transgenic cassette and its selectable marker (flanked by RS sites) can be replaced by a second one with a different selectable marker. In turn the second can eventually be replaced by a third, using the first selectable marker once more. This approach would reduce the number of selectable markers needed and would avoid position effect variation on the transgenic cassette.

The use of site-specific recombination systems in plants offers the potential for greater control of transgene insertion and expression. Recombinase systems have enabled insertion at a predetermined location in a genome and may circumvent so-called "position effects" (Fukushige & Sauer, 1992; Lakso et al., 1992; O'Gorman et al., 1991). Recombinase mediated deletion and inversion events of transgenes have allowed control of gene expression and removal of selectable marker genes (for review, see Odell & Russell, 1994). Introduction of recombinase activity in the form of mRNA can expand this use by forcing the occurrence of recombination events early in the transformation process, reducing the risk of mosaicism. In addition, mRNA delivery should provide a greater degree of flexibility in designing site-specific integration schemes that avoid introduction of recombinase genetic information into the genome.

Example 4

Co-Bombardment of mRNA Encoding Intergration-Promoting Proteins VirD1 and VirD2 with DNA into Tobacco and Maize Cells As indicated in the Detailed Description of the Invention, integration-promoting proteins delivered to the eukaryotic cell targeted for transformation via a translatable RNA are expected to be produced for a finite period of time until the translatable RNA is degraded. The protein produced from this RNA is expected to remain in the plant cell for a finite period of time before it too is degraded through normal cellular processes. Thus delivery of integration-promoting proteins in the form of translatable RNA represents a way of delivering such proteins transiently. Transient delivery of these proteins may be preferred in those situations where the continued presence of such proteins may have undesirable effects. The following example describes such an approach for delivering VirD1 and VirD2 proteins to plant cells together with a DNA fragment bounded by T-DNA borders. The results reported indicate that these Vir proteins were produced and conferred their associated integration-promoting activity upon the DNA fragment.

Plant Materials Used

Maize Cells

Suspension cultures of maize (*Zea mays* L. ) initiated from cryopreserved embryogenic type II callus selected from immature embryos of an elite line (2717) related to B73 were grown N6 liquid medium (Chu et al., 1975) supplemented with 30 g/l sucrose and 2 mg/l 2,4-dichlorophenoxy acetic acid (2,4-D) (2N63S). Cultures were incubated at 25° C. in the dark on an orbital shaker at 150 rpm. Suspension cultures were subcultured every 7 days by transferring 1 ml packed cell volume into 50 ml fresh 2N63S liquid medium. Maize cell suspensions used for bombardment experiments were taken from 3 day-old rapidly growing cultures. Before bombarding, approximately 0.5 ml of packed volume cells was vacuum filtered onto 7-cm filters (Whatman, N°4).

Tobacco Cells

The *Nicotiana tabacum* cell line NT-1 was grown in Murashige and Skoog medium supplemented with 2 mg/l of 2,4-D and sucrose (30g/l). Cells were subcultured once per week by adding 5 ml of inoculum to 100 ml of fresh medium in 500-ml flasks. The flasks were incubated at 27° C. on a rotary shaker at 125 rpm. Aliquots of 0.5 ml from cells four days after subculture were spread onto sterile filter (Whatman No. 4). Filters were then transferred onto MS medium.

Plasmid Construction

1—Construction of a Vector Containing the T7 Promoter and the Poly A Tail:

A polylinker (SphI-EcoRI-NheI-ClaI-BglII-Asp718-HindIII-XhoI-Hind*III, inactivating the HindIII site) was inserted into the SphI-HindIII sites of pT7RecA50 (see Example 3). The oligo Asp718- A(50)-DraI-HindIII was then inserted into the corresponding sites giving rise to pT7-A50.

2—Construction of pT7D1A50:

The EcoRI-BglII fragment containing the virD1 coding region previously cloned into EcoRI-BamHI of pSG5 (from the EcoRI-BamHI fragment of p35SAdh1D1) was inserted into pT7-A50 digested with EcoRI and BglII.

3—Construction of pT7D2A50:

Two fragments, EcoRI-BamH1 (5'-terminus) and BamI-ClaI (3'-terminus), of the virD2 coding region were cloned into EcoRI-ClaI of pT7-A50. The 3'-terminus was first cloned as an BamHI-HaeIII fragment into BamHI-EcoRV of the pBluescript plasmid pSK in order to convert it to a BamHI-ClaI fragment.

mRNA Synthesis

The T7D1A50 and T7D2A50 plasmids were linearized with XhoI, which cuts immediately downstream of the poly(A) stretch. Linearized DNA was phenol/chloroform extracted and then ethanol precipitated. In vitro transcription of linearized DNA was carried out using the T7 polymerase from the T7 Cap-Scribe kit containing [m$^7$G(5')ppp(5')] (Boehringer). The integrity and concentration of mRNA encoding VirD1 and VirD2 were determined by agarose gel electrophoresis.

Sterilization of Biolistic Supplies

Gold particles (0.3 μm—Heraeus) were sterilized by placing 60 mg particles in 100% ethanol and 0.1% DEPC. Particles were rinsed 3 times with RNase-free water and then resuspended in 1 ml RNAse-free 50% glycerol solution. Aliquots of 50 μl prepared particles were used for 6 shots. Macrocarriers were submerged in 100% ethanol and 0.1% DEPC, then rinsed 3 times in 100% ethanol and air dried. Stopping screens were autoclaved.

Nucleic Acid Precipitation

DNA (1 μg) and mRNA (about 8 μg: 4 μg virD1 and 4 μg virD2 or 8 μg non-specific mRNA for the control) were precipitated onto a 50 μl suspension of gold particles (60 mg/ml; 0.3 um) by adding successively 0.5 μl Tris buffer (1M), 50 μl CaCl$_2$ (2.5M) and 2.5 μl 0.1 M spermidine. After all agents were added, vortexing was continued for 3 minutes, after which the particles were sedimented by brief microcentrifugation (1 min). The supernatant was removed and the particles were washed once with cold 100% ethanol, and resuspended in 60 μl 100% ethanol. This mixture was vortexed, and 10 μl aliquots were pipetted onto a macrocarrier disk and allowed to air dry in a laminar flow hood.

Microprojectile Delivery into Plant Cells

Microprojectiles were delivered to plant cells by a particle accelerator (PDS-He1000; DuPont) using 1100 psi rupture disks with the sample positioned 5.5 cm from the launch assembly. A 100 μm mesh stainless steel screen was placed halfway between the stopping plate and the tissue. Target plates were bombarded 2 times.

Luciferase Assays

Luciferase was assayed in tissue extracts with the luciferase assay system of Promega according to the recommendation of the supplier . Luciferase activity is expressed as light units detected by an Analytical Luminescence model 2001 Luminometer for 10s at 25° C. For calculation of specific activity, protein concentration was determined using the Bio-Rad protein assay kit.

Results

Luciferase assays were performed 24-h after bombardment. mRNA of virD1 and virD2 were co-bombarded with p35SRBLuc that contains a right border sequence inserted between the 35S promoter and the luciferase coding sequence. In the control experiment, p35SRBLuc was bombarded with unspecific mRNA. Results of an initial experiment are displayed in Table 7 below. Results of a subsequent experiment are described in Example 8 and displayed in Table 14.

TABLE 7

Bombardment of plant cells with virD1 and virD2 mRNA. Numbers between parentheses indicate the molar ratio of plasmids to mRNA. pGUS was also co-bombarded in each experiment. Following incubation for 24 hrs, tissues were homogenized and enzyme activities determined. Activities are expressed as a ratio of luciferase (Luc) to β-glucuronidase (Glu). Independent bombardments were analyzed and data are presented as mean values of 3 repetitions plus or minus standard deviation.

| | Tobacco | | Maize | |
|---|---|---|---|---|
| | Mean | ±SD | Mean | ±SD |
| pRB(+)Luc | 9.3 | ±0.4 | 8.6 | ±1.0 |
| pRB(+)Luc + D1 mRNA | 7.6 | ±0.5 | 8.6 | ±0.2 |
| pRB(+)Luc + D2 mRNA | 8.4 | ±0.1 | 8.3 | ±0.1 |
| PRB(+)Luc + D1 mRNA + D2 mRNA (1:1:1) | 5.6 | ±0.1 | 6.5 | ±0.9 |
| pRB(+)Luc + D1 mRNA + D2 mRNA (1:2:2) | 4.3 | ±0.2 | 4.7 | ±0.4 |
| pCIB1711 | 8.8 | ±0.8 | 10.5 | ±1.4 |
| PCIB1711 + D1 mRNA + D2 mRNA(1:1:1) | 9.2 | ±0.5 | 8.9 | ±0.3 |
| pCIB1711 + D1 mRNA + D2 mRNA(1:2:2) | 8.6 | ±0.4 | 11.8 | ±1.9 |

Conclusion

Following co-delivery of virD1 mRNA and virD2 mRNA with pRB(+)Luc DNA, a 50% decrease in luciferase activity was observed in this experiment (Table 7). The two vir genes delivered as a mRNA to the plant cell appeared to have a synergistic effect. These observations strongly indicate that the decrease of luciferase activity seen was the result of a strand-specific nick at the right border sequence by the virD1 and VirD2 proteins.

Example 5

T-Strand Integration in the Maize Genome Generated in Planta

Abstract

A novel plant transformation technique designated "agrolistic" herein was developed which allows the integration of the gene of interest only, with no vector sequence, as in T-DNA inserts, and to control the copy number. The approach is to use plant expression cassettes for virulence genes codelivered by the biolistic device with a vector containing T-DNA border sequences flanking a selectable marker. In the present study, the wheat dwarf virus (WDV) was chosen as a replicating vector to introduce plant-expressible virulence genes (virD1, virD2 and virE2) and a selectable marker flanked by the left and right border sequences and into maize cells. It was found that virD1 and virD2 gene products can indeed cleave T-DNA border sequences in planta and produce T-DNA-type insertion events ("agrolistic" events) after biolistic delivery.

Introduction

Agrobacterium is widely used as a tool for genetic manipulation or engineering of plant cells by transformation. A particular region of its pathogenic plasmid, the T-DNA, is transferred and stably integrated into the plant genome. The T-DNA is delimited by direct-repeat sequences of 25-bp called border sequences (for review, see Zupan & Zambryski, 1995). Any DNA sequence located between T-borders can be transferred efficiently from Agrobacterium to the plant cells. However, T-DNA transfer and integration is limited by the host-range of the bacterium, allowing efficient transformation of most dicotyledonous, but of only few monocotyledonous plants (for review, Chilton, 1994).

To fill the gap arising from the limited host range of Agrobacterium, it is desirable to find efficient methods for genetic transformation of monocotyledons. One possible method consists of generating the T-complex in planta by providing to the plant cells all the tools necessary for the reconstruction of the complex. Those tools are: 1) the gene of interest flanked by border sequence, and 2) the virulence genes under the control of plant expression cassette. The virD1 and virD2 gene products are essential to the key-step of T-DNA processing (for review, see Zupan & Zambryski, 1995). VirD2 is a strand-specific endonuclease, which when assisted by VirD1 specifically recognizes border sequences. Upon cutting, VirD2 remains covalently attached to the 5'end of the single strand DNA or T-strand. The T-strand is protected by a single strand binding protein virE2. The resulting nucleoprotein complex is exported to the plant cell. VirD2 contains nuclear localization signals that pilots the T-strand into the nucleus of the plant cell. VirD2 may participate in the ligation of the 5' end of the T-strand to the plant genome (Tinland et al., 1995).

In the present study, the wheat dwarf virus (WDV; Ugaki et al., 1987) was chosen as a replicating vector in plants to study the formation of T-strands in planta and its integration into the plant genome. The purpose of using such a vector is that geminiviruses propagate in the plant cell nucleus in high copy numbers and allow high level of expression.

Materials and Methods

Plasmids (See FIG. 5 for schematic representation)

pCIB1711 is a pUC derivative that contains the firefly luciferase gene driven by the cauliflower mosaic virus 35S (CaMV35S) promoter. It is described in Example 3.

pwiBarRBLuc was designed for stable transformation of maize suspension cells and contains a left border sequence, the Bar gene (Thompson et al., 1987) driven by the CaMV35S promoter and the luciferase gene with the right border sequence inserted between the promoter and the luciferase coding region. The bar gene was excised from pCIB3064 (Koziel and al., 1993) as an HindIII-EcoRI fragment. The left border was excised from pBin19 as a BglII-EcoRI fragment (Bevan, 1984).

virD1 and virD2 genes from pTiA6 were first subcloned into expression vectors pMF6 (Callis et al., 1987), consisting of the CaMV35S promoter (0.5 kb), the Adh1 first intron (0.5 kb), and the nopaline synthase (nos) polyadenylation region (0.25 kb). The 0.6 kb EcoRI-PstI fragment from pAD1187 (Vogel and Das, 1992) and the 1.8 kb fragment form pAD 1190 were cloned into pMF6 yielding p35SAdhD1 and p35SAdhD2 respectively. The XbaI-NotI fragment from p35SAdhD1 comprising the virD1 gene under the control of the 35S promoter was subcloned into the NheI-Not sites of a modified pwi-11. A polylinker (NheI-NotI-SpeI-KnpI-BglII) was introduced into the unique BamHI-SalI sites of pwi-11 (Ugaki et al., 1987). The NotI fragment from p35SAdhD2 comprising the virD2 coding sequence under the control of the 35S promoter was subcloned into the unique NotI site of pwi-11.

The virE2 coding region was excised from pw 108 that contains a 3 kb XhoI fragment of Agrobacterium Ti-plasmid pTiA6 (accession number X04784)(Winans al., 1987). The 687-bp SacI-SmaI fragment of pw 108 was first cloned into the corresponding sites of pBluescript KS—(Stratagene, Inc.) to give rise to pKS3'E2. The 924 bp HaeIII-SacI from pw 108 was combined with the SacI-PstI fragment from pKS3'E2 and an annealed pair of DNA oligonucleotides flanked by EcoRI-cohesive and blunt ends (AATTCATGGATCTTTCTGGCAATGAGAAATCCAGG) (SEQ ID NO:17) and cloned into the EcoRI-PstI sites of pBluescript KS—to give rise to pKSE2. An XhoI-PstI fragment that covered the entire virE2 coding region was then subcloned into XhoI-PstI of pMF6 to give rise to p35SAdhE2. The NotI-XbaI fragment containing the 35S promoter, the Adh1 intron, the virE2 coding region and the Nos terminator was cloned into the NotI-NheI sites of pwi-11.

pGUS is a pUC derivative containing the β-glucuronidase (GUS) coding sequence under the control of the CaMV35S promoter and the castor bean catalase gene intron (Ohta et al., 1990)

Maize Suspension Cells

The suspension culture of Zea Mays cv Black Mexican Sweet (BMS) was maintained in N6 media (Chu et al., 1975) supplemented with 30 g/l sucrose and 2 mg/l 2,4-dichlorophenoxy acetic acid (2,4-D) (2N63S). Maize cell suspensions used for bombardment experiments were taken from 3 day-old rapidly growing cultures. Before bombarding, approximately 0.5 ml of packed volume cells was vacuum filtered onto 7-cm filters (Whatman, N°4). Plated cells were kept 4 hours at 25° C. prior to bombardment on phytoagar-solidified 2N6 medium containing 120 g/l of sucrose. For stable transformation, filters were transferred to 2N63S solidified-medium 24 hours after bombardment. Subsequent transfers of filters on fresh medium with increasing concentration of Basta were made at 8 days intervals until the majority of cells in the culture ceased to grow. This generally occurred after 4 to 6 weeks of selection on plates containing 8 to 10 mg/l of Basta. Independent calli developed on the filter were then transferred to phytoagar-solidified medium supplemented with Basta (10 mg/l). After two subcultures on the same medium, suspension cultures were initiated by inoculating about 100 mg of maize cells into 25 ml liquid medium supplemented with Basta (10 mg/l) for DNA isolation.

Bombardment of Plant Cells

Tissues were bombarded with gold microprojectiles onto which was precipitated a mixture of plasmids. pGUS plasmid DNA was used as internal control in transient experiments. For cotransformation experiments, the gold particles carried either an equal mass of all plasmid DNAs (0.5 μg of each plasmid DNA per target plate). For stable transformation experiments, co-transformation mixtures contained a 1:1 or 2:1 molar ratio of plasmids carrying the virulence genes to bar selection plasmid. Each aliquot of plasmid mixture bombarded per target plate consisted of 0.4 μg of the selection marker and 0.4 μg or 0.8 μg each of pwi35SAdhD1 and pwiAdh35SD2 and/or pwiAdh35SE2 plasmid DNAs. Appropriate quantities of each DNA were mixed in a total volume of 10 μl and precipitated with 50 μl of 2.5 M CaCl$_2$ and 20 μl of 0.1 M spermidine-free base to effect precipitation onto 50 μl of 0.3 μm gold microcarriers (60 mg/ml). Microprojectile bombardment was performed with the PDS-1000 He biolistic device (DuPont) using 1100 psi rupture discs with the sample positioned 8 cm below the stopping screen shelf.

Transient Expression Assays

Luciferase was assayed in tissue extracts according to the recommendation of the supplier (Luciferase assay system, Promega). β-glucuronidase activity was determined by a chemoluminescent assay with the GUS-Light kit (Tropix). Luciferase and β-glucuronidase activities are expressed as light units detected by an Analytical Luminescence model 2001 Luminometer integrated over 10 seconds at 25° C.

DNA Extraction and Southern Blot Hybridization

Cell cultures were harvested by filtration 10 days after inoculation and frozen in liquid nitrogen. DNA was isolated as described (Hall et al., 1991).

Approximately 10 μg of genomic DNA was used for digestion with EcoRI. Following separation on a 0.7% agarose gel, the DNA was transferred to Amersham Hybond plus membrane and hybridization was performed according to the conditions described by the manufacturer (Amersham). DNA probes were labeled with [a-$^{32}$P]dCTP using the oligo labeling kit of Pharmacia. The Bar probe corresponded to a 0.5-kb BglII fragment of the Bar gene. The luc probe corresponded to a 0.7 kb XbaI-EcoRI fragment of the luciferase gene. For removal of probes, membranes were stripped with a solution of 0.1% SDS at 100° C. for 5 min.

Cloning of T-DNA/Plant DNA Junctions

DNA (30 μg) from transgenic maize calli was digested with EcoRI and subjected to preparative electrophoresis on a 0.8% agarose gel. Slices of agarose corresponding to the size of fragments to be cloned were cut out of the gel and DNA was extracted from agarose with gene clean Kit. Fragments were then cloned into the dephosphorylated EcoRI site of pUC 18. Ligation mixes were used to transform E. coli HB101 cells by electroporation. Colonies containing the plasmid with the correct insert were identified by colony filter hybridization, using a 0.5 kb Bar fragment as probe. DNA from positive clones were then digested with BamHI-EcoRI. BamHI has a site located at a distance of 3-bp from the right border sequence. The fragment was recloned into the corresponding sites of pUC18. Sequence of the junction of donor plasmid DNA with plant DNA was analyzed using the universal primer.

Results

Transient Expression Assays to Test for Cleavage of the Border Sequence by virD1 and virD2 Gene Products in Planta In order to investigate whether virD1 and virD2 gene products can nick a T-DNA border sequence when expressed in plant cells, test plasmids pwiRBLuc and pRBLuc were assayed. They contained a substrate T-DNA border sequence between the promoter and the coding region of the luciferase gene. pRBLuc is a pUC derivative whereas pwi is a wheat dwarf virus (WDV)-derived vector that can replicate in maize cells and consists of the two complementary sense ORFs, C1 and C2 required for replication of the virus and the p15A origin of replication from E. coli. This vector does not contain ORF V1 and ORF V2 involved in the viral spread and symptom development (Ugaki et al., 1991). A site-specific nick introduced by virD1 and virD2 gene products would lead to a break in the DNA strand that is the template for the luciferase mRNA, and thus should decrease the production of luciferase transcript and enzyme. After co-bombardment of plant cells with pRBLuc or pwiRBLuc and plasmids carrying the vir D genes under the control of the CaMV35S promoter, any nicking at the border sequence should be measurable quantitatively by assaying luciferase activity.

A high level of expression of the luciferase gene was attained in maize cells bombarded with pRBLuc DNA or with pwiRBLuc DNA. Co-delivery of pwiRBLuc DNA of pwiD1 DNA and pwiD2 DNA with pRBLuc DNA or with pwiRBLuc DNA resulted in a 10-fold decrease of luciferase to GUS activity (Table 8). Codelivery of pwiD2 DNA with pwiRBLuc DNA also resulted in a 10-fold decrease of luciferase to GUS activity. This result can be explained by the fact that WDV has a genome composed of one circular single-stranded DNA. They multiply in the nucleus of infected cells via a double-stranded intermediate that is subsequently used as template for rolling circle replication of the viral-strand DNA (Saunders et al., 1991; Stenger et al., 1991). VirD2 has been shown to cleave in vitro single-stranded oligonucleotide (Pansegrau et al., 1993; Jasper et al., 1994). Thus VirD1 is not required for cleavage of ssDNA form of the geminivirus.

Analysis of Stable Transformants

Stable transformation of maize suspension cells was undertaken to assess the activity of VirD1 and VirD2 gene products on the pattern of DNA integration after co-delivery of these genes with their substrate DNA by the biolistic device. For these experiments we used pwiBarRBLuc and pBarRBLuc, which contain a left T-DNA border, the Bar as selectable marker, and the 35SRBLuc gene with the right T-DNA border inserted between promoter and luciferase coding region. The screen for virD-mediated integration events was absence of luciferase activity in the transformed clone, arising from exclusion of the Luc coding region by T-DNA excision from pBarRBLuc or from pwiBarLuc. Such events that would result after the activity of the vir gene products on border sequences, generating a T-strand, were designated "agrolistic events". In contrast, "biolistic events" were inserts in the maize genome representing the process normally occurring after gene delivery into plant cells by the biolistic device.

Maize suspension cells were bombarded with microprojectiles coated with pBarRBLuc or pwiBarRBLuc plasmid DNAs together with pwiD1 and pwiD2 DNA in a ratio 1:1:1 or 1:2:2. As controls, pwiBarRBLuc and pBarRBLuc plasmids were also bombarded alone. Stable transformants were selected by growth on Basta-containing medium. An average of 8 to 10 Basta-resistant clones appeared per filter 3–4 weeks after bombardment, but only a subset were further analyzed from each plate. When p35AdhE2 plasmid DNA was co-delivered with the other virulence genes, a slightly higher number of calli were recovered per filter (12–15). A rough estimate of the frequency of agrolistic events could be made by the ratio of the total number of Basta-resistant calli analyzed that do not express luciferase to total Basta calli. By this criterion, the frequency of agrolistic events was about 20% when pBarRBLuc was co-delivered with pwi35SAdhD1 and pwi35SAdhD2 plasmid DNAs. The frequency increased to about 40% when the target plasmid used was pwiBarRBLuc. This frequency increased to about 50% when pwi35SAdhE2 was also co-delivered with the plasmids described above.

Southern Analysis

At the molecular level, the inserts representing an agrolistic event should hybridize with the Bar probe and not with the luc probe. Moreover, in an agrolistic event, the sequence of the junction between introduced DNA and plant DNA should correspond precisely to the right border end of a T-strand. Both types of events may occur in the same plant cell, but such clones would be scored genetically as biolistic events based on the presence of luciferase activity. Both biolistic and putative agrolistic events were investigated by southern hybridization to measure the frequency of each type of insertion.

Southern blot hybridization was performed on DNA from basta-resistant callus lines obtained after bombardment with (i) pwiBarRBLuc DNA, (ii) pwiBarRBLuc, pwi1 and pwiD2 DNAs, (iii) pwiBarRBLuc, pwiD1, pwiD2 and pwiE2 DNAs, (iv) pBarRBLuc DNA and (v) pBarRBLuc, pwiD1, pwiD2 DNAs.

Analysis of blots revealed 3 groups of transgenic callus lines as summarized in Table 9: (i) callus lines hybridizing with both the bar and the neo probe; (ii) callus lines in which some inserts hybridized with only the bar probe and some inserts hybridized with both probes; (iii) callus lines with inserts hybridizing only with the bar probe. The first group of calli probably did not contain agrolistic events. The second group of calli probably contained two types of events: agrolistic events and biolistic events. The third group of calli exhibited only putative agrolistic events. For instance, among 10 transgenic maize lines analyzed from the pwiBarRBLuc, pwiD1 and pwiD2 transformation experiment, 3 contained biolistic events, 6 contained putative agrolistic events and 1 had both. The hybridization patterns of the separate lines were unique showing that the callus lines were independent transformation events.

Molecular Analysis of Putative Agrolistic Events:

The nature of putative agrolistic events was verified by determining the sequence of the junction between integrated DNA and plant DNA. The nucleotide sequence revealed that each of these fragments contained a right border/plant DNA junction. The right end point of the inserted fragment was identical to the nicking site of the right border sequence of the T-DNA, as expected for an agrolistic event.

TABLE 8

Activity of virD1 and virD2 in maize cells.

| Plasmids | Mean | ±SD |
|---|---|---|
| pwi35SRBLuc | 15.0 | ±1.2 |
| pwi35SRBLuc + pwi35SAdhD1 (1:1) | 8.1 | ±1.1 |
| pwi35SRBLuc + pwi35SAdhD2 (1:1) | 0.7 | ±0.3 |
| pwi35SRBLuc + pwi35SAdhD1 + pwi35SAdhD2 (1:1:1) | 0.2 | ±0.1 |
| p35SRBLuc | 17.6 | ±1.2 |
| p35SRBLuc + pwi35SAdhD1 + pwi35SAdhD2 (1:1:1) | 0.8 | ±0.1 |
| p35SRBLuc + p35SAdhD1 + p35SAdhD2 (1:1:1) | 1.0 | ±0.2 |
| no DNA | 0.2 | |

DNA was delivered to maize cells by the biolistic device. Numbers between brackets indicate the ratio of plasmids. Following the incubation for 24 hrs, tissues were homogenized and enzyme activities determined. A plasmid expressing the b-glucuronidase (GUS), pGUS, was included in each bombardment as a control for the efficiency of DNA transfer and the activity of the reporter gene is expressed as a ratio of the luciferase to GUS activity. Independent bombardments were analyzed and data are presented as mean values of 3 repetitions plus or minus standard deviation.

TABLE 9

Analysis of basta-resistant calli recovered from bombardment of BMS cells with the target plasmid alone and/or with vir genes.

| Plasmids | callus | luciferase act. | Southern | type of event |
|---|---|---|---|---|
| pwiBarRBLuc (0.2 μg) | 16 | 15 Luc (+) 1 Luc (−) | 5 | 5 B |
| pwiBarRBLuc + pwiD1 + pwiD2 (0.4 μg + 0.4 μg + 0.4 μg) | 19 | 10 Luc (−) 9 Luc (+) | 10 9 | 3 B, 6 A, 1 A + B 8 B, 1 B + A |
| pwiBarRBLuc + pwiD1 + pwiD2 (0.4 μg + 0.8 μg + 0.8 μg) | 11 | 8 Luc (−) 3 Luc (+) | 4 1 | 1 B, 2 A, 1 B + A 1 B |
| pwiBarRBLuc + pwiD1 + pwiD2 + pwiE2 (0.4 μg + 0.4 μg + 0.4 μg + 0.4 μg) | 21 | 10 Luc (−) 11 Luc (+) | 4 5 | 1 B, 2 A 5 B |
| pBarRBLuc (0.4 μg) | 10 | 9 Luc (+) | 2 | 2 B |
| pBarRBLuc + pwiD1 + pwiD2 (0.4 μg + 0.4 μg + 0.4 μg) | 38 | 7 Luc (−) 31 Luc (+) | 4 5 | 4 B 4 B, 1 B + A |

Numbers between brackets indicate the concentration of DNA used for transformation experiments.
B = biolistic event; A = putative agrolistic event; Southern = number of callus analyzed by southern; Callus = number of callus analyzed for the luciferase activity Example 6

Expression of VirD1 and VirD2 from a Single Promoter in Maize and Tobacco Cells

To achieve expression of bacterial genes in plant cells, the individual coding regions of the bacterial genes must be fused to separate plant promoters because prokaryotic promoters will not allow transcription in plant cells. While it is feasible to fuse each gene to a separate promoter, it could present several difficulties: for instance, silencing if the same promoter is used for the different genes. The strategy demonstrated in this example is to link in tandem two genes to only one plant promoter. This polygenic message contains the two coding sequences of virD1 and virD2 that belong to the virD operon of Agrobacterium.

These two polypeptides encoded by the 5' half of the virD operon play a key role in the initiation of DNA processing for T-DNA transfer from Agrobacterium to plant cells. VirD2 is a strand-specific endonuclease which assisted by VirD1 cleave the T-DNA border sequences between the third and fourth bases. VirD2 remains covalently attached to the 5'end of the T-DNA and is believed to pilot the T-DNA into the plant cells and to participate in the ligation of the 5'end of the T-DNA into the plant genome. These two proteins have been shown to be functional in plant cells when hooked to a plant promoter.

In this example, an expression unit composed of virD1 and virD2 genes driven by a single plant promoter was engineered which demonstrated functional expression in planta. The individual genes were linked either as transcriptional fusion or as translational fusions and were shown in the latter case to retain their enzymatic activities in plant cells.

Materials and Methods

Plasmid Construction

Construction of D1-D2 or D2-D1 fusions

Two types of fusion were constructed

1) Transcriptional Fusion

The sequence of virD1 and virD2 coding region with the small interspace (33 nt) present between virD1 and virD2 coding region was used. The 1.1 kb NotI-PstI fragment of p35SD1 and the 1.5 kb PstI-XbaI fragment of p35D2 were cloned into the NotI-SpeI sites of pSK+ to give rise to p35StpD1D2.

2) Translational Fusions

The virulence genes virD1 and virD2 were also fused via an intervening sequence projected to allow free movement of both proteins and which is susceptible to post-translational cleavage. For p35SD1D2, the virD1 coding region is at the 5' end of the fusion whereas p35SD2D1 contained the virD2 region directly behind the promoter. All modifications were confirmed by DNA sequencing.

Construction of p35SD1D2: To create a fusion virD1–virD2 that encoded virD1 and virD2, the stop codon of virD1 and the initial codon of virD2 were removed. This was done by cloning into the EcoRI-HindIII of pUC21 an annealed pair of DNA oligonucleotides, flanked by BanI-cohesive and pvuI-cohesive ends to the 0.48-kb EcoRI-BanI of p35SD1 and the 0.25 kb PvuI-HindIII fragment of p35SD2. The annealed pair was composed of the following oligonucleotides:

(SEQ ID NO:18)
5'GTGCCTTGCCTTCTACTCCCCCAACTCCCTCTCCTAGCACGCCTCCG ACACCTAGCCCCGAT-3'. and (SEQ ID NO:19)
5'-CGGGGCTAGGTGTCGGAGGCGTGCTAGGAGAGGGAGTTGGGGGAGTA GAAGGCAAG-3'.

The EcoRI-PstI fragment of this construct encompassing the virD1 coding region, the linker and the 5'end of the virD2 coding region was then inserted into the EcoRI-PstI sites of p35SD2 to give rise to p35SD1D2.

Construction of p35SD2D1: Similarly, plasmid pD2D1 contains the virD2 coding region at the 5' end of pD2D1 linked in frame to the virD1 coding region through the same intervening sequence. The N-terminal coding sequence of virD1 was first reconstructed from overlapping oligonucleotides to provide an EcoRI site at the 5' end and to delete the first codon of virD1

```
                                            (SEQ ID NO:20)
(5'-AATTCTCAAAACACACCAGAGTCACGTCGAGTGAGACTGCCATCA
ACCAGCAT-3').
```

These annealed oligonucleotides were cloned into pBluescript KS+ (Stratagene, Inc) to yield pKS5'D1. The 1.3-kb SacII-BfaI fragment from p35SD2 and the SacII-EcoRI-cut pKS5'D1 plasmid DNA were then joined with a linker containing at the 5' end an alteration of the BfaI site such that it lacks the native stop codon of virD2

```
                                            (SEQ ID NO:21)
(5'-TATCCTTCTACTCCCCCAACTCCCTCTCCTAGCACGCCTCCGACAC
CTAGC-3' and (SEQ ID NO:22)
5'-AATTGGCTAGGTGTCGGAGGCGTGCTAGGAGAGGGAGTTGGGGGA
GTAGAAGGA3').
```

The EcoRI-ClaI fragment encompassing the virD2 coding region, the linker and the 5'end of the virD1 coding region was then cloned into the EcoRI-ClaI sites of p35SD1 to give rise to p35SD2D1.
Construction of the Test Plasmids
The construction of pwBarRBLuc, pRBLuc was described in Example 5.
Plant Material
Preparation of maize (B73-derivative) and tobacco (NT-1) suspension cells for bombardment by the biolistic device was described in previous examples.
Bombardment of Plant Cells
Tissues were bombarded with gold microprojectiles onto which was precipitated a mixture of plasmids. For cotransformation experiments, the gold particles carried 0.5 µg or 1 µg of the test plasmid with a total of 2 µg or 4 µg of the helper plasmids for tobacco and maize cells respectively. Appropriate quantity of DNA of pUC18 plasmid was mixed to preserve an equal mass of plasmid DNAs in the mixture (see table 10 and table 11). DNAs were precipitated with 2.5 M $CaCl_2$ and 0.1 M spermidine-free base onto 50 µl of 0.3 µm gold microcarriers (60 mg/ml). Microprojectile bombardment was performed with the PDS-1000 He biolistic device (DuPont) using 1550 psi rupture discs with the sample positioned 8 cm below the stopping screen shelf.
Transient Expression Assays
Luciferase was assayed in tissue extracts according to the recommendation of the supplier (Luciferase assay system, Promega). Luciferase activity is expressed as light units detected by an Analytical Luminescence model 2001 Luminometer integrated over 10 seconds at 25° C. For calculation of specific activity, protein concentration was determined using the Bio-Rad protein assay kit.
Results and Discussion
Fusion Design Strategy
The virD1 and virD2 genes were derived from the octopine pTiA6 plasmid of Agrobacterium tumefaciens. The transcriptional fusion carried by p35StpD1D2 contains the coding region of virD1 and virD2 with the native intervening sequence present in the virD operon.
The translational fusions carried by p35SD1D2 and p35SD2D1 contains the virD1 and virD2 coding regions fused via an intervening sequence projected to allow free movement of both proteins and which is susceptible to post-translational cleavage.
Functional Expression of the Polygene in Planta
To assay the functional expression of the transcriptional and the translational fusions, p35StpD1D2, p35SD1D2 and p35SD2D1 were co-delivered to plant cells with a test plasmid by the biolistic device. The test plasmid contained a right border sequence inserted between the promoter and the coding region of the luciferase gene in such a way that a strand-specific cleavage inside this sequence would lead to the decrease of the luciferase expression. Two type of test-plasmids were assayed in maize cells: a pUC-derivative plasmid (pRBLuc) and a wheat dwarf geminivirus-derived plasmid (pwBarRBLuc).

Maize and tobacco cells were first transiently transformed with the test plasmid codelivered with virD1 and virD2 genes each driven by a separate promoter, in order to test their ability to affect transcription through the T-DNA border sequence. Following co-delivery of p35SD1 DNA and p35SD2 DNA with pRBLuc or pwBarRBLuc DNA, 0.3% and 1% of the control level of luciferase activity was observed in tobacco and maize tissues (Table 10, Table 11 and Table 12).

The two vir genes together in a transcriptional fusion appeared to be slightly active. Co-delivery by the biolistic device of equal amounts of pRBLuc and p35StpD1D2 DNAs (ratio of 1:1) reduced luciferase activity to ca. 57% of control in tobacco (Table 12) and 60–80% in maize cells (Table 10 and Table 11). At a higher ratio of p35StpD1D2 plasmid to test plasmid (2:1), there was no significant further reduction of the luciferase activity.

Analogous experiments using the p35SD1D2 plasmid that carried the translational fusion showed a reduction of the luciferase activity to ca. 12% of control in tobacco (Table 12) and 22–47% in maize cells (Table 10 and Table 11). At a higher ratio of p35SD1D2 plasmid to test plasmid (2:1), the luciferase activity was further reduced to about 2–5% in all cases.

Reversal of the native orientation of the virulence genes in the translational fusion p35SD2D1 gave results similar to those with p35SD1D2 (Tables 10, 11 and 12).

These observations strongly indicate that the translational fusions were functional in planta.

TABLE 10

Activity of transcriptional and translational fusions in maize cells with a pUC-derivative vector as a test plasmid.

| Plasmids delivered to maize cells | Luciferase activity | % of control |
|---|---|---|
| pRBLuc + pUC18 (1 µg + 4 µg) | 12333 ± 543 | 100 |
| pRBLuc + p35SD1 + p35SD2 (1 µg + 2 µg + 2 µg) | 182 ± 43 | 1.5 |
| pRBLuc + p35SD1D2 + pUC18 (1 µg + 2 µg + 2 µg) | 5744 ± 290 | 47 |
| pRBLuc + p35SD1D2 (1 µg + 4 µg) | 300 ± 12 | 2.4 |
| pRBLuc + p35SD2D1 + pUC18 (1 µg + 2 µg + 2 µg) | 5920 ± 813 | 48 |
| pRBLuc + p35SD2D1 (1 µg + 4 µg) | 329 ± 59 | 2.6 |
| pRBLuc + p35StpD1D2 + pUC18 (1 µg + 2 µg + 2 µg) | 7312 ± 1091 | 60 |
| pRBLuc + p35StpD1D2 (1 µg + 4 µg) | 6436 ± 615 | 52 |

DNA was delivered to maize cells by the biolistic device. Numbers between brackets indicate the ratio of plasmids. Following incubation for 24 hrs, tissues were homogenized and the luciferase activities were determined and expressed as light units/µg proteins. Independent bombardments were analyzed and data are presented as mean values of 3 repetitions plus or minus standard deviation.

TABLE 11

Activity of transcriptional and translational fusions in maize cells with a geminivirus-derivative vector as a test plasmid.

| Plasmids delivered to maize cells | Luciferase activity | % of control |
|---|---|---|
| pwBarRBLuc + pUC18 (1 μg + 4 μg) | 531 ± 38 | 100 |
| pwBarRBLuc + p35SD1 + p35SD2 (1 μg + 2 μg + 2 μg) | 5 ± 3 | 1 |
| pwBarRBLuc + p35SD1D2 + pUC18 (1 μg + 2 μg + 2 μg) | 115 ± 23 | 22 |
| pwBarRBLuc + p35SD1D2 (1 μg + 4 μg) | 32 ± 4 | 6 |
| pwBarRBLuc + p35SD2D1 + pUC18 (1 μg +2 μg + 2 μg) | 60 ± 10 | 11 |
| pwBarRBLuc + p35SD2D1 (1 μg + 4 μg) | 19 ± 3 | 3.6 |
| pwBarRBLuc + p35StpD1D2 + pUC18 (1 μg + 2 μg + 2 μg) | 431 ± 115 | 81 |
| pwBarRBLuc + p35StpD1D2 (1 μg + 4 μg) | 380 ± 53 | 72 |

See footnote for Table 10.

TABLE 12

Activity of transcriptional and translational fusions in tobacco cells.

| Plasmids delivered to tobacco cells | Luciferase activity | % of control |
|---|---|---|
| pRBLuc + pUC18 (0.5 μg + 2 μg) | 21611 ± 760 | 100 |
| pRBLuc + p35SD1 + p35SD2 (0.5 μg + 1 μg + 1 μg) | 60 ± 1 | 0.3 |
| pRBLuc + p35SD1D2 + pUC18 (0.5 μg + 1 μg + 1 μg) | 2494 ± 44 | 12 |
| pRBLuc + p35SD1D2 (0.5 μg + 2 μg) | 1179 ± 183 | 5.4 |
| pRBLuc + p35SD2D1 + pUC18 (0.5 μg + 1 μg + 1 μg) | 1603 ± 422 | 7.4 |
| pRBLuc + p35SD2D1 (0.5 μg + 2 μg) | 1071 ± 113 | 5 |
| pRBLuc + p35StpD1D2 + pUC18 (0.5 μg + 1 μg + 1 μg) | 12240 ± 1417 | 57 |
| pRBLuc + p35StpD1D2 (0.5 μg + 2 μg) | 11627 ± 2491 | 54 |

See footnote for Table 10.

Example 7
Role of VirE2 in Transformation Efficiency

A "healing" vector was tested in maize cells for its ability to increase the frequency of agrolistic events. This vector used contained a polyadenylation signal inside the T-DNA structure at the left of the right border.

In a second part of the experiment, virE2 was co-delivered with virD1 and virD2 genes. This protein has been shown to be required for efficient transfer of T-DNA, but not for T-DNA production (Stachel et al., 1986). VirE2 binds to single-stranded DNA in vitro cooperatively and non-specifically. VirE2 may participate in the protection of the T-strand. The virE2 protein is the most abundant protein produced in *Agrobacterium tumefaciens* after induction of the virulence genes (Stachel et al., 1986). Since virE2 possess nuclear localization signals and those are recognized in plants (for review, see Zupan and Zambryski, 1995), higher rates of transformation are expected when this gene is introduced in planta.

Materials and Methods

Construction of pAVM1: A vector containing polyadenylation signal at the right border (see FIGS. 6–15)

Part A. Construction of pCIB1711-HN pCIB1711 was digested with BamHI and religated to form 1711 deltaB, in which the EcoRI site (now unique) was cut and destroyed by insertion of an oligonucleotide that simultaneously created HindIII and NotI sites. By sequence analysis we identified a clone in which these sites were in the orientation (following the Sacd site) KpnI and then HindIII. To restore the missing parts of the original plasmid, we first inserted the large BamHI fragment carrying the Luc coding region in the correct orientation, forming 1711-HN-B; we then replaced its XbaI insert by the corresponding portion of the original pCIB1711, reintroducing the missing leader sequence.

Part B. Introduction of a synthetic oligonucleotide border sequence between the EcoRI and BanHI sites at the end of the Luc coding region, we subcloned the NotI/ClaI fragment into pBluescript, rendering EcoRI and BamHI sites in the insert unique. After insertion of the border oligonucleotide to form pBS-NC-RB, we returned its modified NotI/ClaI insert fragment to the pCIB1711-HN backbone, forming pCIB1711-HN-RB.

Part C. Insertion of a left T-DNA border into pUbiPAT-deltaI

In order to eliminate an unwanted EcoRI site in the intron of pUCIAC, we digested the plasmid (grown in dam-minus strain SCS110) with ClaI, removing two small fragments including an EcoRI site. We then introduced an oligonucleotide that removed the ClaI site and crated an SphI site, forming plasmid pUbiPATdeltaI. Into the now unique EcoRI site at the end of the chimeric PAT gene we cloned EcoRI fragment 29 of pTiT37, a nopaline-type Ti plasmid which carries the left border of T-DNA at a position 68 basepairs in from one end (Yadav, N. S., Vanderleyden, J., Bennett, D. Barnes, W. M., and Chilton, M.-D. 1982) Short direct repeats flank the T-DNA on a nopaline Ti plasmid. Proc. Natl. Acad. Sci. USA 79, 6322–6326), forming LB-UbiPATdeltaI.

Part D. Assembly of pAVM1

The HindIII insert fragment of pCIB1711-HN-RB was excised and ligated into the HindIII site of LB-UbiPATdeltaI. By mapping we identified a construct in which the left and right borders are flanking the PAT gene and in correct orientation for transfer. The resulting plasmid has the Luc gene promoter and coding region outside T-DNA but its terminator just inside the right border.

Maize Suspension Cells

The suspension culture of *Zea Mays* cv Black Mexican Sweet (BMS) was maintained in N6 media (Chu et al., 1975) supplemented with 30 g/l sucrose and 2 mg/l 2,4-dichlorophenoxy acetic acid (2,4-D) (2N63S). Maize cell suspensions used for bombardment experiments were taken from 3 day-old rapidly growing cultures. Before bombarding, approximately 0.5 ml of packed volume cells was vacuum filtered onto 7-cm filters (Whatman, N°4). Plated cells were kept 4 hours at 25° C. prior to bombardment on phytoagar-solidified 2N6 medium containing 120 g/l of sucrose. For stable transformation, filters were transferred to 2N63S solidified-medium 24 hours after bombardment. Subsequent transfers of filters on fresh medium with increasing concentration of Basta were made at 8 days intervals until the majority of cells in the culture ceased to grow. This generally occurred after 4 to 6 weeks of selection on plates containing 8 to 10 mg/l of Basta. Independent calli developed on the filter were then transferred to phytoagar-solidified medium supplemented with Basta (10 mg/l). After two subcultures on the same medium, suspension cultures were initiated by inoculating about 100 mg of maize cells into 25 ml liquid medium supplemented with Basta (10 mg/l) for DNA isolation.

Bombardment of Plant Cells

Tissues were bombarded with gold microprojectiles onto which was precipitated a mixture of plasmids. Co-transformation mixtures contained a 1:1.3 ratio of plasmids carrying the virulence genes to bar selection plasmid. Each aliquot of plasmid mixture bombarded per target plate consisted of 0.6 μg of the selection marker and 0.8 μg each of p35SAdhD1 and p35SAdhD2 and/or p35SAdhE2 plasmid DNAs. Appropriate quantities of each DNA were mixed in a total volume of 10 μl and precipitated with 50 μl of 2.5 M CaCl$_2$ and 20 μl of 0.1 M spermidine-free base to effect precipitation onto 50 μl of 0.3 μm gold microcarriers (60 mg/ml). Microprojectile bombardment was performed with the PDS-1000 He biolistic device (DuPont) using 1100 psi rupture discs with the sample positioned 8 cm below the stopping screen shelf.

DNA Extraction and Southern Blot Hybridization

Cell cultures were harvested by filtration 10 days after inoculation and frozen in liquid nitrogen. DNA was isolated as described (Hall et al., 1991).

Approximately 10 μg of genomic DNA was used for digestion with EcoRI. Following separation on a 0.7% agarose gel, the DNA was transferred to Amersham Hybond plus membrane and hybridization was performed according to the conditions described by the manufacturer (Amersham). DNA probes were labeled with [a-$^{32}$P]dCTP using the oligo labeling kit of Pharmacia. The PAT probe corresponded to a 0.7-kb Pst fragment of the pat gene. The luc probe corresponded to a 0.7 kb XbaI-EcoRI fragment of the luciferase gene. For removal of probes, membranes were stripped with a solution of 0.1% SDS at 100° C. for 5 min.

Results

Analysis of Stable Transformants

Stable transformation of maize suspension cells was undertaken to assess the effect of the pAVM1 vector on the efficiency of transformation after co-delivery of such a vector with the virulence genes by the biolistic device. The former vector had a 35S-promoter inside the right border in such orientation that it could easily provide a mean to express the antisense of the gene in which the T-strand was inserted. In this new type of vector, the 35S-promoter was replaced by a 35S-terminator inside the right border, oriented so as to "heal" the target gene should it insert at the 3' end.

For this experiment pAVM1 was used, which contains a left T-DNA border, PAT as selectable marker, a 35S-terminator, a right T-DNA border and the luciferase gene outside the T-DNA-like structure. We designate as "agrolistic events" those DNA insertions into the maize genome that would result after the activity of the vir gene products on border sequences, generating a T-strand. In contrast, we designate as "biolistic events" those DNA inserts representing the process normally occurring after gene delivery into plant cells by the biolistic device. The initial criterion to distinguish biolistic events and putative agrolistic events was absence of luciferase activity in the transformed clone, arising from exclusion of the Luc coding region by T-DNA excision from pAVM1.

Maize suspension cells were bombarded with microprojectiles coated with pAVM1 plasmid DNA together with p35SAdhD1, p35SAdhD2 and/or p35SAdhE2 DNAs. As control, pAVM1 was also bombarded alone. Stable transformants were selected by growth on Basta-containing medium. About 5–8 calli could be recovered per filter after bombardment with pAVM1 alone. An average of 10 Basta-resistant clones could be recovered per filter 4–5 weeks after bombardment of maize cells with pAVM1, p35SAdhD1, p35SAdhD2 and p35SAdhE2 DNAs. Only some were further analyzed per plate. About 2–3 calli appeared on filter bombarded with pAVM1, p35SAdhD1 and p35SAdhD2 DNAs. This difference can be attributed to the presence of the virE2 gene that encodes for single-stranded DNA binding protein involved in the protection of the T-strand. This protein has been shown to be required for efficient transfer of the T-DNA but not for T-DNA production (Stachel et al., 1986).

The frequency of agrolistic events could be estimated by the ratio of the total number of Basta-resistant calli analyzed that did not express luciferase to total Basta-resistant calli. By this criterion, the frequency of agrolistic events was about 25% when pAVM1 was co-delivered with p35SAdhD1 and p35SAdhD2 DNA. This frequency slightly increased to about 50% when pwiE2 was also co-delivered with the plasmids described above.

Southern Analysis

At the molecular level, the transgenes representing an agrolistic event should hybridize with the Bar probe and not with the luc probe. Both types of events may occur in the same plant cell, but such clones would be scored genetically as biolistic events based on the presence of luciferase activity. Both biolistic and putative agrolistic events were investigated by southern hybridization to measure the frequency of each type of insertion.

Southern blot hybridization was performed on DNA from basta-resistant callus lines obtained after bombardment with (i) pAVM1 DNA and (ii) pAVM1, p35SAdhD1, p35SAdhD2 and p35SAdhE2 DNAs. Results are summarized in Table 13 below.

TABLE 13

Analysis of Basta-resistant calli recovered after bombardment of maize cells with pAVM1 with or without the vir genes

| Plasmids | Callus | Luc. activity | Southern | Type of events |
|---|---|---|---|---|
| pAVM1 | 14 | 14 Luc (+) | 3 | 3 B |
| pAVM1 + D1 + D2 | 10 | 2 Luc (−) | none analyzed | |
| | | 8 Luc (+) | | |
| pAVM1 + D1 + D2 + E2 | 44 | 14 Luc (−) | 7 | 4 A, 1 A + B, 2 B |
| | | 30 Luc (+) | 3 | 3 B |

Conclusions a) The ratio of Agrolistic event to biolistic event is about 35% with pAVM1 and is in the range of percentage usually found of 20–40%.

b) The presence of VirE2 can improve the transformation efficiency.

Since virE2 possesses nuclear localization signals and those are recognized in plants (for review, see Zupan and Zambryski, *Plant Physiol.* 107: 1041–1047 (1995)) higher rates of transformation were expected when this gene was introduced in planta. Transgenic plants expressing the virE2 gene are able to complement vire mutants of Agrobacterium, providing evidence that VirE2 protein plays an important role in the plant cells.

Example 8

Bombardment of virD1 and virD2 mRNA into Maize Cells

This example describes the delivery to plant cells of virD1 and virD2 genes as mRNA and their activity on T-DNA border sequences.

Materials and Methods

Maize Cells

Suspension cultures of maize (*Zea mays* L. ) initiated from cryopreserved embryogenic type II callus selected from immature embryos of an elite line related to B73 were grown in N6 liquid medium (Chu et al., 1975) supplemented with 30 g/l sucrose and 2 mg/l 2,4-dichlorophenoxy acetic acid (2,4-D) (2N63S). Cultures were incubated at 25° C. in the dark on an orbital shaker at 150 rpm. Suspension cultures were subcultured every 7 days by transferring 1 ml packed cell volume into 50 ml fresh 2N63S liquid medium. Maize cell suspensions used for bombardment experiments were taken from 3 day-old rapidly growing cultures. Before bombarding, approximately 0.5 ml of packed volume cells was vacuum filtered onto 7-cm filters (Whatman, N°4).

Tobacco Cells

The *Nicotiana tabacum* cell line NT-1 was grown in Murachige and Skoog medium supplemented with 2 mg/l of 2,4-D and sucrose (30g/l). Cells were subcultured once per week by adding 5ml of inoculum to 100 ml of fresh medium in 500 ml flasks. The flasks were incubated at 27° C. on a rotary shaker at 125 rpm. Aliquots of 0.5 ml from cells four days after subculture were spread onto sterile filter (Whatman No. 4). Filters were then transferred onto MS medium.

Plasmid Construction

1—Construction of a Vector Containing the T7 Promoter and the Poly A Tail:

A polylinker containing the following restriction sites (SphI-EcoRI-NheI-ClaI-BglII-Asp718-HindIII-XhoI-Hind*III, with the last HindIII as a killing site) was inserted into the SphI-HindIII sites of pT7RecA50. An oligomer designated Asp718- A(50)-DraI-HindIII was then inserted into the corresponding sites giving rise to pT7-A50. The complimentary strands of this oligomer have the following sequence:

X, was digested with BamHI and EcoRV and Fragment C was ligated into the vector to form pUC21-C. Next this product was digested with BamHI and SphI and the isolated Fragment AB from above was ligated in to reconstruct virD2. After digestion of the resulting plasmid, pUC21-virD2, with SphI and BglII, we gel purified Fragment ABC containing the tailored virD2 ORF.

D. Cloning virD2 into a T7 Transcription Vector

T7polyA, a transcription vector described above, was digested with SphI and BglII, and fragment ABC (=virD2) was ligated into position below a T7 promoter and above a block of 42 A residues.

mRNA Synthesis

The T7D1A50 and T7D2A50 plasmids were linearized with XhoI, which cuts immediately downstream of the poly(A) stretch. Linearized DNA was phenol/chloroform extracted and then ethanol precipitated. In vitro transcription of linearized DNA was carried out using the T7 polymerase from the T7 Cap-Scribe kit containing [$m^7G(5')ppp(5')$] (Boehringer). The integrity and concentration of mRNA were determined by agarose gel electrophoresis.

Sterilization of Biolistic Supplies

Gold particles (0.3 μm—Heraeus) were sterilized by placing 60 mg particles in 100% ethanol and 0.1% DEPC. Particles were rinsed 3 times with RNase-free water and then resuspended in 1 ml RNAse-free 50% glycerol solution. Aliquots of 50 μl prepared particles were used for 6 shots. Macrocarriers were submerged in 100% ethanol and 0.1% DEPC, then rinsed 3 times in 100% ethanol and air dried. Stopping screens were autoclaved.

Nucleic Acid Precipitation

DNA (1 μg) and mRNA (about 8 μg: 4 μg D1 and 4 μg D2 or 8 μg non-specific mRNA) were precipitated onto a 50 μl

```
5'     CGA ATT CGC TAG CAT CGA TAG ATC TGG TAC CAA AGC TTC TCG AGT 3'        (SEQ ID NO:23)
3'GTAC GCT TAA GCG ATC GTA GCT ATC TAG ACC ATG GTT TCG AAG AGC TCA TCG A 5
```

2—Construction of pT7D1A50:

EcoRI-BglII fragment of D1 coding region previously cloned into EcoRI-BamHI of pSG5 (from the EcoRI-BamHI fragment of p35SAdh1D1).

3—Construction of pT7D2polyA: (see FIGS. 16–26)

A. Isolation of Tailored Fragments

The virD2 coding region was excised from p35SD$_2$ with EcoRI and isolated by preparative gel electrophoresis and extraction of DNA from agarose. Internal sites necessitated that tailoring of the 5' and 3' ends of virD2 be undertaken on subfragments. The HindIII/EcoRI fragment isolated from the 5' end was trimmed with PvuI to produce Fragment A. The BamHI/EcoRI fragment isolated from the 3' end was trimmed with HaeIII to produce Fragment C. Central fragment B was obtained by HindIII/BamHI digestion.

B. Cloning of Fragments A and B

Vector pTC182 was digested with HindIII and SphI, and Fragment A plus adapter oligos for the SphI end (which restored the start codon) were ligated into place, forming pTC 182-A. his plasmid was digested with HindIII and BamHI, and Fragment B was ligated to the 3' end of A. Combined Fragment AB was excised and gel-purified after BamHI/SphI digestion of the esulting plasmid, pTC182-A-B.

C. Cloning of Fragments AB and C in a Modified pUC21 Vector

The portion of the pUC21 polylinker between BamHI and XbaI sites was removed and replaced by an oligonucleotide pair that restored most of the sites an added a BglII site required in our construction. The resulting plasmid, pUC21- suspension of gold particles (60 mg/ml; 0.3 um) by adding successively 0.5 μl Tris buffer (1M), 50 μl CaCl2 and 2.5 μl 0.1 M spermidine. After all agents were added, vortexing was continued for 3 minutes, after which the particles were sedimented by brief microcentrifugation (1 min). The supernatant was removed and the particles were washed once with cold 100% ethanol, and resuspended in 60 μl 100% ethanol. This mixture was vortexed, and 10 μl aliquots were pipetted onto a macrocarrier disk and allowed to air dry in a laminar flow hood.

Microprojectile Delivery into Plant Cells

Microprojectiles were delivered to plant cells by a particle accelerator (PDS-He1000; DuPont) using 1550 psi rupture disks with the sample positioned 5.5 cm from the launch assembly. A 100 μm mesh stainless steel screen was placed halfway between the stopping plate and the tissue. Target plates were bombarded 2 times.

Luciferase Assays

Luciferase and GUS were assayed in tissue extracts with the luciferase assay system of Promega according to the recommendation of the supplier. Luciferase and β-glucuronidase activities are expressed as light units detected by an Analytical Luminescence model 2001 Luminometer for 10 s at 25° C.

Results

Luciferase assays were performed 24-h after bombardment. mRNA of D1 and D2 were co-bombarded with p35SRBLuc that contains a right border sequence inserted between the 35S promoter and the luciferase coding sequence. In the control experiments, p35SRBLuc was bombarded with unspecific mRNA or D1 and D2 mRNA were co-delivered with pLUC DNA that does not contain any border sequences. Results are shown below in Table 14.

TABLE 14

Co-delivery of D1 and D2 mRNA with target plasmid into maize cells

| Target plasmids ± mRNA | Mean | ±SD | % control |
|---|---|---|---|
| pRB(+)Luc | 3.2 | ±0.3 | 100% |
| pRB(+)Luc + D1 mRNA | 2.7 | ±0.2 | 84% |
| pRB(+)Luc + D2 mRNA | 1.4 | ±0.2 | 44% |
| pRB(+)Luc + D1 mRNA + D2 mRNA (1:1:1) | 0.6 | ±0.2 | 18% |
| pRB(+)Luc + D1 mRNA + D2 mRNA (1:2:2) | 0.4 | ±0.1 | 12% |
| pRB(+)Luc + p35SAdhD1 + p35SAdhD2 (1:1:1) | 0.1 | ±0.1 | 3% |
| pLUC | 3.6 | ±0.2 | 100% |
| pLUC + D1 mRNA + D2 mRNA (1:1:1) | 3.7 | ±0.3 | 102% |

Following incubation for 24 hrs, tissues were homogenized and enzyme activities determined. A plasmid expressing the β-glucuronidase (GUS), pGUS, was included in each bombardment as a control for the efficiency of DNA transfer and the activity of reporter is expressed as a ratio of luciferase to GUS activity. Independent bombardments were analyzed and data are presented as mean values of 3 repetitions plus or minus standard deviation. % control values are determined from the ratio of the luciferase to β-glucuronidase activities to those activities observed with control plasmid.

Conclusion

Following co-delivery of D1 mRNA and D2 mRNA with pRB(+)Luc DNA, a 10-fold decrease in luciferase activity was observed. The two vir genes delivered as a mRNA to the plant cell appeared to have a synergistic effect. These observations strongly indicated that the decrease of luciferase activity seen was the result of a strand-specific nick at the right border sequence by vir gene products.

The advantage of mRNA delivery is that its effect is necessarily transient. There is no extraneous DNA of the helper plasmids.

Example 9
"Agrolistic" in Protoplasts

Transformation technologies are an important tool for the genetic manipulation and improvement of crop species (Raskin, 1996). Various systems of transformation allow the direct transfer of foreign genetic material into cells capable of giving rise to fertile plants. These systems include delivery of DNA to protoplasts by means of electroporation or direct DNA uptake, microinjection into cells, and gene transfer by bombardment with DNA-coated microprojectiles (for review, see Morrish and Fromm, 1992). In the existing delivery systems, there is a tendency towards integration of multiple copies of the foreign gene. There is a need for an approach that would result in a simple pattern of integration of the foreign gene with no vector sequences.

The transformation method described herein, designated "Agrolistic", has the potential to give rise to transgenic material with a simple pattern of insertion of the foreign gene and exclusion of vector sequences. The approach is to use plant expression cassettes for virulences genes that play a key role in the formation and protection of the T-DNA (virD1, virD2 and virE2) codelivered with a plasmid containing T-DNA border sequences flanking a selectable marker. In previous examples, this technology is shown to work when all these elements are delivered to the plant cell by the biolistic device.

In this example, we employ methods for the direct DNA delivery to protoplasts to deliver all these elements. We have found that virD1 and virD2 gene products delivered in this manner can indeed produce T-DNA-type insertion events and that inclusion of the virE2 gene product can increase the frequency of transformation.

Materials and Methods

Plasmids pCIB1711 is a pUC derivative containing the firefly luciferase gene driven by the cauliflower mosaic virus 35S (CaMV35S) promoter and is described in Example 3. For introduction of T-DNA borders, two synthetic oligonucleotides corresponding to the right border sequence of LBA5269 (Van Haaren et al., 1989) were annealed to yield the duplex: (ATCCGGCAGGATATATACCGTTGTAATTCTGCA) (SEQ ID NO:24). This duplex flanked by BamHI-PstI sites was inserted into the corresponding sites in pCIB1711 between the promoter and the luciferase coding sequence yielding pRBLuc (see FIG. 2). pNeoRBLuc contains a left border sequence, the neomycin phosphotransferase gene (nptII) and the luciferase gene with the right border inserted between the promoter and the luciferase coding region from pRB(+)Luc. The nptII gene driven by the nos (nopaline synthase) promoter was excised from the plasmid pBin19 as a 2.2 kb SacII-HindIII fragment. The left border sequence was excised from pBin19 as a BglII-EcoRI fragment. Both of these fragments were inserted into XbaI-HindIII sites of pRB(+)Luc. pNeoLuc is the equivalent of pNeoRBluc with no right border sequence inserted between the CaMV35S promoter and the luciferase coding region.

The virD1 and virD2 genes from pTiA6 were subcloned into expression vector pMF6 (Callis et al., 1987), consisting of the CaMV35S promoter (0.5 kb), the Adh1 first intron (0.5 kb), and the nopaline synthase (nos) polyadenylation region (0.25 kb) (FIG. 1). The 0.6 kb EcoRI-PstI fragment from pAD1187 corresponding to the virD1 coding sequence was cloned into pMF6 yielding p35SAdhD1. The virD2 coding sequence was excised as a 1.8 kb EcoRI fragment from pAD1190 (Ghai & Das, 1989) and cloned in pMF6 to give rise to p35SAdhD2.

The virE2 coding region was cloned from pw 108 that contains a 3 kb XhoI fragment of Agrobacterium Ti-plasmid pTiA6 (accession number X04784)(Winans al., 1987). The 687-bp SacI-SmaI fragment of pw 108 was first cloned into the corresponding sites of pKS(−) to give rise to pKS3'E2. The 924 bp HaeIII-SacI from pw 108 was combined with the SacI-PstI fragment from pKS3'E2 and an annealed pair of DNA oligonucleotides flanked by EcoRI-cohesive and blunt ends (AATTCATGGATCTTTCTGGCAATGAGAAATCCAGG) (SEQ ID NO:25) and cloned into the EcoRI-PstI sites of pBluescript KS—(Stratagene, Inc) to give rise to pKSE2. An XhoI-PstI fragment that covered the entire virE2 coding region was then subcloned into XhoI-PstI of pMF6 to give rise to p35SAdhE2.

Plant Material

Maize Suspension Cells

The suspension culture of Zea Mays cv Black Mexican Sweet (BMS) was maintained in N6 media (Chu et al., 1975) supplemented with 30 g/l sucrose and 2 mg/l 2,4-dichlorophenoxy acetic acid (2,4-D) (2N63S). Maize cell suspensions used for experiments were taken from 3 day-old rapidly growing cultures.

Protoplasts were isolated from cell suspension culture of maize inbred BMS (Black Mexican sweet ) as described in "Black Mexican sweet corn: its use for tissue cultures.

Maize for biological research", edited by W. F. Sheridan, Charlottesville, Va. Plant Molecular Biology Association (1982). p. 385–388.). Paromomycin (200 mg/l) was included in the medium 2 days after transformation. Independent microcalli that appeared about 4 weeks after transformation were transferred onto fresh plates supplemented with 200 μg/ml paromomycin. After two subcultures on the same medium, suspension cultures were initiated by inoculating about 100 mg of maize cells into 25 ml liquid medium supplemented with 200 μg/ml paromomycin.

Protoplasts were transformed with different concentrations of pNeoRBLuc DNA with or without p35SAdhD1, p35SAdhD2 and/or p35SAdhE2 as described in table 15.

DNA Extraction and Southern Blot Hybridization

Cell cultures were harvested by filtration 10 days after inoculation and frozen in liquid nitrogen. DNA was isolated as described (Hall et al., 1991).

Approximately 10 μg of genomic DNA was used for digestion with EcoRI. Following separation on a 0.7% agarose gel, the DNA was transferred to Hybond+membrane and hybridization was performed according to the conditions described by the manufacturer (Amersham). DNA probes were labeled with [a-$^{32}$P]dCTP using the oligo labeling kit of Pharmacia. The neo probe corresponded to a 0.3-kb PstI-SphI fragment of the nptII gene. The luc probe corresponded to a 0.7 kb XbaI-EcoRI fragment of the luciferase gene. For removal of probes, membranes were stripped with a solution of 0.5% SDS at 100° C. for 5 min.

Results

Experimental Design

A vector was designed to allow screening for VirD1-and-VirD2-mediated insertion events by a genetic test. The vector pNeoRBLuc contains a natural left border from a Ti plasmid, nos-NPTII-nos (a chimeric neomycin phosphotransferase II gene with nopaline synthase promoter and terminator sequences), a 35S promoter, a synthetic right border sequence and the luciferase coding region. Paromomycin resistant maize calli that were transformed by the usual mechanism would almost invariably contain the luciferase gene and express luciferase. In contrast, clones that fail to express any luciferase were candidate products of VirD1 and VirD2 mediated excision and T-strand integration. To express virD1, virD2 and virE2 genes in plant cells, their respective open reading frames (ORFs) were placed under the control of the CaMV35S promoter.

Analysis of Stable Transformants

Protoplasts were transformed with pNeoRBLuc plasmid DNA together with p35SAdhD1 and p35SAdhD2 and/or p35SAdhE2 DNAs in various ratios. As controls, pNeoRBLuc plasmid was also delivered alone. Stable transformants were selected by growth on paromycin-containing medium. An average of 120 paromomycin-resistant clones appeared per plate when pNeoRBluc was co-transformed with virD1 and virD2 genes, but only 30 calli were further analyzed. The number of paromomycin-resistant calli could reach 250 when virE2 was added to the pool of virulence genes.

Thirty paromomycin resistant clones were analyzed from each set of experiments, and about 10–40% were found not to express luciferase, suggesting a ca. 10–40% frequency of virD1–virD2 mediated integration events. This presumably underestimated the frequency of "agrolistic" events, since clones containing both inserts would be included in the 90% luciferase positive group. There was no significant difference in the frequency of calli not expressing the luciferase recovered from experiment with or without the virE2 gene.

Southern Blot Analysis of Transformant Clones

Southern blot hybridization was performed on DNA from control paromomycin-resistant callus lines obtained after bombardment with (i) pNeoRBLuc alone; (ii) pNeoRBLuc plasmid co-transformed with p35SAdhD1 and p35SAdhD2 DNAs and (iii) pNeoRBLuc plasmid co-transformed with p35SAdhD1, p35SAdhD2, and p35SAdhE2 DNAs.

Genomic DNA was digested with EcoRI, which produces a 3.9 kb fragment from the pNeoRBLuc plasmid that is homologous to both neo and luc probes. EcoRI has one site inside the T-DNA structure part of pNeoRBLuc and another one in the luciferase coding region.

Control transformants recovered from transformation of protoplasts with pNeoRBLuc alone exhibited the expected 3.9 kb EcoRI fragment hybridizing to both the luc and the neo probe. The copy number of this fragment is greater than 5 and in addition, multiple copies of rearranged and/or fragmented DNA were seen.

Southern blot analysis of DNA from paromomycin-resistant callus lines obtained after co-delivery of pNeoRBLuc with p35SAdhD1, p35SAdhD2 and/or p35SAdhE2plasmid DNAs is presented in Table 15. For Southern blot analysis, callus lines that tested negatively for the luciferase activity were chosen. For instance, among 8 transgenic maize lines recovered in the experiment #8 and analyzed by southern hybridization, 4 exhibited biolistic events and 4 exhibited putative agrolistic events. The estimated number of NPTII gene copies was in general 1 or 2 per transformant genome, as judged by a comparison with copy number standards included in the same hybridization filter. The callus lines that contained genomic DNA hybridizing with the neo probe and the luc probe exhibited less copies than the callus lines recovered from transformation with pNeoLuc DNA alone.

TABLE 15

Transformation experiments:

| Exp. # | Target plamids ± vir genes | Callus | Luc(−)/30 | Southern | type of event |
|---|---|---|---|---|---|
| #1 | pNeoRBLuc (5 μg) | 3 | | | |
| #2 | pNeoRBLuc (10 μg) | 20 | | | |
| #3 | pNeoRBLuc (20 μg) | 85 | | 4 [Luc+] | 4 B |
| #4 | pNeoRBLuc + p35AdhD1 + p35AdhD2 (5 μg + 20 μg + 20 μg) | 101 | 5 Luc(−) | 2 | 1 NT, 1 B |
| #5 | pNeoRBLuc + p35AdhD1 + p35AdhD2 (10 μg + 20 μg + 20 μg) | 123 | 5 Luc(−) | | 1 B + A, 3B, 1 NT |
| #6 | pNeoRBLuc + p35AdhD1 + p35AdhD2 (20 μg + 20 μg + 20 μg) | 147 | 6 Luc(−) | 6 | 1 A, 2 B, 3 NT |
| #7 | pNeoRBLuc + p35AdhD1 + p35AdhD2 + p35AdE2 (5 μg + 20 μg + 20 μg + 20 μg) | 219 | 9 Luc(−) | 5 | 2 A, 1 B, 1 NT |
| #8 | pNeoRBLuc + p35AdhD1 + p35AdhD2 + p35AdhE2 | 245 | 14 Luc(−) | 9 | 4 A, 4 B, 1 NT |

TABLE 15-continued

Transformation experiments:

| Exp. # | Target plamids ± vir genes | Callus | Luc(−)/30 | Southern | type of event |
|---|---|---|---|---|---|
| #9 | (10 μg + 20 μg + 20 μg + 20 μg) pNeoRBLuc + p35AdhD1 + p35AdhD2 + p35AdhE2 (10 μg + 20 μg + 20 μg + 20 μg) | 268 | 7 Luc(−) | 1 | 1 A |

Callus: Number of individual callus scored 4 weeks after transformation.

Conclusion

These results clearly show that this technology can simplify the pattern of integration of the foreign gene delivered to protoplasts. The frequency of VirD1–VirD2-mediated integration was about 20–30%. Furthermore, the addition of virE2 improved the transformation efficiency. This technology will aid in the recovery of transformed plants with simple pattern of integration of the gene of interest and with no extraneous DNA.

Example 10

Transformation of the CG00526 Genotype of Maize by Direct Bombardment Immature Zygotic Embryos and Isolation of Transformed Callus with the Use of Phosphinothricin as a Selection Agent.

Preparation of DNA for Bombardment using the Biolistic® Device.

Immature embryos or type I callus of maize may be transformed as described in pending U.S. patent application Ser. No. 08/438,666 filed May 10, 1995, the relevant portions of which are hereby incorporated herein by reference.

The DNA is prepared for microprojectile bombardment by chemical precipitation in the presence of micrometer size gold (typically 1.0 mm or 0.3 mm diameter), essentially according to the published procedure. In addition to gold, other dense particles of micrometer size may be used, such as tungsten or platinum. In one modification of the procedure, the particles themselves are first prepared by suspending them in water and sonicating. The sonicated particles are then pelleted by centrifugation and resuspended in an aqueous solution of 50% glycerol. Particles prepared in this way are then aliquoted into individual tubes containing approximately 3 mg of gold particles per tube in a volume of 50 μl. DNA is added to each tube in varying amounts depending upon the number of plasmids to be used, their sizes, and the final concentration of DNA desired.

Next, about 50 μl of 2.5 M $CaCl_2$ and about 20 μl of 0.1M spermidine are added, in that order, to each tube while vortexing for about 3 minutes. The DNA/gold complex is then gently centrifuged. The supernatant is removed. The particles are washed once with 250 μl of absolute ethanol, pelleted again, and then resuspended in about 75 μl of fresh absolute ethanol. Each tube prepared in this way is enough of the DNA/gold complex for six "shots" with the PDS-1000/He. Ten μl of the well-suspended DNA/gold complex is pipetted onto each macrocarrier sheet in a vibration-free environment.

In the PDS-1000/He device, a burst of helium is released by rupture of a plastic disk that is available in different pressure grades. For example, single disks, or combinations of disks, can be obtained which rupture at 200, 450, 650, 900, 1100 1350, 1550, 1800, 2000 and 2200 pounds per square inch of helium. This burst of gas propels the macrocarrier sheet, which is stopped by a stainless steel screen. The screen may be of different mesh sizes, such as 10×10, 16×16, 24×24, etc. Other settings are the macrocarrier flight distances, gap distance, and particle flight distance. These settings are described in detail in the manufacturer's user's manual. Typically, a gap distance of about 5.5 mm, a macrocarrier flight distance of about 10 mm and a particle flight distance of about 6 to 9 cm are used. In addition, a screen or baffle may be inserted within the particle flight distance between the stopping screen and the target plate. Such a screen or baffle disturbs the shock wave from the expanding gas thereby reducing damage to the target. In one example, stainless steel screens with an opening of about 100 μm is used. Other opening sizes and material composition may be used.

The immature embryos or Type I embryogenic callus may be arranged on the target plate in different patterns. Through a series of experiments, optimized patterns are developed for immature embryos. In one optimized pattern, the immature embryos are arranged in a circular pattern, the circle being about 2 cm in diameter. The immature embryos are placed on the periphery of the circle. Approximately 25 immature embryos are placed onto each target plate. Furthermore, the target plate may be angled relative to the microcarrier launch assembly. This ensures maximum saturation of the basipetal portion of the immature embryo by the particle spread. It is the basipetal portion of the immature embryo that gives rise to the embryogenic response.

In one example of the bombardment of Type I embryogenic callus, the callus is placed on the periphery of a circle about 1 cm diameter on a nutrient medium. The mechanical settings of the bombardment device may be placed at positions similar or identical to the settings recited above for the bombardment of immature embryos. It should be noted that the target pattern and gun settings are interrelated. In other words, the use of other mechanical settings on the microprojectile bombardment device can produce other optimal arrangements of the recipient tissue on the target plate. Other combinations of mechanical settings and target patterns are within the scope of the invention.

Transformation

Immature embryos are obtained approximately 14 days after self-pollination. The immature zygotic embryos are divided among different target plates containing medium capable of inducing and supporting embryogenic callus formation at 25 immature embryos per plate. The immature zygotic embryos are bombarded with a mixture of the plasmids p35SAdhD1, p35SAdhD2, and the T-DNA target plasmid (pbarRBluc or pAVM1) using the PDS1000/He device from BioRad. Expressible DNA for the virE2 gene may also be included. The plasmids are precipitated onto 0.3 or 1 μm gold particles essentially according to the published procedure as described above. Each target plate is shot two times with the plasmid and gold preparation using a burst pressure of 1100–1300 psi.

Since the plasmid pbarRBluc contains a chimeric gene coding for resistance to phosphinothricin, this substance is used to select transformed cells in vitro. This selection is applied at 3 mg/L one day after bombardment and maintained for a total of 8–12 weeks. The embryogenic callus so obtained is regenerated in the presence of 1 mg/l phosphinothricin. All calli are tested by the chlorophenol red (CR) test for resistance to PPT as described in U.S. patent application Ser. No. 759,243, filed Sep. 13, 1991, the relevant portions of which are hereby incorporated herein by reference. This assay utilizes a pH sensitive indicator dye to show which cells are growing in the presence of PPT. Cells that grow produce a pH change in the media and turn the indicator Chlorophenol Red yellow (from red). Plants expressing the resistance gene to PPT are easily identified in this test. Plants positive by the CR test are assayed by PCR for the presence of the bar gene.

Plants which contain the selectable marker gene are assayed for expression of the luciferase gene. The absence of luciferase activity is an indicator that the callus may be an Agrolistic event. An Agrolistic event is one in which the DNA is integrated into the maize DNA in a way that is analogous to the insertion of a T-DNA, but without the mediation of Agrobacterium. Plants which are negative for luciferase gene expression are analyzed by Southern blot. The pattern of bands observed by Southern blot analyses indicated which transformants were Agrolistic in nature.

Example 11
Transformation of the A188 Genotype of Maize by Direct Bombarding of Immature Zygotic Embryos and Isolation of Transformed Plants with the Use of Phosphinothricin as a Selection Agent.

An ear of genotype A188 is self-pollinated and immature zygotic embryos are obtained approximately 12–14 days later. Immature zygotic embryos are plated on 2JMS+5Dc plus $AgNO_3$ medium. After 16–20 hours, the immature zygotic embryos are transferred to the same medium but containing 12% sucrose. After 3–5 hours, the immature zygotic embryos are bombarded with a mixture of the plasmids p35SAdhD1, p35SAdhD2, and the T-DNA target plasmid (pbarRBluc or pAVM1) using the PDS1000/He device. Expressible DNA for the virE2 gene may also be included. The plasmids are precipitated onto 0.3 or 1 μm gold particles essentially according to the published procedure from BioRad, as described above. The particles are delivered using a burst pressure of 1100–1300 psi of helium. Each target plate is shot twice with the plasmid and gold particle preparation. After overnight incubation, the immature embryos are transferred to fresh maintenance medium containing 2% sucrose and phosphinothricin at 5–10 mg/L and subcultured approximately every two weeks onto the same medium. The embryogenic callus so obtained is regenerated in the presence of 1 mg/L phosphinothricin. All plants that regenerate are tested by the chlorophenol red (CR) test for resistance to PPT as described in U.S. patent application Ser. No. 759,243, filed Sep. 13, 1991, the relevant portions of which are hereby incorporated herein by reference. This assay utilizes a pH sensitive indicator dye to show which cells are growing in the presence of PPT. leaf pieces which are resistant to PPT produce a pH change in the media and turn the indicator yellow (from red). Plants expressing the resistance gene to PPT are easily identified in this test. Plants positive by the CR test are assayed by PCR for the presence of the bar gene.

Plants which contain the selectable marker gene are assayed for expression of the luciferase gene. The absence of luciferase activity is an indicator that the callus may be an Agrolistic event. An Agrolistic event is one in which the DNA is integrated into the maize DNA in a way that is analogous to the insertion of a T-DNA, but without the mediation of Agrobacterium. Plants which are negative for luciferase gene expression are analyzed by Southern blot. The pattern of bands on the Southern blot indicates which transformants are Agrolistic in nature.

Example 12
Transformation of the CG00526 Genotype of Maize by Bombarding of Type I Callus Derived from Immature Zygotic Embryos and Isolation of Transformed Callus with the Use of Phosphinothricin as a Selection Agent.

Type I callus is obtained from immature zygotic embryos using standard culture techniques. For gene delivery, approximately 300 mg of the Type I callus is prepared by chopping with a scalpel blade, rinsing 3 times with standard culture media containing 18% sucrose and immediately placed onto semi-solid culture medium again containing 18% sucrose. After approximately 4 hours, the tissue is bombarded using the PDS-1000/He Biolistic device from BioRad. Plasmids are precipitated onto 0.3 or 1 μm gold particles using the standard protocol from BioRad. Approximately 16–20 hours after gene delivery the callus is transferred to standard culture medium containing 2% sucrose and 10 mg/L phosphinothricin as Basta. The callus is subcultured on selection for 8 weeks, after which surviving and growing callus is transferred to standard regeneration medium for the production of plants.

All plants which regenerate are tested by the chlorophenol red (CR) test for resistance to PPT as described in U.S. patent application Ser. No. 759,243, filed Sep. 13, 1991, the relevant portions of which are hereby incorporated herein by reference. This assay utilizes a pH sensitive indicator dye to show which cells are growing in the presence of PPT. Cells which grow produce a pH change in the media and turn the indicator yellow (from red). Plants expressing the resistance gene to PPT are easily identified in this test. Plants positive by the CR test are assayed by PCR for the presence of the bar gene.

Calli which contain the selectable marker gene are assayed for expression of the luciferase gene. The absence of luciferase activity is an indicator that the callus may be an Agrolistic event. An Agrolistic event is one in which the DNA is integrated into the maize DNA in a way which is analogous to the insertion of a T-DNA, but without the mediation of Agrobacterium. Plants which are negative for luciferase gene expression are analyzed by Southern blot. The pattern of bands on the Southern blot indicates which transformants are Agrolistic in nature.

Example 13
Transformation of callus of the Genotype of Maize derived from B73 by Bombarding friable suspension culture cells derived from Immature Zygotic Embryos and Isolation of Transformed Callus with the Use of Phosphinothricin as a Selection Agent.

Friable callus was derived from plating immature embryos of genotype derived from B73 as described in U.S. Pat. No. 5,350,689, which is herein incorporated by reference.

Suspension cultures were subcultured weekly in N6 medium. Cells taken 3–5 days after subculture were harvested by filtering them through a 710 μm stainless steel filter, and then distributing them onto the surface of Durapore (see CGC1280/81) membranes. Approximately 0.4 g of cells were distributed on the surface of each 47 mm diameter membrane. The membranes were placed on N6 medium containing 12% sucrose for 3–5 hours before bombardment with a mixture of the plasmids carrying the vir genes (35SAdhD1, p35SAdhD2) and the T-DNA target plasmid (pbarRBluc or pAVM1) using the PDS1000/He device. Either equal amounts (1:1:1) of VirD1, virD2 and 35S-bar target T-DNA (each 1.3 μg total as 2 shots) or an excess of vir genes (2:2:1 μg as 2 shots) were delivered to the cells. Expressible DNA for the virE2 gene may also be included in such experiments.

The plasmids were precipitated onto 0.3 or 1 μm gold particles essentially according to the published procedure from BioRad, as described above. The particles were delivered using a burst pressure of 1100–1300 psi of helium. Each target plate received 2 shots. After overnight incubation, the membranes with the callus were transferred to fresh maintenance medium containing 2% sucrose and phosphinothricin at 3 mg/L. After 3 weeks the cells from each filter were spread onto the surface of 3 plates of 2N6 medium containing 10 mg/L Basta. Four weeks later, growing colonies were transferred to fresh 2N6 with 3 mg/l Basta, and one week later the calli so obtained were tested by the chlorophenol red (CR) test for resistance to PPT as described in U.S. patent application Ser. No. 759,243, filed Sep. 13, 1991, the relevant portions of which are hereby incorporated herein by reference. This assay utilizes a pH sensitive indicator dye to show which cells are growing in the presence of PPT. Cells that grow produce a pH change in the media and turn the indicator yellow (from red). Callus expressing the resistance gene to PPT were easily identified in this test. Positive pieces turned the medium either yellow or orange, indicating at least some resistance to PPT and they were placed on 2N6 medium containing 5 mg/l Basta.

Callus positive by the CR test were assayed by PCR for the presence of the bar or PAT gene.

TABLE 16

Identification of transformed lines of callus of maize

| Treatment | Yellow | Orange |
|---|---|---|
| Control(1) | 0 | 1 |
| Control(2) | 0 | 0 |
| 2:2:1 | 0 | 1* |
| 1:1:1(1)‡ | 21 | 2$ |
| 1:1:1(2) | 4 | 0 |

‡(1) and (2) were two duplicate treatments
*This colony was positive for luciferase.
$One of these was a putative Agrolistic event Callus lines that contained the selectable marker gene were assayed for expression of the luciferase gene. The absence of luciferase activity was an indicator that the callus may be an Agrolistic event. An Agrolistic event is one in which the DNA is integrated into the maize DNA in a way that is analogous to the insertion of a T-DNA, but without the mediation of Agrobacterium. Callus lines which were negative for luciferase gene expression were analyzed by Southern blot. The pattern of bands on the Southern blot (figure) indicated which transformants were Agrolistic in nature.

TABLE 17

Analysis of maize callus lines recovered after bombardment of maize cells with constructs suitable for delivering T-DNA inserts to maize

| Luciferase assay | Analyzed (Southern) | Agrolistic (putative) | Biolistic | Agro/ Biolistic |
|---|---|---|---|---|
| luc+ | 12 | 6 | 6 | |
| luc– | 11 | 9 | 4 | 3 | 2 |
| not analyzed: | 5 | | | |

The table shows that, from 23 cell lines which were analyzed in this experiment, 11 lacked luciferase activity, and from 9 of those analyzed by Southern blot, 4 contained only T-DNA-like inserts, and 2 contained both T-DNA-like inserts and typical inserts found after using a non-biological (in this case Biolistic) method to deliver the DNA.

Example 14

Transformation of callus of the CG00526 Genotype of Maize by Bombarding type I callus cells derived from Immature Zygotic Embryos and Isolation of Transformed Callus with the Use of Phosphinothricin as a Selection Agent.

Callus is derived from plating immature embryos of genotype CG00526 as described in pending U.S. patent application Ser. No. 08/438,666 filed May 10, 1995, the relevant portions of which are hereby incorporated herein by reference Cultures are subcultured weekly on maintenance medium (2DG4+0.5 mg/l 2,4-D) and cell clumps taken 2–3 days after subculture are placed on 2DG4 medium containing 12% sucrose for 3–5 hours. 16 target callus pieces per plate are arranged in a 8–10 mm diameter ring. The callus is bombarded with a mixture of the plasmids carrying the vir genes (35SAdhD1, p35SAdhD2) and the T-DNA target plasmid (pbarRBluc or pAVM1) using the PDS1000/He device. Either equal amounts (1:1:1) of VirD1, virD2 and 35S-bar target T-DNA (each 1.3 $\mu$g total as 2 shots) or an excess of vir genes (2:2:1 $\mu$g as 2 shots) are delivered to the cells. Expressible DNA for the virE2 gene may also be included.

The plasmids are precipitated onto 0.3 or 1 $\mu$m gold particles essentially according to the published procedure from BioRad, as described above. The particles are delivered using a burst pressure of 650 psi of helium. Each target plate receives 2 shots. After overnight incubation, the callus is transferred to fresh maintenance medium containing 2% sucrose. After a further 2 weeks the desirable callus (showing typical type I morphology) is subcultured to maintenance medium containing 120 mg/L Basta (PPT). Four weeks later, growing callus is transferred to fresh maintenance medium with 30 mg/l Basta.

The callus is subcultured on selection for a total of 8 weeks, after which surviving and growing callus is transferred to standard regeneration medium for the production of plants. All plants that regenerate are tested by the chlorophenol red (CR) test for resistance to PPT as described in U.S. patent application Ser. No. 759,243, filed Sep. 13, 1991, the relevant portions of which are hereby incorporated herein by reference. This assay utilizes a pH sensitive indicator dye to show which cells are growing in the presence of PPT. Cells which grow produce a pH change in the media and turn the indicator yellow (from red). Plants expressing the resistance gene to PPT are easily identified in this test. Plants positive by the CR test are assayed by PCR for the presence of the bar gene.

Plants that contain the selectable marker gene are assayed for expression of the luciferase gene. The absence of luciferase activity is an indicator that the callus may be an Agrolistic event. An Agrolistic event is one in which the DNA is integrated into the maize DNA in a way that is analogous to the insertion of a T-DNA, but without the mediation of Agrobacterium. Plants which are negative for luciferase gene expression are analyzed by Southern blot. The pattern of bands on the Southern blot indicates which transformants are Agrolistic in nature.

Example 15

Transformation of Maize Protoplasts with vir Genes and a T-DNA Target Sequence

Methods for the preparation of protoplasts from suspension cultures of *Zea mays* and transformation with DNA are described in U.S. Pat. No. 5,350,689.

The DNA used to transform the protoplasts consists, for example, of a mixture of the plasmids p35SAdhD1, p35SAdhD2, and the T-DNA target plasmid (pbarRBluc or pAVM1). Expressible DNA for the virE2 gene may also be included (see Example 7). Callus is recovered from the protoplasts, and plants are regenerated as described, using phosphinotricin as the selection agent. Transformed protoplast-derived cells are typically selected by application of selection with 3–5 mg/L PPT commencing 10 days after treatment with the DNA.

All plants that regenerate are tested by the chlorophenol red (CR) test for resistance to PT as described in U.S. patent application Ser. No. 759,243, filed Sep. 13, 1991, the relevant portions of which are hereby incorporated herein by reference. This assay utilizes a pH sensitive indicator dye to show which cells are growing in the presence of PPT. Cells which grow produce a pH change in the media and turn the indicator yellow (from red). Plants expressing the resistance gene to PPT are easily identified in this test. Plants positive by the CR test are assayed by PCR for the presence of the bar gene.

Plants that contain the selectable marker gene are assayed for expression of the luciferase gene. The absence of luciferase activity is an indicator that the callus may be an Agrolistic event. An Agrolistic event is one in which the DNA is integrated into the maize DNA in a way that is analogous to the insertion of a T-DNA, but without the mediation of Agrobacterium. Plants which are negative for luciferase gene expression are analyzed by Southern blot. The pattern of bands on the Southern blot indicates which transformants have a T-DNA-like insert. Cloning and sequencing of the border sequences may be carried out to confirm the nature of the inserts.

Although only a limited number of exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention.

What is claimed is:

1. A method for achieving stable integration of an exogenous DNA fragment into the genome of a plant cell, comprising introducing into said plant cell by non-biological means the following components:
   a) said DNA fragment bounded by T-DNA border sequences; and
   b) at least one isolated gene or RNA that encodes at least one Vir protein from the virulence region of an Agrobacterium Ti or Ri plasmid that promotes the integration of said exogenous DNA.

2. The method of claim 1, wherein the non-biological means is selected from microprojectile bombardment, electroporation, microinjection, induced uptake, and aerosol beam injection.

3. The method of claim 2, wherein said non-biological means is microprojectile bombardment.

4. The method of claim 1, wherein said at least one Vir protein is VirD2 alone or in combination with one or more of the group consisting of VirD1, VirC1, VirC2 and VirE2.

5. The method of claim 4, wherein said at least one Vir protein is selected from the group consisting of VirD2, a combination of VirD1 and VirD2, and a combination of VirD1, VirD2 and VirE2.

6. The method of claim 5, wherein said at least one protein is VirD2.

7. The method of claim 1, wherein component (a) resides on a plant viral vector.

8. The method of claim 1, wherein component (b) resides on a plant viral vector.

9. The method of claim 1, wherein components (a) and (b) reside on a plant viral vector.

10. The method of claim 1, wherein said plant cell is from a dicotyledonous plant.

11. The method of claim 10, wherein said dicotyledonous plant is selected from the group consisting of tobacco, cotton, oilseed rape, and soybean.

12. The method of claim 1, wherein said plant cell is from a monocotyledonous plant.

13. The method of claim 12, wherein said monocotyledonous plant is selected from the group consisting of maize, wheat, and rice.

14. The method of claim 1, wherein said exogenous DNA fragment comprises a chimeric gene.

15. The method of claim 14, wherein said chimeric gene expresses a protein in said plant cell.

16. The method of claim 1, wherein components (a) and (b) are introduced into said plant cell in the form of a single DNA molecule.

17. A method for producing a fertile transgenic plant having an exogenous DNA fragment bounded by T-DNA border sequences stably integrated into its genome, comprising the following steps:

a) integrating said exogenous DNA into the genome of a plant cell according to the method of claim 1; and b) regenerating the plant cell of step (a) to produce said fertile transgenic plant.

18. The method of claim 17, wherein said fertile transgenic plant is selected from the group consisting of tobacco, cotton, oilseed rape, soybean, maize, wheat, and rice.

* * * * *